US012187783B2

(12) United States Patent
Han et al.

(10) Patent No.: US 12,187,783 B2
(45) Date of Patent: *Jan. 7, 2025

(54) METHODS FOR TREATING MUSCLE WASTING AND BONE DISEASE USING NOVEL HYBRID ACTRIIB LIGAND TRAP PROTEINS

(71) Applicant: AliveGen Inc., Grand Cayman (KY)

(72) Inventors: Hq Han, Thousand Oaks, CA (US); Xiaolan Zhou, Newbury Park, CA (US)

(73) Assignee: AliveGen Inc, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/544,579

(22) Filed: Dec. 7, 2021

(65) Prior Publication Data

US 2022/0332791 A1    Oct. 20, 2022

Related U.S. Application Data

(63) Continuation of application No. 16/343,366, filed as application No. PCT/US2017/057351 on Oct. 19, 2017, now abandoned.

(60) Provisional application No. 62/410,595, filed on Oct. 20, 2016.

(51) Int. Cl.
| | | |
|---|---|---|
| C07K 14/71 | (2006.01) | |
| A61K 38/00 | (2006.01) | |
| A61K 45/06 | (2006.01) | |
| A61P 19/08 | (2006.01) | |
| A61P 21/00 | (2006.01) | |

(52) U.S. Cl.
CPC .............. *C07K 14/71* (2013.01); *A61K 45/06* (2013.01); *A61P 19/08* (2018.01); *A61P 21/00* (2018.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,885,794 A | 3/1999 | Mathews et al. | |
| 6,599,876 B2 | 7/2003 | Kojima et al. | |
| 6,656,475 B1 | 12/2003 | Lee et al. | |
| 6,891,082 B2 | 5/2005 | Lee et al. | |
| 7,148,321 B2 | 12/2006 | Gillies | |
| 7,709,605 B2 | 5/2010 | Knopf | |
| 7,785,587 B2 | 8/2010 | Whittemore et al. | |
| 7,842,663 B2 | 11/2010 | Knopf et al. | |
| 7,960,343 B2 | 6/2011 | Knopf et al. | |
| 8,058,229 B2 | 11/2011 | Seehra et al. | |
| 8,138,142 B2 | 3/2012 | Seehra et al. | |
| 8,178,488 B2 | 5/2012 | Knopf et al. | |
| 8,293,881 B2 | 10/2012 | Seehra et al. | |
| 8,343,933 B2 | 1/2013 | Knopf | |
| 8,765,385 B2 | 7/2014 | Kumar et al. | |
| 8,822,411 B2 | 9/2014 | Lee et al. | |
| 8,871,209 B2 | 10/2014 | Stitt et al. | |
| 9,181,533 B2 | 11/2015 | Seehra et al. | |
| 9,617,319 B2 | 4/2017 | Seehra et al. | |
| 9,745,559 B2 | 8/2017 | Seehra et al. | |
| 9,809,636 B2 | 11/2017 | Kumar et al. | |
| 9,844,528 B2 | 12/2017 | Dalton et al. | |
| 2004/0223966 A1 | 11/2004 | Wolfman et al. | |
| 2006/0068468 A1 | 3/2006 | Knopf et al. | |
| 2007/0117130 A1 | 5/2007 | Han et al. | |
| 2009/0047281 A1 | 2/2009 | Sherman | |
| 2009/0118188 A1 | 5/2009 | Knopf et al. | |
| 2010/0028332 A1 | 2/2010 | Sherman et al. | |
| 2010/0068215 A1 | 3/2010 | Seehra et al. | |
| 2010/0168020 A1 | 7/2010 | Sun et al. | |
| 2010/0267133 A1 | 10/2010 | Knopf et al. | |
| 2010/0310577 A1 | 12/2010 | Knopf et al. | |
| 2010/0316644 A1 | 12/2010 | Seehra et al. | |
| 2011/0038831 A1 | 2/2011 | Seehra et al. | |
| 2011/0070233 A1 | 3/2011 | Seehra et al. | |

(Continued)

FOREIGN PATENT DOCUMENTS

| | | |
|---|---|---|
| AU | 2012204098 B2 | 8/2012 |
| AU | 2015200950 B2 | 3/2015 |

(Continued)

OTHER PUBLICATIONS

Alan Koncarevic et al., "A Soluble Activin Receptor Type IIB Prevents the Effects of Androgen Deprivation on Body Composition and Bone Health," Endocrinology, vol. 151, issue 9, pp. 4289-4300, Jul. 23, 2010.

David Michael Hyman et al., "Preliminary Results from the First in Human Study of Activin A Inhibitor, STM 434, in Patients with Granulosa Cell Ovarian Cancer and Other Advanced Solid Tumors," presented at ASCO 2016, Chicago, IL, USA, Jun. 3-7, 2016.

Dianne Sako et al., "Characterization of the ligand binding functionality of the extracellular domain of activin receptor type IIB," The Journal of Biological Chemistry, vol. 285, No. 27, pp. 21037-21048, Jul. 2, 2010.

Extended European Search Report issued in Application No. EP16783603, dated Oct. 31, 2018, 11 pages.

(Continued)

*Primary Examiner* — Christina M Borgeest
(74) *Attorney, Agent, or Firm* — Craig A Crandall, APC; Craig A Crandall

(57) ABSTRACT

The present disclosure describes novel hybrid soluble ActRIIB-ECD polypeptides which fully retain binding affinity for myostatin and activin A but demonstrate significantly reduced binding to BMPs, especially BMP-9. The novel compositions described herein can be used to prepare novel hybrid ActRIIB ligand trap proteins, which can be used for modulating the growth of muscle, bone, cartilage, fat, fibroblast, blood and neuronal tissue to counteract muscle wasting, bone loss, anemia, inflammation and fibrosis in a therapeutically meaningful manner. Because these novel next-generation myostatin/activin inhibitors are safer and more effective molecules than the currently available myostatin inhibitors, they are useful in a wide variety of clinical indications.

8 Claims, 36 Drawing Sheets
Specification includes a Sequence Listing.

(56) References Cited

U.S. PATENT DOCUMENTS

| | | |
|---|---|---|
| 2011/0129469 A1 | 6/2011 | Koncarevic et al. |
| 2011/0135638 A1 | 6/2011 | Seehra et al. |
| 2011/0268736 A1 | 11/2011 | Beggs et al. |
| 2012/0328595 A1* | 12/2012 | Sun ............... A61K 31/513 424/94.5 |
| 2013/0177559 A1 | 7/2013 | Seehra et al. |
| 2014/0220033 A1 | 8/2014 | Han et al. |
| 2014/0348827 A1 | 11/2014 | Sun et al. |
| 2015/0276766 A1 | 10/2015 | Sung et al. |
| 2015/0359850 A1 | 12/2015 | Han et al. |
| 2015/0361163 A1 | 12/2015 | Kumar et al. |
| 2016/0046690 A1 | 2/2016 | Kumar et al. |
| 2016/0108379 A1 | 4/2016 | Knopf et al. |
| 2016/0289292 A1 | 10/2016 | Kumar et al. |
| 2016/0298093 A1 | 10/2016 | Kumar et al. |
| 2017/0202909 A1 | 7/2017 | Haqq et al. |
| 2022/0016208 A1* | 1/2022 | Bernstein ............... A61K 47/68 |

FOREIGN PATENT DOCUMENTS

| | | |
|---|---|---|
| EP | 2594280 A1 | 5/2013 |
| WO | 2000043781 A2 | 7/2000 |
| WO | 2002/010214 A2 | 2/2002 |
| WO | 2004/039948 A2 | 5/2004 |
| WO | 2005047334 A1 | 5/2005 |
| WO | 2006012627 A2 | 2/2006 |
| WO | 2006020884 A2 | 2/2006 |
| WO | 2007053775 A1 | 5/2007 |
| WO | 2008076437 A2 | 6/2008 |
| WO | 2008097541 A2 | 8/2008 |
| WO | 2008109167 A2 | 9/2008 |
| WO | 2009058346 A1 | 5/2009 |
| WO | 2009158015 A2 | 12/2009 |
| WO | 2009158025 A2 | 12/2009 |
| WO | 2009158035 A1 | 12/2009 |
| WO | 2010062383 A2 | 6/2010 |
| WO | 2010125003 A1 | 11/2010 |
| WO | 2011020045 A1 | 2/2011 |
| WO | 2011031901 A1 | 3/2011 |
| WO | 2011056896 A1 | 5/2011 |
| WO | 2011063018 A1 | 5/2011 |
| WO | 2012027065 A2 | 3/2012 |
| WO | 2013059347 A1 | 4/2013 |
| WO | 2013074557 A1 | 5/2013 |
| WO | 2013106175 A1 | 7/2013 |
| WO | 2014066486 A2 | 5/2014 |
| WO | 2014071158 A1 | 5/2014 |
| WO | 2014121221 A1 | 8/2014 |
| WO | 2015143403 A1 | 9/2015 |
| WO | 2015192111 A1 | 12/2015 |
| WO | 2015192127 A2 | 12/2015 |
| WO | 2016039796 A1 | 3/2016 |
| WO | 2016090077 A1 | 6/2016 |
| WO | 2016171948 A1 | 10/2016 |
| WO | 2017037634 A1 | 3/2017 |
| WO | 2017079591 A1 | 5/2017 |
| WO | 2017091706 A1 | 6/2017 |
| WO | 2017218592 A1 | 12/2017 |
| WO | 2018067874 A1 | 4/2018 |
| WO | 2018075747 A1 | 4/2018 |

OTHER PUBLICATIONS

H.Q. Han et al., "Myostatin/activin pathway antagonism: Molecular basis and therapeutic potential," The International Journal of Biochemistry & Cell Biology, vol. 45, issue 10, pp. 2333-2347, Oct. 2013.

International Search Report issued in Application No. PCT/US2016/027046, dated Sep. 23, 2016, 5 pages.

International Search Report issued in Application No. PCT/US2017/057351, dated Mar. 9, 2018, 8 pages.

John Lu et al., "Effects of a soluble activin type 2B receptor Fc fusion protein (STM 217) in TOV-21G, a mouse kenograft model of clear cell ovarian cancer," presented Jun. 3, 2013 at American Society of Clinical Oncology (ASCO), May 31-Jun. 4, 2013, Chicago, IL, USA.

Jon Ruckle et al., "Single-Dose, Randomized, Double-Blind, Placebo-Controlled Studyof ACE-011 (ActRIIA-IgG1) in Postmenopausal Women," Journal of Bone and Mineral Research, vol. 24, No. 4 (2009), pp. 744-752, published online on Dec. 1, 2008.

Kengo Yamawaki et al., "Adult-Specific Systemic Over-Expression Reveals Novel In Vivo Effects of the Soluble Forms of ActRIIA, ActRIIB and BMPRII," PLoS One 8(10): e78076, Oct. 21, 2013.

Lawrence S. Mathews et al., "Expression Cloning of an Activin Receptor, a Predicted Transmembrane Serine Kinase," Cell, vol. 65, 973-982, Jun. 14, 1991.

Marion Scharpfenecker et al., "BMP-9 signals via ALK1 and inhibits bFGF-inducedendothelial cell proliferation and VEGF-stimulated angiogenesis," Accepted Dec. 21, 2006, Journal of Cell Science 120 (6), 964-972, Published by the Company of Biologists 2007.

RS Pearsall et al., "ACE-2494, a Novel GDF Ligand Trap, Increases Muscle Mass upon Systemic Administration in Mice," Acceleron Pharma Inc., Oct. 1, 2015.

A. Mulivor et al., "ACE-083, a ligand trap for members of the TGFβ superfamily, increases muscle mass locally in a mouse model of Duchenne muscular dystrophy," Acceleron Pharma Inc., 19th Int'l Congress of the World Muscle Society, Oct. 9, 2014.

Sharon A. Townson et al., "Specificity and Structure of a High Affinity Activin Receptor-like Kinase 1 (ALK1) Signaling Complex," The Journal of Biological Chemistry, vol. 287, No. 33, pp. 27313-27325 and Supplemental Materials, Aug. 10, 2012.

Thomas B. Thompson et al., "Structures of an ActRIIB: activin A complex reveal a novel binding mode for TGF-β ligand: receptor interactions," The EMBO Journal, vol. 22, No. 7, pp. 1555-1566, 2003.

Verena Brand et al., "Impact of selective anti-BMP9 treatment on tumor cells and tumor angiogenesis," Molecular Oncology, vol. 10, issue 10, pp. 1603-1620, Dec. 2016.

Whitney L. Wooderchak-Donahue et al., "BMP9 Mutations Cause a Vascular-Anomaly Syndrome with Phenotypic Overlap with Hereditary Hemorrhagic Telangiectasia," Am. J. of Human Genetics, vol. 93, pp. 530-537, Sep. 5, 2013.

Ziaolan Zhou et al., "Reversal of Cancer Cachexia and Muscle Wasting by ACTRIIB Antagonism Leads to Prolonged Survival," Cell, vol. 142, issue 4, pp. 531-543, Aug. 20, 2010.

A. Mulivor et al., "A Modified Cysteine Knot Ligand Trap of the TGFβ Superfamily, ACE-083, Increases Muscle Mass Locally in Mice," Acceleron Pharma Inc., 13th Int'l Congress on Neuromuscular Diseases, Jul. 7, 2014.

Chiu, C.S. et al., "Increased muscle force production and bone mineral density in ActRIIB-Fc-treated mature rodents," J Gerontol A Biol Sci Med Sci, Oct. 2013; 68(10): 1181-1192.

Arounleut, P. et al., "A Myostatin Inhibitor (Propeptide-Fc) Increases Muscle Mass and Muscle Fiber Size in Aged Mice but Does not Increase Bone Density or Bone Strength," Exp Gerontol, Sep. 2013; 48(9): 898-904.

Written Opinion for corresponding Singaporean Patent Application No. 11201708351X dated Feb. 27, 201[9], mailed Feb. 28, 2019, 7 pages.

Smith, R.C. et al., "Myostatin Inhibitors as Therapies for Muscle Wasting Associated with Cancer and Other Disorders," Curr. Opin. Support Palliat. Care, Dec. 2013., 7(4): 352-360.

Greenwald et al, Three-finger toxin fold for the extracellular ligand binding domain of the type II activin receptor, Nature Structural Biology, 1999, 6, pp. 18-22.

Greenwald et al, The BMP7/ActRII Extracellular Domain Complex Provides New Insights into the Cooperative Nature of Receptor Assembly, Molecular Cell, 2003, 11, pp. 605-617.

Greenwald et al, A Flexible Activin Explains the Membrane-Dependent Cooperative Assembly of TGF-beta Family Receptors, Molecular Cell, 2004, 15, pp. 485-489.

Activin A receptor type I IA-*Homo sapiens*, from https://www.ncbi.nlm.nih.gov/protein/AAH67417.1report=genbank&log$=prottop&blast_rank=6&R1D=181 MVT2V015, pp. 1-3, accessed Dec. 14, 2018.

(56) References Cited

OTHER PUBLICATIONS

Water, from http://www.biology-online.org/dictionary/Water, pp. 1-3, accessed Apr. 24, 2014.
Brown et al, Crystal Structure of BMP-9 and Functional Interactions with Pro-region and Receptors, The Journal of Biological Chemistry, 2005, 280, pp. 25111-25118.
Cash et al, The structure of myostatin:follistatin 288: insights into receptor utilization and heparin binding, The EMBO Journal, 2009, 28, pp. 2662-2676.
Written Opinion of the International Search Authority cited in PCT/US2017/057351 dated Mar. 9, 2018, 12 pages.
Written Opinion of the International Search Authority cited in Application No. PCT/US2016/027046, dated Sep. 23, 2016, 7 pages.
Australian Examination Report No. 1 cited in AU2017345435 dated Nov. 26, 2020, 6 pages.
Liu et al., "Activin Receptor Type IIB Inhibition Improves Muscle Phenotype and Function in a Mouse Model of Spinal Muscular Atrophy", PLOS One, Nov. 21, 2016, pp. 1-17.
Mulivor et al., "A modified cysteine knot ligand trap of the TGFB superfamily, ACE-083, increases muscle mass locally in mice", Journal of Neuromuscular Diseases, 2014, vol. 1, supp. 1, p. S91-S92.
Koncarevic et al. "A Soluble Activin Receptor Type 118 Prevents the Effects of Androgen Deprivation on Body Composition and Bone Health," Endocrinology, Jun. 23, 2010 (Jun. 23, 2010), vol. 151, pp. 4289-4300.
Search Report and Written Opinion cited in Singapore Application No. 11201903450Y dated Jul. 10, 2020, 10 pages.
Partial Supplementary European Search Report cited in European Patent Application No. 17861941.7 dated Jun. 25, 2020, 23 pages.
Gray P. C. et al., Identification of a binding site on the type II activin receptor for activin and inhibin, Journal of Biological Chemistry, 2000, V. 275, N. 5, p. 3206-3212, the whole text.
Chen X. et al., Fusion protein linkers: property, design and functionality, Advanced drug delivery reviews, 2013, V. 65, N. 10, p. 1357-1369, the whole text, p. 1365.
Maeda Y. et al., Engineering of functional chimeric protein G-Vargula Luciferase, Analytical biochemistry, 1997, V. 249, N. 2, p. 147-152, the whole text.
Bogdanovich et al., "Myostatin propeptide-mediated amelioration of dystrophic pathophysiology," FASEB Journal, vol. 19, pp. 543-549, 2005.
Se-Jin Lee et al., "Regulation of myostatin activity and muscle growth," Proc. Nat. Acad. Sci., vol. 98, No. 16, pp. 9306-9311, Jul. 31, 2001.
Phillips, A., "The challenge of gene therapy and DNA Delivery", J Pharm Pharmacology, 2001; 53: 1169-1174 (Year: 2001).
Vidal etal., "Making sense of antisense", European Journal of Cancer, 2005; 41: 2812-2818 (Year: 2005).
Winkler, "Oligonucleotide conjugates for therapeutic applications", Ther. Deliv. 2013; 4: 791-809 (Year: 2013).
Jafarlou et al., "An Overview of the History, Applications, Advantages, Disadvantages and Prospects of Gene Therapy", Journal of Biological Regulators & Homeostatic Agents, 2016: 30: 315-321 (Year: 2016).
Derynck and Budi, "Specificity, versatility, and control of TGF-β family signaling", Sci. Signal. 12, eaav5183 (2019) Feb. 26, 2019; 25 pages total (Year: 2019).

* cited by examiner

METHODS FOR TREATING MUSCLE WASTING AND BONE DISEASE USING NOVEL HYBRID ACTRIIB LIGAND TRAP PROTEINS

CROSS-REFERENCE TO RELATED APPLICATIONS

This application is a continuation of U.S. Ser. No. 16/343,366, filed Apr. 18, 2019, which is a U.S. National Stage Application pursuant to 35 U.S.C. § 371 of PCT/US2017/057351, filed Oct. 19, 2017, which claims the benefit of U.S. Provisional Application No. 62/410,595, filed on Oct. 20, 2016, each of which is incorporated in its entirety by reference herein.

The instant application contains a Sequence Listing which has been submitted via EFS-Web and is hereby incorporated by reference in its entirety. Said Sequence Listing, created on Apr. 22, 2021, is named 2790-202US2_ST.TXT and is 135,298 bytes in size.

BACKGROUND ART

Muscle wasting refers to the progressive loss of muscle mass and/or to the progressive weakening and degeneration of muscles, including skeletal or voluntary muscles, cardiac muscles controlling the heart (cardiomyopathies), and smooth muscles. Chronic muscle wasting is a condition (i.e., persisting over a long period of time) characterized by progressive loss of muscle mass, as well as muscle weakening and degeneration. The loss of muscle mass occurs when the rate of muscle protein degradation exceeds muscle protein synthesis.

Muscle wasting is a debilitating and life-threatening disease state, which has been associated with the development of a number of chronic, neurological, genetic, inflammatory, fibrotic or infectious pathologies, including, e.g, muscular dystrophies, amyotrophic lateral sclerosis, myositis, denervation muscle atrophies, anorexia-cachexia syndrome, cancers, rheumatoid arthritis, osteoarthritis, insulin resistance/diabetes, sarcopenic obesity, age-related sarcopenia, androgen deprivation, corticosteroid myopathy, inflammatory bowel disease, liver cirrhosis, chronic obstructive pulmonary disease, pulmonary fibrosis, chronic renal disease, trauma, cardiomyopathy, chronic heart failure and HIV infection. Other conditions said to cause muscle wasting include chronic lower back pain, advanced age, damage to central nervous system, peripheral nerve injury, chemical injury, extended burns, hip/knee replacement, disuse atrophy, exposure to microgravity, and long term hospitalization.

Bone disease is considered any affliction that involves the skeletal system. Bone diseases can be very serious, and require prompt and effective treatment. Bone diseases can be very painful and can rob the patient of mobility and independence. While the causative factors vary by disease, many bone diseases are caused by, e.g., genetic factors, viral infection, chemical abnormalities, lack of bone collagen, injuries, fractures, damage to blood vessel, excessive use of alcohol, or the long term use of certain medications. Examples of bone disease include osteoporosis, osteomalacia, osteogenesis imperfecta, fibrous dysplasia, ossificans progressiva, corticosteroid-induced bone loss, bone fracture, bone metastasis and Paget's disease of the bone.

Activin IIA receptor (ActRIIA) and Activin IIB receptor (ActRIIB) are type II receptors for a subset of TGF-β family member ligands, including, e.g., activin A, myostatin (also known as GDF-8), growth differentiation factor-11 (GDF-11), and various other bone morphogenetic proteins (BMPs) such as BMP-3, BMP-6, BMP-9 (also known as GDF-2) and BMP-10. ActRIIA and ActRIIB have been identified as the type II receptors for activins, including activin A, activin B and activin AB. ActRIIB is a high affinity receptor for myostatin, a key negative regulator of muscle growth, and thus plays central role in controlling muscle mass. The binding of these ligands to ActRIIA and/or ActRIIB can regulate cell differentiation, apoptosis, protein synthesis and degradation, mineralization, hematopoiesis, angiogenesis, steroid synthesis, adhesion, migration, extracellular matrix production and fibrogenesis. The specific response depends upon the types and levels of the TGF-β ligands and receptors as well as the cellular state and environment. The ActRIIB signaling pathway mediates cellular responses via Smad2/3 transcription factors, and activation of the ActRIIB signaling pathway has been implicated in pathogenesis and progression of many diseases including muscle wasting, bone loss, fibrosis and inflammation. Several members of the TGF-β family, including myostatin, activins and GDF11, mediate Smad2/3 activation by coupling to ActRIIB.

Previous studies have shown that pharmacological sequestration of these ligands with ActRIIB-Fc leads to profound muscle growth and bone anabolism in animal models, demonstrating about three times more muscle growth than myostatin-neutralizing antibody in normal mice, and demonstrating the ability to further stimulate significant muscle gain in myostatin null mice (Chiu et al., J Gerontol A Biol Sci Med Sci., 68(10):1181-92, October 2013; Arounleut et al., Exp Gerontol., 48(9): 898-904, Sept 2013). And in addition to its marked anabolic effects on muscle and bone, ActRIIB-Fc has also been shown to have important anti-fibrosis and anti-inflammatory effects in pre-clinical models and various ActRIIA-Fc and ActRIIB-Fc fusion proteins have been, or are currently being clinically evaluated in patients for the treatment of muscle wasting disorders and/or bone diseases associated with the development of a number of chronic, neurological, genetic, inflammatory, fibrotic or infectious pathologies. For example, Acceleron Pharma's ACE-011, an ActRIIA-Fc fusion was clinically evaluated (Ph1, Ph2a) in patients with osteolytic lesions of multiple myeloma and osteoporosis and is currently being evaluated for chemotherapy-induced anemia (CIA) in patients with metastatic non-small cell lung cancer (NSCLC) (Ph2/3) (<ClinicalTrials.gov>) and for end-stage kidney disease in patients on hemodialysis and Acceleron Pharma's ACE-031, an ActRIIB-Fc fusion protein has been clinically evaluated (Ph1, Ph2) for therapeutic efficacy in Duchenne muscle dystrophy (DMD) (<ClinicalTrials.gov>).

Unfortunately, while appearing effective, the clinical potential of ACE-011 for treating osteoporosis was hampered by safety concerns (high RBC growth) and ACE-031, while demonstrating a significant muscle gain which was more pronounced than that caused by a myostatin-selective inhibitor, such as myostatin antibody, peptibody or propeptide, has been hampered by the adverse event in nose and gum bleeding seen in DMD patients, thus there was a clinical hold put on ACE-031 (Smith R. C. and Lin B. K., Curr Opin Support Palliat Care. 7(4): 352-360,2013). Consequently, ACE-031 was discontinued in DMD Phase2 trial due to the side effect of nose and gum bleeding despite its promising sign of efficacy to improve muscle mass and function in DMD patients. It thus appears that the wild-type ActRIIB-Fc is capable of blocking BMP9 mediated Smad1/3/8 signaling that is critical in maintaining blood vessel homeostasis, and this functional blockade of BMP9 by the wild-type ActRIIB is believed to be the underlying cause of the bleeding side effect, as compelling new genetic evidence has linked loss-of-function mutations of BMP9 to vascular anomaly and bleeding syndrome in humans (Wooderchak-Donahue et. al., Am J Hum Genet., 93(3): 530-537, September 2013).

So while there have been important advancements, there still exists a critical need to provide novel therapeutics, which are both highly effective and safe, for the treatment of muscle wasting and/or bone disease associated with the development of a number of chronic, neurological, genetic, inflammatory, fibrotic or infectious pathologies.

INCORPORATION BY REFERENCE

All references disclosed herein are hereby incorporated by reference in their entirety for all purposes.

DISCLOSURE OF THE INVENTION

In one aspect, the present disclosure provides a method of treating or preventing a muscle wasting in a subject, comprising administering to the subject a therapeutically effective amount (either as monotherapy or in a combination therapy regimen) of a hybrid ActRIIB ligand trap of the present disclosure in admixture with a pharmaceutically acceptable carrier, wherein such administration attenuates the loss of muscle mass and/or loss of muscle function. In various embodiments, the muscle wasting is associated with a disease selected from the group consisting of: muscular dystrophies (such as DMD, Becker MD, Limb-Girdle MD, Myotonic MD and FSHD), myositis (such as Dermatomyositis, Polymyositis and Inclusion body myositis), myopathy (including inherited myopathy as well as acquired myopathy such as myopathy induced by androgen-deprivation therapy, corticosteroids or statins), motoneuron disease (such as Lou Gehrig's Disease or ALS), spinal muscular atrophy (including Infantile progressive spinal muscular atrophy, Intermediate spinal muscular atrophy, Juvenile spinal muscular atrophy and Adult spinal muscular atrophy), neuromuscular junction disease (such as Myasthenia gravis, Lambert-Eaton syndrome and Botulism), peripheral nerve disease (such as Charcot-Marie tooth disease, Dejerine-Sottas disease and Friedreich's ataxia), spinal cord injury, stroke, neurodegenerative disease (including Parkinson's disease, Huntington's disease, Alzheimer's disease and Creutzfeldt-Jakob disease), cancer (such as lung cancer, pancreatic cancer, gastric cancer, colon cancer, prostate cancer, breast cancer, esophageal cancer, head and neck cancer, ovarian cancer, rhabdomyosarcoma, glioma, neuroblastoma, lymphoma, and multiple myeloma, skin cancer, and blood cancer), organ failure (such as heart failure, renal failure and liver failure, trauma (such as burns or motorcycle accident), disuse (such as long-term bed-rest, hospitalization, and spaceflight), infection (such as HIV, Polio and Sepsis), chronic obstructive pulmonary disease (COPD), and aging (such as sarcopenia, sarcopenic obesity and osteoarthritis).

In another aspect, the present disclosure provides a method of treating or preventing bone disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the bone disease is selected from the group consisting of: osteoporosis, renal osteodystrophy, osteogenesis imperfecta, fibrodysplasia ossificans progressiva, corticosteroid-induced bone loss, androgen-depriviation therapy-induced bone loss, hip fracture, cancer-induced bone loss, bone metastasis, Paget's disease, Rickets, osteomalacia, Perthes' disease and fibrous dysplasia.

In another aspect, the present disclosure provides a method of treating or preventing a metabolic disorder in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the metabolic disorder is selected from the group consisting of: metabolic syndrome, obesity, dyslipidemia, sarcopenic obesity, non-alcoholic fatty liver disease such as non-alcoholic steatohepatitis (NASH), alcoholic fatty liver disease, insulin resistance, diabetes as well as diabetic myopathy, diabetic nephropathy, diabetic neuropathy, diabetic retinopathy, and hemochromatosis.

In another aspect, the present disclosure provides a method of treating or preventing fibrosis in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the fibrosis is selected from the group consisting of: interstitial lung disease, idiotypic pulmonary fibrosis, cystic fibrosis, liver fibrosis, cirrhosis, biliary atresia, myocardial infarction, cardiac fibrosis, renal fibrosis, myelofibrosis, idiopathic retroperitoneal fibrosis, nephrogenic fibrosing dermopathy, inflammatory bowel disease or Crohn's disease, keloid, scleroderma, retroperitoneal fibrosis, and arthrofibrosis.

In another aspect, the present disclosure provides a method of treating or preventing an autoimmune/inflammatory disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the disease is selected from the group consisting of: autoimmune/inflammatory disorders including multiple sclerosis (MS), systemic sclerosis, diabetes (type-1), glomerulonephritis, myasthenia gravis, psoriasis, systemic lupus erythematosus, polymyositis, Crohn's disease, ulcerative colitis, and primary biliary cirrhosis, arthritis, asthma, and sepsis.

In another aspect, the present disclosure provides a method of treating cardiovascular disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the cardiovascular disease is selected from the group consisting of: heart failure, cardiac atrophy, pulmonary arterial hypertension (PAH), myocarditis, coronary artery disease, myocardial infarction, cardiac arrhythmias, heart valve disease, cardiomyopathy, pericardial disease, aorta disease, Marfan syndrome and cardiac transplant.

In another aspect, the present disclosure provides a method of treating or preventing cancer or cancer metastasis in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the cancer is selected from the group consisting of:

pancreatic cancer, gastric cancer, esophageal cancer, colorectal cancer, hepatoma, lung cancer, ovarian cancer, prostate cancer, bladder cancer, head and neck cancer, rhabdomyosarcoma, glioma, neuroblastoma, myeloma, lymphoma and leukemia, melanoma, carcinoma and myelodysplastic syndrome.

In another aspect, the present disclosure provides a method of treating or preventing chronic kidney disease (CKD) in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the CKD is selected from the group consisting of: CKD including renal failure, interstitial fibrosis, diabetic nephropathy, kidney dialysis, renal osteodystrophy, and protein energy wasting (PEW).

In another aspect, the present disclosure provides a method of treating or preventing arthritis in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the arthritis is selected from the group consisting of: rheumatoid arthritis, osteoarthritis, Still's disease, ankylosing spondylitis, back pain, Behçet's disease, bursitis, calcium pyrophosphate deposition disease, carpal tunnel syndrome, chondromalacia patella, chronic fatigue syndrome, complex regional pain syndrome, cryopyrin-associated periodic syndrome, degenerative disc disease, developmental-dysplasia of hip, Ehlers-Danlos syndrome, familial Mediterranean fever, fibromyalgia, giant cell arteritis, dermatomyositis, idiopathic arthritis, scleroderma, Kawasaki disease, lupus, mixed connective tissue disease, polymyositis, Pagets, rheumatic diseases, hemochromatosis, infectious Arthritis, psoriatic arthritis, reactive arthritis, reflex sympathetic dystrophy, Sjögren's disease, spinal stenosis and tendinitis.

In another aspect, the present disclosure provides a method of treating or preventing anorexia in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the anorexia is selected from anorexia nervosa and anorexia-cachexia syndrome.

In another aspect, the present disclosure provides a method of treating or preventing liver disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the liver disease is selected from the group consisting of non-alcoholic steatohepatitis, liver fibrosis or cirrhosis, cirrhosis, autoimmune hepatitis, hepatocellular carcinoma, liver failure, and liver transplantation.

In another aspect, the present disclosure provides methods for organ or tissue transplantation in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the transplantation is selected from the group consisting of: organ transplantations of the heart, kidneys, liver, lungs, pancreas, intestine and thymus or from tissue/cell transplantations of the muscles, bones, tendons, cornea, skin, heart valves, nerves and veins.

In another aspect, the present disclosure provides a method of treating or preventing anemia in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the anemia is selected from the group consisting of: anemia of inflammation, iron deficiency anemia, iron overload, thalassemia, hemolytic anemia, sickle cell anemia, pernicious anemia, fanconi anemia, myelodysplastic syndrome, aplastic anemia, cancer-associated anemia, chemotherapy-induced anemia, and anemia associated with CKD and kidney dialysis.

In another aspect, the present disclosure provides a method of treating pain in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the pain is selected from the group consisting of: neuropathic pain, somatic pain, visceral pain, inflammatory pain, cancer pain, back pain, and joint pain.

In another aspect, the present disclosure provides a method of treating aging in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the aging condition is selected from the group consisting of: frailty of the elderly, age-related sarcopenia, and osteoarthritis.

In another aspect, the present disclosure provides methods of inducing stem cell growth for tissue repair or organ regeneration in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the stem cell is selected from the group consisting of: muscle stem (satellite) cell, cardiac stem cell, bone marrow-derived mesynchymal stem cell and pluripotent stem cell.

In various embodiments, the hybrid ActRIIB ligand trap proteins comprise a hybrid soluble ActRIIB-ECD polypeptide having the amino acid sequence of SEQ ID NO: 1 wherein at least one of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide.

In various embodiments, the hybrid ActRIIB ligand trap proteins comprise hybrid soluble ActRIIB-ECD polypeptides having the amino acid sequence set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid soluble ActRIIB polypeptides are hybrid soluble ActRIIB polypeptides having an amino acid sequence that is at least 80%, 85%, 90%, 95%, 96%, 97%, 98%, or 99% identical to an amino acid sequence selected from SEQ ID NOs: 3-37, wherein the hybrid ActRIIB-ECD polypeptide is capable of binding myostatin and activin A, but demonstrates a decreased binding affinity for BMP9 relative to a wild-type ActRIIB-ECD polypeptide.

In various embodiments, the hybrid soluble ActRIIB-ECD polypeptide comprises the amino acid sequence selected from the group consisting of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 110, SEQ ID NO: 111, SEQ ID NO: 112, SEQ ID NO: 113, SEQ ID NO: 114, SEQ ID NO: 115, SEQ ID NO: 116, or SEQ ID NO: 117, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid soluble ActRIIB polypeptides are hybrid soluble ActRIIB polypeptides having an amino acid sequence that is at least 80%, 85%, 90%, 95%, 96%, 97%, 98%, or 99% identical to an amino acid sequence selected from SEQ ID NOs: 51-117, wherein the hybrid ActRIIB-ECD polypeptide is capable of binding myostatin and activin A, but demonstrates a decreased binding affinity for BMP9 relative to a wild-type ActRIIB-ECD polypeptide.

In various embodiments, the hybrid ActRIIB ligand trap proteins of the present disclosure comprise a hybrid soluble ActRIIB-ECD polypeptide and at least one heterologous protein, wherein the hybrid ActRIIB ligand trap is capable of binding myostatin and activin A, but demonstrates a decreased binding affinity for BMP9 relative to a wild-type ActRIIB-ECD polypeptide. In various embodiments, the heterologous protein is an Fc domain. In various embodiments, the Fc domain is a human IgG Fc domain. In various embodiments, the Fc domain is derived from the human IgG1 heavy chain constant domain sequence set forth in SEQ ID NO: 38. In various embodiments, the Fc domain is an Fc domain having the amino acid sequence set forth in SEQ ID NO: 39. In various embodiments, the Fc domain is derived from the human IgG2 heavy chain constant domain sequence set forth in SEQ ID NO: 40. In various embodiments, the Fc domain is an Fc domain having the amino acid sequence set forth in SEQ ID NO: 41. In various embodiments, the Fc domain is derived from the human IgG4 heavy chain constant domain sequence set forth in SEQ ID NO: 42.

In various embodiments, the Fc domain is an Fc domain having the amino acid sequence set forth in SEQ ID NO: 43.

In various embodiments, the heterologous protein is attached to the hybrid soluble ActRIIB-ECD polypeptide by a linker and/or a hinge linker peptide. The linker or hinge linker may be an artificial sequence of between 5, 10, 15, 20, 30, 40 or more amino acids that are relatively free of secondary structure. In various embodiments, the linker is rich in G/S content (e.g., at least about 60%, 70%, 80%, 90%, or more of the amino acids in the linker are G or S. In various embodiments, the linker has a (GGGGS (SEQ ID NO: 44)), motif, wherein n=1-6.

In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to a hybrid soluble ActRIIB-ECD polypeptide (e.g., any one of SEQ ID NOs: 3-37 or 51-117) of the present disclosure.

MODE(S) FOR CARRYING OUT THE DISCLOSURE

Figure 1:
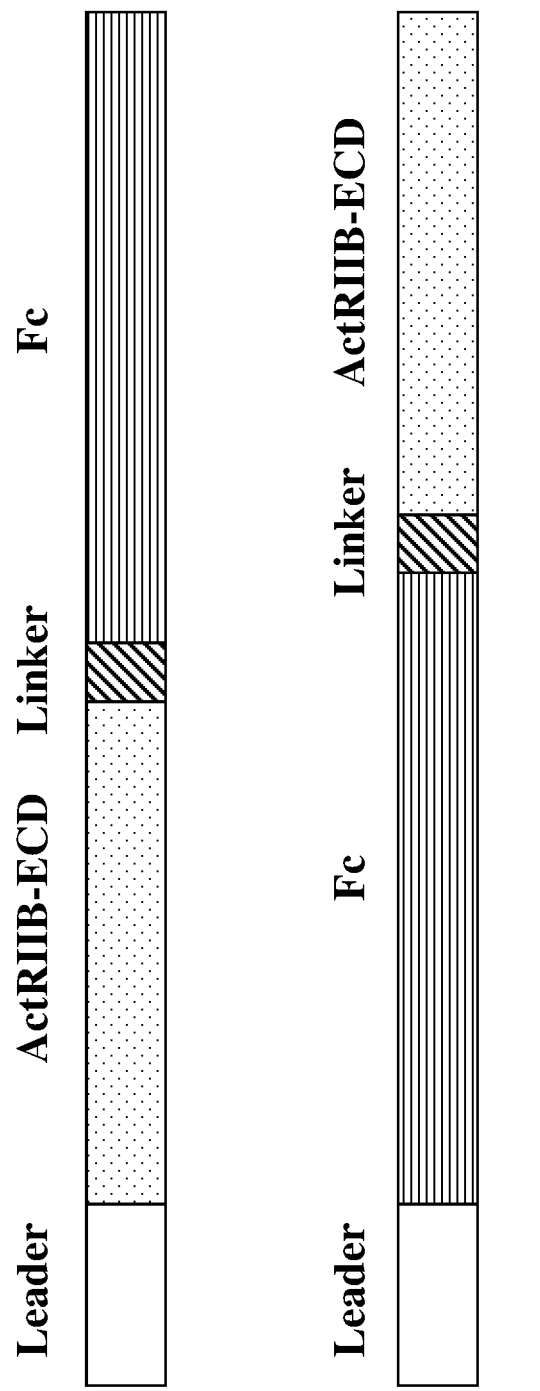
FIG. 1 depicts the two exemplary molecular configurations for the hybrid ActRIIB ligand trap proteins of the present disclosure.

The present disclosure provides for methods of treating myostatin-related or activin A-related disorders in a subject, comprising administering to said subject a therapeutically effective amount (either as monotherapy or in a combination therapy regimen) of a novel isolated hybrid ActRIIB ligand trap of the present disclosure in pharmaceutically acceptable carrier. The novel isolated hybrid ActRIIB ligand trap proteins genetically engineered as fusion proteins which function as a multi-cytokine antagonist designed to selectively block the actions of multiple cachectic (atrophy-inducing) cytokines without affecting the signaling of non-muscle related cytokines. In various embodiments, the hybrid ActRIIB ligand trap proteins comprise isolated hybrid soluble ActRIIB-ECD polypeptides which are capable of binding myostatin and activin A, but demonstrate a decreased binding affinity for BMP9 (i.e., retain myostatin- and activin A-neutralizing activities, but demonstrate dramatically reduced BMP9-neutralization) relative to a wild-type ActRIIB-ECD polypeptide. The present disclosure is based in part on the inventors' unique insight that a hybrid ActRIIB ligand trap engineered to exhibit significantly reduced binding to BMP9 (therefore having reduced BMP9-neutralization), while retaining its strong neutralizing activities against myostatin and activin, would provide myostatin inhibitors which are safer and more effective molecules than the currently available myostatin inhibitors. Specifically, the inventors postulated that a hybrid soluble ActRIIB polypeptide engineered to selectively replace amino acids residues within the ActRIIB extracellular domain (ECD) with corresponding amino acid residues from the ActRIIA ECD, could provide novel hybrid soluble ActRIIB polypeptides which preferentially neutralize myostatin and activin A (the key negative regulators of muscle growth) over BMP9. BMP9 plays an important role in a number of physiological processes (see, e.g, Tillet E, et al., Front Genet. 8; 5:456, 2015) and BMP9 signaling has been shown to be essential in maintaining normal blood vasculature/permeability (see e.g., David L., et al., Circ Res. 25; 102(8):914-22, 2008). It is thus postulated that subjects treated with the novel hybrid ActRIIB ligand trap proteins described herein may avoid the nose and gum bleeding side effects observed in subjects treated with the existing ActRIIB-Fc molecules which bind and neutralize BMP9 strongly. The therapeutic advantages provided by these novel hybrid ActRIIB ligand trap proteins offer next-generation therapeutics that are safe and effective for reversal of severe muscle loss and cachexia and for the treatment of a wide range of chronic catabolic diseases that involve muscle atrophy, bone loss, inflammation, and fibrosis.

Definitions

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

1) Alanine (A), Serine (S), and Threonine (T)
2) Aspartic acid (D) and Glutamic acid (E)
3) Asparagine (N) and Glutamine (Q)
4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant", "hybrid polypeptide" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Hybrids of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "heterologous" as used herein refers to a composition or state that is not native or naturally found, for example, that may be achieved by replacing an existing natural composition or state with one that is derived from another source. Similarly the expression of a protein in an organism other than the organism in which that protein is naturally expressed constitutes a heterologous expression system and a heterologous protein.

The term "antibody" as used herein refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

The term "Fc region" as used herein defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_{H2}$ domain and a $C_{H3}$ domain, and optionally comprises a $C_{H4}$ domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent, and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes.

An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

It is understood that aspect and embodiments of the disclosure described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variations.

Clinical Indications-Therapeutic Uses

In one aspect, the present disclosure provides a method for treating myostatin-related or activin A-related disorders in a subject, comprising administering to the subject a therapeutically effective amount (either as monotherapy or in a combination therapy regimen) of a hybrid ActRIIB ligand trap of the present disclosure in pharmaceutically acceptable carrier. Importantly, the pharmaceutical compositions of the present disclosure can be used to increase lean muscle mass as a percentage of body weight and decrease fat mass as percentage of body weight, while avoiding safety concerns reported for existing ActRIIB-Fc fusion protein-based therapeutics.

In one aspect, the present disclosure provides a method of treating or preventing a muscle wasting in a subject, comprising administering to the subject a therapeutically effective amount (either as monotherapy or in a combination therapy regimen) of a hybrid ActRIIB ligand trap of the present disclosure in admixture with a pharmaceutically acceptable carrier, wherein such administration attenuates the loss of muscle mass and/or loss of muscle function. In various embodiments, the muscle wasting is associated with a disease selected from the group consisting of: muscular dystrophies (such as DMD, Becker MD, Limb-Girdle MD, Myotonic MD and FSHD), myositis (such as Dermatomyositis, Polymyositis and Inclusion body myositis), myopathy (including inherited myopathy as well as acquired myopathy such as myopathy induced by androgen-deprivation therapy, corticosteroids or statins), motoneuron disease (such as Lou Gehrig's Disease or ALS), spinal muscular atrophy (including Infantile progressive spinal muscular atrophy, Intermediate spinal muscular atrophy, Juvenile spinal muscular atrophy and Adult spinal muscular atrophy), neuromuscular junction disease (such as Myasthenia gravis, Lambert-Eaton syndrome and Botulism), peripheral nerve disease (such as Charcot-Marie tooth disease, Dejerine-Sottas disease and Friedreich's ataxia), spinal cord injury, stroke, neurodegenerative disease (including Parkinson's disease, Huntington's disease, Alzheimer's disease and Creutzfeldt-Jakob disease), cancer (such as lung cancer, pancreatic cancer, gastric cancer, colon cancer, prostate cancer, breast cancer, esophageal cancer, head and neck cancer, ovarian cancer, rhabdomyosarcoma, glioma, neuroblastoma, lymphoma, and multiple myeloma, skin cancer, and blood cancer), organ failure (such as heart failure, renal failure and liver failure, trauma (such as burns or motorcycle accident), disuse (such as long-term bed-rest, hospitalization, and spaceflight), infection (such as HIV, Polio and Sepsis), chronic obstructive pulmonary disease (COPD), and aging (such as sarcopenia, sarcopenic obesity and osteroarthritis).

In another aspect, the present disclosure provides a method of treating or preventing bone disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the bone disease is selected from the group consisting of: osteoporosis, renal osteodystrophy, osteogenesis imperfecta, fibrodysplasia ossificans progressiva, corticosteroid-induced bone loss, androgen-depriviation therapy-induced bone loss, hip fracture, cancer-induced bone loss, bone metastasis, Paget's disease, Rickets, osteomalacia, Perthes' disease and fibrous dysplasia.

In another aspect, the present disclosure provides a method of treating or preventing a metabolic disorder in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the metabolic disorder is selected from the group consisting of: metabolic syndrome, obesity, dyslipidemia, sarcopenic obesity, non-alcoholic fatty liver disease such as non-alcoholic steatohepatitis (NASH), alcoholic fatty liver disease, insulin resistance, diabetes as well as diabetic myopathy, diabetic nephropathy, diabetic neuropathy, diabetic retinopathy, and hemochromatosis.

In another aspect, the present disclosure provides a method of treating or preventing fibrosis in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the fibrosis is selected from the group consisting of: interstitial lung disease, idiotypic pulmonary fibrosis, cystic fibrosis, liver fibrosis, cirrhosis, biliary atresia, myocardial infarction, cardiac fibrosis, renal fibrosis, myelofibrosis, idiopathic retroperitoneal fibrosis, nephrogenic fibrosing dermopathy, inflammatory bowel disease or Crohn's disease, keloid, scleroderma, retroperitoneal fibrosis, and arthrofibrosis.

In another aspect, the present disclosure provides a method of treating or preventing an autoimmune/inflammatory disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the disease is selected from the group consisting of: autoimmune/inflammatory disorders including multiple sclerosis (MS), systemic sclerosis, diabetes (type-1), glomerulonephritis, myasthenia gravis, psoriasis, systemic lupus erythematosus, polymyositis, Crohn's disease, ulcerative colitis, and primary biliary cirrhosis, arthritis, asthma, and sepsis.

In another aspect, the present disclosure provides a method of treating cardiovascular disease in a subject, comprising administering to the subject a therapeutically effective amount (either as monotherapy or in a combination therapy regimen) of a hybrid ActRIIB ligand trap of the present disclosure in admixture with a pharmaceutically acceptable carrier. In various embodiments, the cardiovascular disease is selected from the group consisting of: heart failure, cardiac atrophy, pulmonary arterial hypertension (PAH), myocarditis, coronary artery disease, myocardial infarction, cardiac arrhythmias, heart valve disease, cardiomyopathy, pericardial disease, aorta disease, Marfan syndrome and cardiac transplant.

In another aspect, the present disclosure provides for a method of treating cardiac dysfunction or heart failure in a subject comprising administering an effective amount of a hybrid ActRIIB ligand trap into the subject. The modulation may improve cardiac function of the subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The improvement of cardiac function can be evaluated by echocardiography to measure 1) cardiac pump functions focusing on the ejected blood volume and the efficiency of ejection and 2) myocardial functions focusing on the strength of myocardial contraction.

In another aspect, the present disclosure provides for a method of treating cancer cells in a subject, comprising administering to the subject a therapeutically effective amount (either as monotherapy or in a combination therapy regimen) of a hybrid ActRIIB ligand trap of the present disclosure in pharmaceutically acceptable carrier, wherein such administration inhibits the growth and/or proliferation of a cancer cell. Specifically, a hybrid ActRIIB ligand trap of the present disclosure is useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemia. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophthalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. In certain embodiments, the cancer will be a cancer with high expression of TGF-β family member, such as activin A, myostatin, TGF-β and GDF15, e.g., pancreatic cancer, gastric cancer, ovarian cancer, colorectal cancer, melanoma leukemia, lung cancer, prostate cancer, brain cancer, bladder cancer, and head-neck cancer.

In another aspect, the present disclosure provides for a method of treating chronic kidney disease (CKD) in a subject, comprising administering to the subject a therapeutically effective amount (either as monotherapy or in a combination therapy regimen) of a hybrid ActRIIB ligand trap of the present disclosure in pharmaceutically acceptable carrier, wherein such administration attenuates the loss of muscle mass and/or loss of muscle function or inhibits kidney fibrosis. Specifically, a hybrid ActRIIB ligand trap of the present disclosure is useful in treating CKD including renal failure, interstitial fibrosis, and kidney dialysis as well as protein energy wasting (PEW) associated with CKD. The modulation may improve CKD or PEW of the subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The improvement of renal function can be evaluated by measuring protein/creatinine ratio (PCR) in the urine and glomerular filtration rate (GFR). Improvement of PEW can be evaluated by measuring serum levels of albumin and inflammatory cytokines, rate of protein synthesis and degradation, body mass, muscle mass, physical activity and nutritional outcomes.

In another aspect, the present disclosure provides for methods for treating arthritis in a subject, comprising administering to the subject a therapeutically effective amount (either as monotherapy or in a combination therapy regimen) of a hybrid ActRIIB ligand trap of the present disclosure in pharmaceutically acceptable carrier. Specifically, a hybrid ActRIIB ligand trap of the present disclosure is useful in treating an arthritis selected from rheumatoid arthritis and osteoarthritis.

In another aspect, the present disclosure provides for methods for treating anorexia in a subject, comprising administering to the subject a therapeutically effective amount (either as monotherapy or in a combination therapy regimen) of a hybrid ActRIIB ligand trap of the present disclosure in pharmaceutically acceptable carrier. Specifically, a hybrid ActRIIB ligand trap of the present disclosure is useful in treating an anorexia selected from anorexia nervosa and anorexia-cachexia syndrome.

In another aspect, the present disclosure provides for methods for treating liver disease in a subject, comprising administering to the subject a therapeutically effective amount (either as monotherapy or in a combination therapy regimen) of a hybrid ActRIIB ligand trap of the present disclosure in pharmaceutically acceptable carrier. Specifically, a hybrid ActRIIB ligand trap of the present disclosure is useful in treating a liver disease selected from non-alcoholic fatty liver disease, non-alcoholic steatohepatitis, alcoholic fatty liver disease, liver cirrhosis, liver failure, autoimmune hepatitis and hepatocellular carcinoma.

In another aspect, the present disclosure provides for methods for organ or tissue transplantation in a subject, comprising administering to the subject a therapeutically effective amount (either as monotherapy or in a combination therapy regimen) of a hybrid ActRIIB ligand trap of the present disclosure in pharmaceutically acceptable carrier. Specifically, a hybrid ActRIIB ligand trap of the present disclosure is useful in treating a transplantation selected from organ transplantations of the heart, kidneys, liver, lungs, pancreas, intestine and thymus or from tissues transplantations of the bones, tendons, cornea, skin, heart valves, nerves and veins.

In another aspect, the present disclosure provides for methods for treating anemia in a subject, comprising administering to the subject a therapeutically effective amount (either as monotherapy or in a combination therapy regimen) of a hybrid ActRIIB ligand trap of the present disclosure in pharmaceutically acceptable carrier. In various embodiments, the anemia is selected from various anemia disorders including cancer-associated anemia, chemotherapy-induced anemia, chronic kidney disease-associated anemia, iron-deficiency anemia, thalassemia, sickle cell disease, aplastic anemia and myelodysplastic syndromes.

In another aspect, the present disclosure provides methods of treating pain in a subject, comprising administering a therapeutically effective amount of the pharmaceutical compositions of the invention to a subject in need thereof. In one embodiment, the subject is a human subject. In various embodiments, the pain is selected from neuropathic pain, inflammatory pain, or cancer pain.

In another aspect, the present disclosure provides a method of treating aging in a subject, comprising administering to the subject a therapeutically effective amount (either as monotherapy or in a combination therapy regimen) of a hybrid ActRIIB ligand trap of the present disclosure in pharmaceutically acceptable carrier. In various embodiments, the aging condition is selected from the group consisting of: frailty of the elderly, age-related sarcopenia, and osteoarthritis.

In another aspect, the present disclosure provides methods of inducing stem cell growth for tissue repair or organ regeneration in a subject, comprising administering to the subject a therapeutically effective amount (either as monotherapy or in a combination therapy regimen) of a hybrid ActRIIB ligand trap of the present disclosure in pharmaceutically acceptable carrier. In various embodiments, the stem cell is selected from the group consisting of: muscle stem (satellite) cell, cardiac stem cell, bone marrow-derived mesynchymal stem cell and pluripotent stem cell.

In various embodiments, the present disclosure provides for a method of inhibiting loss of muscle mass and/or muscle function in a subject comprising administering an effective amount of a hybrid ActRIIB ligand trap into the subject. The modulation may attenuate the loss of the muscle mass and/or function of the subject by at least 5%, 10%, at least 25%, at least 50%, at least 75%, or at least 90%. The inhibition of loss of muscle mass and function can be evaluated by using imaging techniques and physical strength tests. Examples of imaging techniques for muscle mass evaluation include Dual-Energy X-Ray Absorptiometry (DEXA), Magnetic Resonance Imaging (MRI), and Computed Tomography (CT). Examples of muscle function tests include grip strength test, stair climbing test, short physical performance battery (SPPB) and 6-minute walk, as well as maximal inspiratory pressure (MIP) and maximal expiratory pressure (MEP) that are used to measure respiratory muscle strength.

"Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

An exemplary, non-limiting daily dosing range for a therapeutically or prophylactically effective amount of a hybrid ActRIIB ligand trap of the disclosure can be 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the conditions to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 µg/ml, about 1 to 750 µg/ml, about 1 to 500 µg/ml, about 1 to 250 µg/ml, about 10 to 1000 µg/ml, about 10 to 750 µg/ml, about 10 to 500 µg/ml, about 10 to 250 µg/ml, about 20 to 1000 µg/ml, about 20 to 750 µg/ml, about 20 to 500 µg/ml, about 20 to 250 µg/ml, about 30 to 1000 µg/ml, about 30 to 750 µg/ml, about 30 to 500 µg/ml, about 30 to 250 µg/ml.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

The dosing frequency of the administration of the hybrid ActRIIB ligand trap pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the a hybrid ActRIIB ligand trap of the disclosure and one or more other therapeutic agents, is intended to mean, and does refer to and include the following: simultaneous administration of such combination of a hybrid ActRIIB ligand trap of the disclosure and therapeutic agent(s) to a subject in need of treatment, when such components are formulated together into a single dosage form which releases said components at substantially the same time to said subject; substantially simultaneous administration of such combination of a hybrid ActRIIB ligand trap of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of a hybrid ActRIIB ligand trap of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of a hybrid ActRIIB ligand trap of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present disclosure relates to methods of treating muscle wasting diseases in a subject, comprising administration of a combination of a) a therapeutically effective amount of a hybrid ActRIIB ligand trap of the present disclosure; and b) a second agent. This combination therapy may be particularly effective against a muscle wasting disease that is resistant or refractory to treatment using the second agent alone. In various embodiments, second agent is selected from growth hormone, ghrelin, IGF1, insulin, prednisone, corticosteroid therapy, androgen-deprivation therapy, anabolic steroids, antagonists to angiotensin or angiotensin receptor, antagonists to inflammatory cytokines such as TNF-alpha, IL-6, IL-1 and their receptors, and other antagonists to myostatin, activin A or another member of the TGF-beta family and to their receptors, bisphosphonates, RANKL inhibitors, agonists of peroxisome proliferator-activated receptors, β2 agonists, activator of PGC-1alpha, proteasome inhibitors, cancer therapeutics, chemotherapeutic agents, cell therapy, stem cell therapy, gene therapy, gene targeting therapy, and antisense oligonucleotide therapy.

In various embodiments, the combination therapy comprises administering a hybrid ActRIIB ligand trap and the second agent composition simultaneously, either in the same pharmaceutical composition or in separate pharmaceutical composition. In various embodiments, a hybrid ActRIIB ligand trap composition and the second agent composition are administered sequentially, i.e., a hybrid ActRIIB ligand trap composition is administered either prior to or after the administration of the second agent composition.

In various embodiments, the administrations of a hybrid ActRIIB ligand trap composition and the second agent composition are concurrent, i.e., the administration period of a hybrid ActRIIB ligand trap composition and the second agent composition overlap with each other.

In various embodiments, the administrations of a hybrid ActRIIB ligand trap composition and the second agent composition are non-concurrent. For example, in various embodiments, the administration of a hybrid ActRIIB ligand trap composition is terminated before the second agent composition is administered. In various embodiments, the administration second agent composition is terminated before a hybrid ActRIIB ligand trap composition is administered.

Activin Receptor Polypeptides

As used herein, the term activin type II B receptors (ActRIIB) refers to the human activin receptors having accession number NP_001097.2 (SEQ ID NO: 45 herein), and variants thereof. The term "wild-type ActRIIB-ECD" refers to the extracellular domain of ActRIIB, amino acids 1 to 134 (with signal sequence), or amino acids 19 through 134 of SEQ ID NO: 45 (without signal sequence) (referred to herein as SEQ ID NO: 46). The term activin type II A receptors (ActRIIA) refers to the human activin receptors having accession number UniProtKB/Swiss-Prot P27037.1 (SEQ ID NO: 47 herein), and variants thereof. The term "wild-type ActRIIA-ECD" refers to the extracellular domain of ActRIIA, amino acids 1 to 135 (with signal sequence), or amino acids 20 through 135 of SEQ ID NO: 46 (without signal sequence) (referred to herein as SEQ ID NO: 48).

Soluble Hybrid ActRIIB Polypeptides

The methods of the present disclosure utilize novel hybrid soluble ActRIIB-ECD polypeptides that are derived from wild-type ActRIIB-ECD and wild-type ActRIIA-ECD. The hybrid soluble ActRIIB polypeptides are specifically engineered by replacing one or more amino acids of a truncated wild-type ActRIIB-ECD with the amino acids from a truncated wild-type ActRIIA-ECD at corresponding positions based on sequence alignment between the two truncated ActRII ECD domains at the amino acid level. The one or more amino acid replacements are specifically selected for purposes of providing hybrid soluble ActRIIB-ECD polypeptides which demonstrate a marked reduction of BMP9-neutralization as compared to wild-type ActRIIB-ECD polypeptide, while fully retaining strong myostatin- and activin A-neutralization.

In various embodiments, the truncated extracellular domain of ActRIIB used to prepare the novel hybrid soluble ActRIIB-ECD polypeptides has the 110 amino acid sequence set forth in SEQ ID NO: 1:

```
                                            (SEQ ID NO: 1)
ETRECIYYNANWELERTNQSGLERCEGEQDKRLHCYASWRNSSGTIELVK

KGCWLDDFNCYDRQECVATEENPQVYFCCCEGNFCNERFTHLPEAGGPEV

TYEPPPTAPT
```

In various embodiments, the truncated extracellular domain of ActRIIA used to prepare the novel hybrid soluble ActRIIB-ECD polypeptides has the 110 amino acid sequence set forth in SEQ ID NO: 2:

```
                                            (SEQ ID NO: 2)
ETQECLFFNANWEKDRTNQTGVEPCYGDKDKRRHCFATWKNISGSIEIVK

QGCWLDDINCYDRTDCVEKKDSPEVYFCCCEGNMCNEKFSYFPEMEVTQP

TSNPVTPKPP
```

In various embodiments, the methods of the present disclosure ultilize isolated novel hybrid ActRIIB ligand trap proteins comprising novel hybrid soluble ActRIIB-ECD polypeptides which retain myostatin- and activin A-neutralizing activities, but demonstrate dramatically reduced BMP9-neutralization. In various embodiments, the hybrid ActRIIB ligand trap proteins comprise a hybrid soluble ActRIIB-ECD polypeptide having the amino acid sequence of SEQ ID NO: 1 wherein at least one of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least two of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least three of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least four of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least five of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least six of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least seven of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least eight of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least nine of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least ten of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least fifteen of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least twenty of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least twenty-five of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the hybrid ActRIIB ligand trap proteins comprise a hybrid soluble ActRIIB-ECD polypeptide having the amino acid sequence of SEQ ID NO: 1 wherein at least thirty of amino acid residues R3, I6, Y7, Y8, L14, E15, S20, L22, R24, E26, E28, Q29, L33, L48, Y36, S38, R40, S42, T45, K51, F58, Q64, E65, A68, T69, E70, E71, N72, Q74, F84, R88, T90, H91, L92, E94, A95, G96, G97, P98, E99, V100, Y102, E103, P105, P106, T107, A108, or T110 is substituted with another amino acid, and wherein the hybrid ActRIIB-ECD polypeptide is capable of binding myostatin and activin A, but demonstrates a decreased binding affinity for BMP9 relative to a wild-type ActRIIB-ECD polypeptide.

In various embodiments, the hybrid soluble ActRIIB-ECD polypeptide comprises the amino acid sequence of SEQ ID NO: 3, wherein amino acid residues E26, E28, Q29, L33, F58, Q64, E65, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 4, wherein amino acid residues E26, E28, Q29, L33, Q64, E65, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 5, wherein amino acid residues F58, Q64, E65, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 6, wherein amino acid residues F58, Q64, E65, A68, T69, E70, E71, and N72 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 7, wherein amino acid residues Q64, E65, A68, T69, E70, E71, and N72 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 8, wherein amino acid residues Q64, E65, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 9, wherein amino acid residues A68, T69, E70, E71, N72 and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 10, wherein amino acid residues A68, T69, E70, E71, and N72 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 11, wherein amino acid residues F58, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 12, wherein amino acid residues Q64, E65, A68, T69, E70, E71, N72, Q74, and F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 13, wherein amino acid residues A68, T69, E70, E71, N72, Q74, and F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 14, wherein amino acid residues R3, L14, E15, S20, L22, R24, E26, E28, Q29, and L33 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 15, wherein amino acid residues R3, L14, E15, S20, L22, and R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 16, wherein amino acid residues E26, E28, Q29, and L33 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 17, wherein amino acid residues L14, E15, S20, L22, and R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 18, wherein amino acid residues R3, L14, E15, S20, L22, and R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 19, wherein amino acid residues R3, L14, E15, and S20 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 20, wherein amino acid residues R3, L14, and E15 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 21, wherein amino acid residues L14 and E15 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 22, wherein amino acid residue R3 of SEQ ID NO: 1 has been replaced by the amino acid residues in the corresponding positions of SEQ ID NO: 2.

In various embodiments, the hybrid soluble ActRIIB-ECD polypeptide comprises the amino acid sequence of SEQ ID NO: 23, wherein amino acid residues Y36, S38, and K51 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 24, wherein amino acid residues E26, E28, Q29, L33, and F58 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 25, wherein amino acid residue E70 of SEQ ID NO: 1 has been replaced by the amino acid residues in the corresponding positions of SEQ ID NO: 2.

In various embodiments, the hybrid soluble ActRIIB-ECD polypeptide comprises the amino acid sequence of SEQ ID NO: 26, wherein amino acid residue F58 of SEQ ID NO: 1 has been replaced by the amino acid residues in the corresponding positions of SEQ ID NO: 2.

In various embodiments, the hybrid soluble ActRIIB-ECD polypeptide comprises the amino acid sequence of SEQ ID NO: 27, wherein amino acid residues F58 and E70 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 28, wherein amino acid residues E28, Q29, F58, and E70 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 29, wherein amino acid residues E28, F58, and E70 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 30, wherein amino acid residues E28 and E70 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 31, wherein amino acid residue E28 of SEQ ID NO: 1 has been replaced by the amino acid residues in the corresponding positions of SEQ ID NO: 2.

In various embodiments, the hybrid soluble ActRIIB-ECD polypeptide comprises the amino acid sequence of SEQ ID NO: 32, wherein amino acid residues E26, E28, Q29, L33, A68, T69, E70, E71, N72, and Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 33, wherein amino acid residues Y7, Y8, L14, E15, S20, L22, and R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 34, wherein amino acid residues Y36, S38, R40, S42, T45, and K51 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 35, wherein amino acid residues Q64 and E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 36, wherein amino acid residue F84 of SEQ ID NO: 1 have been replaced by the amino acid residue in the corresponding position of SEQ ID NO: 2.

In various embodiments, the hybrid soluble ActRIIB-ECD polypeptide comprises the amino acid sequence of SEQ ID NO: 37, wherein amino acid residues E28 and F58 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 51, wherein amino acid residues R3, I6, Y7, Y8, L14, E15, L22, R24, E26, E28, Q29, L33 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 52, wherein amino acid residues R3, I6, Y7, Y8, L14, E15, L22, R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 53, wherein amino acid residues I6, Y7, Y8, L14, E15, L22, R24 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 54, wherein amino acid residues I6, Y7, Y8, L14, E15, L22, R24, E26 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 55, wherein amino acid residues I6, Y7, Y8, L14, E15, L22, R24, E26, E28, Q29, L33 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 56, wherein amino acid residues I6, Y7, Y8, L14, E15, L22, R24, E26, E28, Q29, L33, Y36, S38, R40, S42, T45, L48, K51 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 57, wherein amino acid residues I6, Y7, Y8, L14, E15, L22, R24, E26, E28, Q29, L33, Y36, S38, R40, S42, T45, L48, K51, F58 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 58, wherein amino acid residues I6, Y7, Y8, L14, E15, L22, R24, E26, E28, Q29, L33, Y36, S38, R40, S42, T45, L48, K51, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 59, wherein amino acid residues R3, E26, E28, Q29, L33, Y36, S38, R40, S42, T45, L48, K51, F58 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 60, wherein amino acid residues E26, E28, Q29, L33, Y36, S38, R40, S42, T45, L48, K51, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 61, wherein amino acid residues E26, E28, Q29, L33, Y36, S38, R40, S42, T45, L48, K51, F58, Q64, E65, A68, T69, E70, E71, N72, Q74, F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 62, wherein amino acid residues Y36, S38, R40, S42, T45, L48, K51, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 63, wherein amino acid residues Y36, S38, R40, S42, T45, L48, K51, F58, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 64, wherein amino acid residues Y36, S38, R40, S42, T45, L48, K51, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 65, wherein amino acid residues Y36, S38, R40, S42, T45, L48, K51 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 66, wherein amino acid residues R3, E26, E28, Q29, L33, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 67, wherein amino acid residues R3, E26, E28, Q29, L33, F58, Q64, E65, A68, T69, E70, E71, N72, Q74, F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 68, wherein amino acid residues R3, E26, E28, Q29, L33, Y36, S38, R40, S42, T45, L48, K51, F58, Q64, E65, A68, T69, E70, E71, N72, Q74, F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 69, wherein amino acid residues R3, E26, E28, Q29, L33, Y36, S38, R40, S42, T45, L48, K51, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 70, wherein amino acid residues I6, Y7, Y8, L14, E15, L22, R24, Y36, S38, R40, S42, T45, L48, K51, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 71, wherein amino acid residues I6, Y7, Y8, L14, E15, L22, R24, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 72, wherein amino acid residues I6, Y7, Y8, L14, E15, L22, R24, E26, E28, Q29, L33, F58, Q64, E65, A68, T69, E70, E71, N72, Q74 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 73, wherein amino acid residues E26, E28, Q29, L33, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 74, wherein amino acid residues E26, E28, Q29, L33, K51, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 75, wherein amino acid residues E26, E28, Q29, L33, L48, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 76, wherein amino acid residues E26, E28, Q29, L33, T45, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 77, wherein amino acid residues E26, E28, Q29, L33, T45, L48, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 78, wherein amino acid residues E26, E28, Q29, L33, T45, L48, K51, Q64, E65 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 79, wherein amino acid residues Q64, E65, F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 80, wherein amino acid residues R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 81, wherein amino acid residues R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 82, wherein amino acid residues E26, E28, Q29, L33, F58, Q64, E65, A68, T69, E70, E71, N72, Q74, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 83, wherein amino acid residues E26, E28, Q29, L33, Q64, E65, A68, T69, E70, E71, N72, Q74, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 84, wherein amino acid residues E26, E28, Q29, L33, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 85, wherein amino acid residues E26, E28, Q29, L33, K51, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 86, wherein amino acid residues E26, E28, Q29, L33, L48, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 87, wherein amino acid residues E26, E28, Q29, L33, T45, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 88, wherein amino acid residues T45, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 89, wherein amino acid residues L48, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 90, wherein amino acid residues K51, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 91, wherein amino acid residues A68, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 92, wherein amino acid residues A68, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 93, wherein amino acid residues E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 94, wherein amino acid residues E71, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 95, wherein amino acid residues N72, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 96, wherein amino acid residues Q74, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 97, wherein amino acid residues E28, Q29, A68, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 98, wherein amino acid residues Q29, T69, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 99, wherein amino acid residues E28, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 100, wherein amino acid residues E28, Q29, K51, T69, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 101, wherein amino acid residues E28, Q29, L48, K51, T69E, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 102, wherein amino acid residues E26, E28, T45, L48, K51, T69, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 103, wherein amino acid residues Q29, L48, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 104, wherein amino acid residues E26, E28, L33, Q70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 105, wherein amino acid residues L33, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 106, wherein amino acid residues E26, T45, L48, Q64, E65, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 107, wherein amino acid residues L33, T45, T69, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 108, wherein amino acid residues L33, L48, T69, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 109, wherein amino acid residues L33, T45, L48, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 110, wherein amino acid residues E28, L48, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 111, wherein amino acid residues E28, T45, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 112, wherein amino acid residues E28, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 113, wherein amino acid residues L48, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 114, wherein amino acid residues E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 115, wherein amino acid residues E28, L48, T79, E70, R88, T90, H91, L92, A95, G96, G97, P98, E99, V100, Y102, E103, P105, P106, T107, A108, T110 of SEQ ID NO: 1 have been replaced by the amino acid residues in the corresponding positions of SEQ ID NO: 2, and E94 of SEQ ID NO: 1 has been replaced with Q.

In various embodiments, the hybrid soluble ActRIIB-ECD polypeptide comprises the amino acid sequence of SEQ ID NO: 116, wherein amino acid residues R3, I6, Y7, Y8, L14, E15, S20, L22, R24, E26, E28, Q29, L33, Y36, S38, R40, S42, T45, L48, K51, F58, Q64, E65, A68, T69, E71, N72, Q74, F84 of SEQ ID NO: 1 have been replaced by the amino acid residues in the corresponding positions of SEQ ID NO: 2.

In various embodiments, the hybrid soluble ActRIIB-ECD polypeptide comprises the amino acid sequence of SEQ ID NO: 117, wherein amino acid residues E26, E28, Q29, L33, F56, E68 of SEQ ID NO: 1 have been replaced by the amino acid residues in the corresponding positions of SEQ ID NO: 2.

Heterologous Proteins—Fc Domains

In another aspect, the hybrid ActRII ligand traps comprise a hybrid soluble ActRIIB-ECD polypeptide and at least one heterologous protein attached to the ActRIIB-ECD polypeptide either directly or through a linker sequence to form a fusion protein referred to herein as hybrid ActRIIB ligand trap. As used herein the term "fusion protein" refers to a protein having a heterologous polypeptide attached via recombinant DNA techniques. In various embodiments, the heterologous protein is selected from, but not limited to, a polyhistidine tag, a Glu-Glu, a glutathione S transferase (GST), a thioredoxin, a protein A, a protein G, a fluorescent protein, a maltose binding protein (MBP), a human serum albumin or an Fc polypeptide or Fc domain. In various embodiments, the Fc domain is a human IgG Fc domain. In various embodiments, the Fc domain is derived from the human IgG1 heavy chain constant domain sequence set forth in SEQ ID NO: 38. In various embodiments, the Fc domain is an Fc domain having the amino acid sequence set forth in SEQ ID NO: 39. In various embodiments, the Fc domain is derived from the human IgG2 heavy chain constant domain sequence set forth in SEQ ID NO: 40. In various embodiments, the Fc domain is an Fc domain having the amino acid sequence set forth in SEQ ID NO: 41. In various embodiments, the Fc domain is derived from the human IgG4 heavy chain constant domain sequence set forth in SEQ ID NO: 42. In various embodiments, the Fc domain is an Fc domain having the amino acid sequence set forth in SEQ ID NO: 43.

Linkers

The hybrid ActRIIB hybrid traps can optionally further comprise a "linker" or "hinge linker" sequence. Linkers serve primarily as a spacer between a hybrid soluble ActRIIB-ECD polypeptide a heterologous protein or other type of fusion or between two or more hybrid soluble ActRIIB-ECD polypeptides. In various embodiments, the heterologous protein is attached to the hybrid soluble ActRIIB-ECD polypeptide by a linker or a hinge linker peptide. The linker and/or hinge linker may be an artificial sequence of between 5, 10, 15, 20, 30, 40 or more amino acids that are relatively free of secondary structure. In various embodiments, the linkers comprise amino acids selected from glycine, alanine, proline, asparagine, glutamine, and lysine. In various embodiments, a linker is made up of a majority of amino acids that are sterically unhindered, such as glycine and alanine, and are polyglycines (particularly $(Gly)_5$, $(Gly)_8$, poly(Gly-Ala), and polyalanines. In various embodiments, the linker is rich in G/S content (e.g., at least about 60%, 70%, 80%, 90%, or more of the amino acids in the linker are G or S. In various embodiemnts, the linker has a (GGGGS (SEQ ID NO: 44))$_n$ motif, wherein n=1-6. Such linkers and hinge linkers have been described extensively in art (see, e.g., U.S. Pat. No. 8,410,043 (Sun et al), incorporated by reference herein for the purposes of teaching such linkers). In various embodiments, a linker having the amino acid sequence set forth in SEQ ID NO: 44 and a hinge linker having the amino acid sequence set forth in SEQ ID NO: 118 is used to link a human IgG1 Fc (SEQ ID NO: 39) or a human IgG4 Fc (SEQ ID NO: 43) to a hybrid soluble ActRIIB-ECD polypeptide of the present disclosure.

Linkers may also be non-peptide linkers. For example, alkyl linkers such as —NH—$(CH_2)_s$—C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

Molecular Configurations for the Hybrid ActRIIB Ligand Trap Proteins

It is understood that the different elements of the hybrid ActRIIB ligand trap may be arranged in any manner that is consistent with the desired functionality. For example, a heterologous protein may be placed C-terminal to a hybrid soluble ActRIIB-ECD polypeptide, or alternatively the hybrid soluble ActRIIB-ECD polypeptide may be placed C-terminal to a heterologous domain. The hybrid soluble ActRII-ECD polypeptide domain and the heterologous domain need not be adjacent, and additional domains or amino acid sequences may be included C- or N-terminal to either domain or between the domains (i.e. include a linker described herein). Exemplary molecular configurations for the novel ActRIIB ligand traps are depicted in FIG. 1.

An exemplary configuration of a synthetic DNA cassette encoding a hybrid ActRIIB ligand trap can be generally described as comprising the following elements: 1) a signal peptide (or leader sequence) placed at the N-terminus, which can be either the native signal peptide of ActRIIB (e.g., SEQ ID NO: 49) or any surrogate signal peptide capable of mediating the processing and secretion of secreted proteins (e.g., by using the human immunoglobulin light chain leader sequence (SEQ ID NO: 50) as a surrogate signal peptide, efficient secretion of hybrid ActRIIB ligand trap proteins in CHO cells can be achieved); 2) a hybrid soluble ActRIIB-ECD polypeptide sequence (e.g., any one of SEQ ID NOs: 3-37 or 51-117) fused to the signal peptide sequence; 3) a peptide linker sequence (e.g., SEQ ID NO: 44) and hinge linker sequence (SEQ ID NO: 118), and 4) an Fc domain (e.g., SEQ ID NOs: 39, 41 or 43) fused to the hybrid soluble ActRIIB-ECD polypeptide sequence by the peptide/hinge linker.

Examples of various embodiments of the present disclosure include, but are not limited to, the hybrid ActRIIB ligand trap proteins described in Table 2.

TABLE 2

| Hybrid Soluble ActRIIB-ECD polypeptide (SEQ ID NO) | Linker and Hinge Linker (SEQ ID NO) | Heterologous Protein (SEQ ID NO) | Leader Sequence (SEQ ID NO) |
|---|---|---|---|
| SEQ ID NO: 3 | SEQ ID NOs: 44 and 118 | SEQ ID NO: 39 or 41 or 43 | SEQ ID NO: 49 or 50 |
| SEQ ID NO: 4 | SEQ ID NOs: 44 and 118 | SEQ ID NO: 39 or 41 or 43 | SEQ ID NO: 49 or 50 |
| SEQ ID NO: 5 | SEQ ID NOs: 44 and 118 | SEQ ID NO: 39 or 41 or 43 | SEQ ID NO: 49 or 50 |
| SEQ ID NO: 6 | SEQ ID NOs: 44 and 118 | SEQ ID NO: 39 or 41 or 43 | SEQ ID NO: 49 or 50 |
| SEQ ID NO: 7 | SEQ ID NOs: 44 and 118 | SEQ ID NO: 39 or 41 or 43 | SEQ ID NO: 49 or 50 |
| SEQ ID NO: 8 | SEQ ID NOs: 44 and 118 | SEQ ID NO: 39 or 41 or 43 | SEQ ID NO: 49 or 50 |
| SEQ ID NO: 9 | SEQ ID NOs: 44 and 118 | SEQ ID NO: 39 or 41 or 43 | SEQ ID NO: 49 or 50 |
| SEQ ID NO: 10 | SEQ ID NOs: 44 and 118 | SEQ ID NO: 39 or 41 or 43 | SEQ ID NO: 49 or 50 |
| SEQ ID NO: 11 | SEQ ID NOs: 44 and 118 | SEQ ID NO: 39 or 41 or 43 | SEQ ID NO: 49 or 50 |
| SEQ ID NO: 12 | SEQ ID NOs: 44 and 118 | SEQ ID NO: 39 or 41 or 43 | SEQ ID NO: 49 or 50 |
| SEQ ID NO: 13 | SEQ ID NOs: 44 and 118 | SEQ ID NO: 39 or 41 or 43 | SEQ ID NO: 49 or 50 |
| SEQ ID NO: 14 | SEQ ID NOs: 44 and 118 | SEQ ID NO: 39 or 41 or 43 | SEQ ID NO: 49 or 50 |
| SEQ ID NO: 15 | SEQ ID NOs: 44 and 118 | SEQ ID NO: 39 or 41 or 43 | SEQ ID NO: 49 or 50 |
| SEQ ID NO: 16 | SEQ ID NOs: 44 and 118 | SEQ ID NO: 39 or 41 or 43 | SEQ ID NO: 49 or 50 |
| SEQ ID NO: 17 | SEQ ID NOs: 44 and 118 | SEQ ID NO: 39 or 41 or 43 | SEQ ID NO: 49 or 50 |
| SEQ ID NO: 18 | SEQ ID NOs: 44 and 118 | SEQ ID NO: 39 or 41 or 43 | SEQ ID NO: 49 or 50 |
| SEQ ID NO: 19 | SEQ ID NOs: 44 and 118 | SEQ ID NO: 39 or 41 or 43 | SEQ ID NO: 49 or 50 |
| SEQ ID NO: 20 | SEQ ID NOs: 44 and 118 | SEQ ID NO: 39 or 41 or 43 | SEQ ID NO: 49 or 50 |
| SEQ ID NO: 21 | SEQ ID NOs: 44 and 118 | SEQ ID NO: 39 or 41 or 43 | SEQ ID NO: 49 or 50 |
| SEQ ID NO: 22 | SEQ ID NOs: 44 and 118 | SEQ ID NO: 39 or 41 or 43 | SEQ ID NO: 49 or 50 |
| SEQ ID NO: 23 | SEQ ID NOs: 44 and 118 | SEQ ID NO: 39 or 41 or 43 | SEQ ID NO: 49 or 50 |
| SEQ ID NO: 24 | SEQ ID NOs: 44 and 118 | SEQ ID NO: 39 or 41 or 43 | SEQ ID NO: 49 or 50 |
| SEQ ID NO: 25 | SEQ ID NOs: 44 and 118 | SEQ ID NO: 39 or 41 or 43 | SEQ ID NO: 49 or 50 |
| SEQ ID NO: 26 | SEQ ID NOs: 44 and 118 | SEQ ID NO: 39 or 41 or 43 | SEQ ID NO: 49 or 50 |
| SEQ ID NO: 27 | SEQ ID NOs: 44 and 118 | SEQ ID NO: 39 or 41 or 43 | SEQ ID NO: 49 or 50 |
| SEQ ID NO: 28 | SEQ ID NOs: 44 and 118 | SEQ ID NO: 39 or 41 or 43 | SEQ ID NO: 49 or 50 |
| SEQ ID NO: 29 | SEQ ID NOs: 44 and 118 | SEQ ID NO: 39 or 41 or 43 | SEQ ID NO: 49 or 50 |
| SEQ ID NO: 30 | SEQ ID NOs: 44 and 118 | SEQ ID NO: 39 or 41 or 43 | SEQ ID NO: 49 or 50 |
| SEQ ID NO: 31 | SEQ ID NOs: 44 and 118 | SEQ ID NO: 39 or 41 or 43 | SEQ ID NO: 49 or 50 |
| SEQ ID NO: 32 | SEQ ID NOs: 44 and 118 | SEQ ID NO: 39 or 41 or 43 | SEQ ID NO: 49 or 50 |
| SEQ ID NO: 33 | SEQ ID NOs: 44 and 118 | SEQ ID NO: 39 or 41 or 43 | SEQ ID NO: 49 or 50 |
| SEQ ID NO: 34 | SEQ ID NOs: 44 and 118 | SEQ ID NO: 39 or 41 or 43 | SEQ ID NO: 49 or 50 |
| SEQ ID NO: 35 | SEQ ID NOs: 44 and 118 | SEQ ID NO: 39 or 41 or 43 | SEQ ID NO: 49 or 50 |
| SEQ ID NO: 36 | SEQ ID NOs: 44 and 118 | SEQ ID NO: 39 or 41 or 43 | SEQ ID NO: 49 or 50 |
| SEQ ID NO: 37 | SEQ ID NOs: 44 and 118 | SEQ ID NO: 39 or 41 or 43 | SEQ ID NO: 49 or 50 |
| SEQ ID NO: 51 | SEQ ID NOs: 44 and 118 | SEQ ID NO: 39 or 41 or 43 | SEQ ID NO: 49 or 50 |
| SEQ ID NO: 52 | SEQ ID NOs: 44 and 118 | SEQ ID NO: 39 or 41 or 43 | SEQ ID NO: 49 or 50 |
| SEQ ID NO: 53 | SEQ ID NOs: 44 and 118 | SEQ ID NO: 39 or 41 or 43 | SEQ ID NO: 49 or 50 |
| SEQ ID NO: 54 | SEQ ID NOs: 44 and 118 | SEQ ID NO: 39 or 41 or 43 | SEQ ID NO: 49 or 50 |
| SEQ ID NO: 55 | SEQ ID NOs: 44 and 118 | SEQ ID NO: 39 or 41 or 43 | SEQ ID NO: 49 or 50 |
| SEQ ID NO: 56 | SEQ ID NOs: 44 and 118 | SEQ ID NO: 39 or 41 or 43 | SEQ ID NO: 49 or 50 |
| SEQ ID NO: 57 | SEQ ID NOs: 44 and 118 | SEQ ID NO: 39 or 41 or 43 | SEQ ID NO: 49 or 50 |
| SEQ ID NO: 58 | SEQ ID NOs: 44 and 118 | SEQ ID NO: 39 or 41 or 43 | SEQ ID NO: 49 or 50 |
| SEQ ID NO: 59 | SEQ ID NOs: 44 and 118 | SEQ ID NO: 39 or 41 or 43 | SEQ ID NO: 49 or 50 |
| SEQ ID NO: 60 | SEQ ID NOs: 44 and 118 | SEQ ID NO: 39 or 41 or 43 | SEQ ID NO: 49 or 50 |
| SEQ ID NO: 61 | SEQ ID NOs: 44 and 118 | SEQ ID NO: 39 or 41 or 43 | SEQ ID NO: 49 or 50 |
| SEQ ID NO: 62 | SEQ ID NOs: 44 and 118 | SEQ ID NO: 39 or 41 or 43 | SEQ ID NO: 49 or 50 |
| SEQ ID NO: 63 | SEQ ID NOs: 44 and 118 | SEQ ID NO: 39 or 41 or 43 | SEQ ID NO: 49 or 50 |
| SEQ ID NO: 64 | SEQ ID NOs: 44 and 118 | SEQ ID NO: 39 or 41 or 43 | SEQ ID NO: 49 or 50 |
| SEQ ID NO: 65 | SEQ ID NOs: 44 and 118 | SEQ ID NO: 39 or 41 or 43 | SEQ ID NO: 49 or 50 |
| SEQ ID NO: 66 | SEQ ID NOs: 44 and 118 | SEQ ID NO: 39 or 41 or 43 | SEQ ID NO: 49 or 50 |
| SEQ ID NO: 67 | SEQ ID NOs: 44 and 118 | SEQ ID NO: 39 or 41 or 43 | SEQ ID NO: 49 or 50 |
| SEQ ID NO: 68 | SEQ ID NOs: 44 and 118 | SEQ ID NO: 39 or 41 or 43 | SEQ ID NO: 49 or 50 |
| SEQ ID NO: 69 | SEQ ID NOs: 44 and 118 | SEQ ID NO: 39 or 41 or 43 | SEQ ID NO: 49 or 50 |
| SEQ ID NO: 70 | SEQ ID NOs: 44 and 118 | SEQ ID NO: 39 or 41 or 43 | SEQ ID NO: 49 or 50 |
| SEQ ID NO: 71 | SEQ ID NOs: 44 and 118 | SEQ ID NO: 39 or 41 or 43 | SEQ ID NO: 49 or 50 |
| SEQ ID NO: 72 | SEQ ID NOs: 44 and 118 | SEQ ID NO: 39 or 41 or 43 | SEQ ID NO: 49 or 50 |
| SEQ ID NO: 73 | SEQ ID NOs: 44 and 118 | SEQ ID NO: 39 or 41 or 43 | SEQ ID NO: 49 or 50 |
| SEQ ID NO: 74 | SEQ ID NOs: 44 and 118 | SEQ ID NO: 39 or 41 or 43 | SEQ ID NO: 49 or 50 |

TABLE 2-continued

| Hybrid Soluble ActRIIB-ECD polypeptide (SEQ ID NO) | Linker and Hinge Linker (SEQ ID NO) | Heterologous Protein (SEQ ID NO) | Leader Sequence (SEQ ID NO) |
|---|---|---|---|
| SEQ ID NO: 75 | SEQ ID NOs: 44 and 118 | SEQ ID NO: 39 or 41 or 43 | SEQ ID NO: 49 or 50 |
| SEQ ID NO: 76 | SEQ ID NOs: 44 and 118 | SEQ ID NO: 39 or 41 or 43 | SEQ ID NO: 49 or 50 |
| SEQ ID NO: 77 | SEQ ID NOs: 44 and 118 | SEQ ID NO: 39 or 41 or 43 | SEQ ID NO: 49 or 50 |
| SEQ ID NO: 78 | SEQ ID NOs: 44 and 118 | SEQ ID NO: 39 or 41 or 43 | SEQ ID NO: 49 or 50 |
| SEQ ID NO: 79 | SEQ ID NOs: 44 and 118 | SEQ ID NO: 39 or 41 or 43 | SEQ ID NO: 49 or 50 |
| SEQ ID NO: 80 | SEQ ID NOs: 44 and 118 | SEQ ID NO: 39 or 41 or 43 | SEQ ID NO: 49 or 50 |
| SEQ ID NO: 81 | SEQ ID NOs: 44 and 118 | SEQ ID NO: 39 or 41 or 43 | SEQ ID NO: 49 or 50 |
| SEQ ID NO: 82 | SEQ ID NOs: 44 and 118 | SEQ ID NO: 39 or 41 or 43 | SEQ ID NO: 49 or 50 |
| SEQ ID NO: 83 | SEQ ID NOs: 44 and 118 | SEQ ID NO: 39 or 41 or 43 | SEQ ID NO: 49 or 50 |
| SEQ ID NO: 84 | SEQ ID NOs: 44 and 118 | SEQ ID NO: 39 or 41 or 43 | SEQ ID NO: 49 or 50 |
| SEQ ID NO: 85 | SEQ ID NOs: 44 and 118 | SEQ ID NO: 39 or 41 or 43 | SEQ ID NO: 49 or 50 |
| SEQ ID NO: 86 | SEQ ID NOs: 44 and 118 | SEQ ID NO: 39 or 41 or 43 | SEQ ID NO: 49 or 50 |
| SEQ ID NO: 87 | SEQ ID NOs: 44 and 118 | SEQ ID NO: 39 or 41 or 43 | SEQ ID NO: 49 or 50 |
| SEQ ID NO: 88 | SEQ ID NOs: 44 and 118 | SEQ ID NO: 39 or 41 or 43 | SEQ ID NO: 49 or 50 |
| SEQ ID NO: 89 | SEQ ID NOs: 44 and 118 | SEQ ID NO: 39 or 41 or 43 | SEQ ID NO: 49 or 50 |
| SEQ ID NO: 90 | SEQ ID NOs: 44 and 118 | SEQ ID NO: 39 or 41 or 43 | SEQ ID NO: 49 or 50 |
| SEQ ID NO: 91 | SEQ ID NOs: 44 and 118 | SEQ ID NO: 39 or 41 or 43 | SEQ ID NO: 49 or 50 |
| SEQ ID NO: 92 | SEQ ID NOs: 44 and 118 | SEQ ID NO: 39 or 41 or 43 | SEQ ID NO: 49 or 50 |
| SEQ ID NO: 93 | SEQ ID NOs: 44 and 118 | SEQ ID NO: 39 or 41 or 43 | SEQ ID NO: 49 or 50 |
| SEQ ID NO: 94 | SEQ ID NOs: 44 and 118 | SEQ ID NO: 39 or 41 or 43 | SEQ ID NO: 49 or 50 |
| SEQ ID NO: 95 | SEQ ID NOs: 44 and 118 | SEQ ID NO: 39 or 41 or 43 | SEQ ID NO: 49 or 50 |
| SEQ ID NO: 96 | SEQ ID NOs: 44 and 118 | SEQ ID NO: 39 or 41 or 43 | SEQ ID NO: 49 or 50 |
| SEQ ID NO: 97 | SEQ ID NOs: 44 and 118 | SEQ ID NO: 39 or 41 or 43 | SEQ ID NO: 49 or 50 |
| SEQ ID NO: 98 | SEQ ID NOs: 44 and 118 | SEQ ID NO: 39 or 41 or 43 | SEQ ID NO: 49 or 50 |
| SEQ ID NO: 99 | SEQ ID NOs: 44 and 118 | SEQ ID NO: 39 or 41 or 43 | SEQ ID NO: 49 or 50 |
| SEQ ID NO: 100 | SEQ ID NOs: 44 and 118 | SEQ ID NO: 39 or 41 or 43 | SEQ ID NO: 49 or 50 |
| SEQ ID NO: 101 | SEQ ID NOs: 44 and 118 | SEQ ID NO: 39 or 41 or 43 | SEQ ID NO: 49 or 50 |
| SEQ ID NO: 102 | SEQ ID NOs: 44 and 118 | SEQ ID NO: 39 or 41 or 43 | SEQ ID NO: 49 or 50 |
| SEQ ID NO: 103 | SEQ ID NOs: 44 and 118 | SEQ ID NO: 39 or 41 or 43 | SEQ ID NO: 49 or 50 |
| SEQ ID NO: 104 | SEQ ID NOs: 44 and 118 | SEQ ID NO: 39 or 41 or 43 | SEQ ID NO: 49 or 50 |
| SEQ ID NO: 105 | SEQ ID NOs: 44 and 118 | SEQ ID NO: 39 or 41 or 43 | SEQ ID NO: 49 or 50 |
| SEQ ID NO: 106 | SEQ ID NOs: 44 and 118 | SEQ ID NO: 39 or 41 or 43 | SEQ ID NO: 49 or 50 |
| SEQ ID NO: 107 | SEQ ID NOs: 44 and 118 | SEQ ID NO: 39 or 41 or 43 | SEQ ID NO: 49 or 50 |
| SEQ ID NO: 108 | SEQ ID NOs: 44 and 118 | SEQ ID NO: 39 or 41 or 43 | SEQ ID NO: 49 or 50 |
| SEQ ID NO: 109 | SEQ ID NOs: 44 and 118 | SEQ ID NO: 39 or 41 or 43 | SEQ ID NO: 49 or 50 |
| SEQ ID NO: 110 | SEQ ID NOs: 44 and 118 | SEQ ID NO: 39 or 41 or 43 | SEQ ID NO: 49 or 50 |
| SEQ ID NO: 111 | SEQ ID NOs: 44 and 118 | SEQ ID NO: 39 or 41 or 43 | SEQ ID NO: 49 or 50 |
| SEQ ID NO: 112 | SEQ ID NOs: 44 and 118 | SEQ ID NO: 39 or 41 or 43 | SEQ ID NO: 49 or 50 |
| SEQ ID NO: 113 | SEQ ID NOs: 44 and 118 | SEQ ID NO: 39 or 41 or 43 | SEQ ID NO: 49 or 50 |
| SEQ ID NO: 114 | SEQ ID NOs: 44 and 118 | SEQ ID NO: 39 or 41 or 43 | SEQ ID NO: 49 or 50 |
| SEQ ID NO: 115 | SEQ ID NOs: 44 and 118 | SEQ ID NO: 39 or 41 or 43 | SEQ ID NO: 49 or 50 |
| SEQ ID NO: 116 | SEQ ID NOs: 44 and 118 | SEQ ID NO: 39 or 41 or 43 | SEQ ID NO: 49 or 50 |
| SEQ ID NO: 117 | SEQ ID NOs: 44 and 118 | SEQ ID NO: 39 or 41 or 43 | SEQ ID NO: 49 or 50 |

Polynucleotides

In another aspect, the present disclosure provides isolated nucleic acid molecules comprising a polynucleotide encoding a hybrid soluble ActRIIB-ECD polypeptide of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding ActRIIB polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase. cDNA is obtained from libraries prepared from mRNA isolated from various tissues that express ActRIIB. The DNA molecules of the disclosure include full-length genes as well as polynucleotides and fragments thereof. The full-length gene may also include sequences encoding the N-terminal signal sequence.

Such nucleic acids may be used, for example, in methods for making the novel hybrid soluble ActRIIB-ECD polypeptides. In various embodiments, the polynucleotides encodes any one of the polypeptide sequences set forth in SEQ ID NOs: 3-37 or 51-117, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the polynucleotides encode a polypeptide having an amino acid sequence at least 80%, 85%, 90%, 95%, 96%, 97%, 98% or 99% identity to any one of the polypeptides sequences set forth in SEQ ID NOs: 3-37 or 51-117, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the polynucleotides encode a polypeptide having at least 90% identity to any one of the polypeptides sequences set forth in SEQ ID NOs: 3-37 or 51-117, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the polynucleotides encode a polypeptide having an amino acid sequence at least 95% identity to any one of the polypeptides sequences set forth in SEQ ID NOs: 3-37 or 51-117, wherein the hybrid ActRIIB-ECD polypeptide is capable of binding myostatin and activin A, but demonstrates a decreased binding affinity for BMP9 relative to a wild-type ActRIIB-ECD polypeptide. In various embodiments, the nucleic acid sequences of the present disclosure can be isolated, recombinant, and/or fused with a heterologous nucleotide sequence, or in a DNA library.

In various embodiments, the present disclosure provides nucleic acid molecules which hybridize under stringent or moderate conditions with the polypeptide-encoding regions of the polynucleotides described herein, wherein the encoded polypeptide comprises an amino acid sequence as set forth in SEQ ID NOs: 3-37 or 51-117 and wherein the encoded polypeptide is capable of binding myostatin and activin A, but demonstrates a decreased binding affinity for BMP9 relative to a wild-type ActRIIB-ECD polypeptide. One of ordinary skill in the art will understand readily that appropriate stringency conditions, which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In various embodiments, the recombinant nucleic acids of the present disclosure may be operably linked to one or more regulatory nucleotide sequences in an expression construct. Regulatory sequences are art-recognized and are selected to direct expression of the hybrid soluble ActRIIB-ECD polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding a hybrid soluble ActRIIB-ECD polypeptide and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding a hybrid soluble ActRIIB-ECD polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered. An exemplary expression vector suitable for expression of vActRIIB is the pDSRa, (described in WO 90/14363, herein incorporated by reference) and its derivatives, containing vActRIIB polynucleotides, as well as any additional suitable vectors known in the art or described below.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In various embodiments, a vector will be designed for production of the subject hybrid soluble ActRIIB-ECD polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject hybrid soluble ActRIIB-ECD polypeptides in cells propagated in culture, e.g., to produce proteins, including fusion proteins or variant proteins, for purification.

This present disclosure also pertains to a host cell transfected with a recombinant gene including a nucleotide sequence coding an amino acid sequence (e.g., SEQ ID NOs: 3-37 or 51-117) for one or more of the subject hybrid soluble ActRIIB-ECD polypeptide. The host cell may be any prokaryotic or eukaryotic cell. For example, a hybrid soluble ActRIIB-ECD polypeptide of the present disclosure may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject hybrid soluble ActRIIB-ECD polypeptides. For example, a host cell transfected with an expression vector encoding a hybrid soluble ActRIIB-ECD polypeptide can be cultured under appropriate conditions to allow expression of the hybrid soluble ActRIIB-ECD polypeptide to occur. The hybrid soluble ActRIIB-ECD polypeptide may be secreted and isolated from a mixture of cells and medium containing the hybrid soluble ActRIIB-ECD polypeptide. Alternatively, the hybrid soluble ActRIIB-ECD polypeptide may be retained cytoplasmically or in a membrane fraction and the cells harvested, lysed and the protein isolated. A cell culture includes host cells, media and other byproducts. Suitable media for cell culture are well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Compositions

In another aspect, the present disclosure provides a pharmaceutical composition comprising the isolated hybrid soluble ActRIIB polypeptides or hybrid ActRIIB ligand trap proteins in admixture with a pharmaceutically acceptable carrier. Such pharmaceutically acceptable carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature.

For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

When parenteral administration is contemplated, the therapeutic pharmaceutical compositions may be in the form of a pyrogen-free, parenterally acceptable aqueous solution comprising the desired ActRIIB polypeptide in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions.

In various embodiments, the therapeutic pharmaceutical compositions may be formulated for targeted delivery using a colloidal dispersion system. Colloidal dispersion systems include macromolecule complexes, nanocapsules, microspheres, beads, and lipid-based systems including oil-in-water emulsions, micelles, mixed micelles, and liposomes. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In various embodiments, oral administration of the pharmaceutical compositions is contemplated. Pharmaceutical compositions that are administered in this fashion can be formulated with or without those carriers customarily used in the compounding of solid dosage forms such as tablets and capsules. In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming, and preservative agents.

In various embodiments, topical administration of the pharmaceutical compositions, either to skin or to mucosal membranes, is contemplated. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the disclosure (e.g., a hybrid ActRIIB ligand trap), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Additional pharmaceutical compositions contemplated for use herein include formulations involving polypeptides in sustained- or controlled-delivery formulations. Techniques for formulating a variety of other sustained- or controlled-delivery means, such as liposome carriers, bioerodible microparticles or porous beads and depot injections, are also known to those skilled in the art.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In various embodiments, the present disclosure provides a method for treating muscle wasting in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating bone disorders in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating metabolic disorders in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating fibrosis in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating autoimmune/inflammatory disease in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating cardiovascular disease in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating cancer cells in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating renal disease in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating arthritis in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating anorexia in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating liver disease in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method of inducing stem cell growth for tissue repair or organ regeneration in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide which having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating anemia in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating pain in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

In various embodiments, the present disclosure provides a method for treating aging in a subject, comprising administering to the subject a therapeutically effective amount of a hybrid ActRIIB ligand trap in admixture with a pharmaceutically acceptable carrier, wherein the hybrid ActRIIB ligand trap comprises a soluble ActRIIB-ECD polypeptide having an amino acid sequence selected from the group consisting of SEQ ID NO: 16 and SEQ ID NO: 29. In various embodiments, a linker having the amino acid sequence set forth in SEQ ID NO: 44 is used with a hinge linker having the amino acid sequence set forth in SEQ ID NO: 118 to link a human IgG4 Fc (SEQ ID NO: 43) to the hybrid soluble ActRIIB-ECD polypeptide of the pharmaceutical composition.

The following examples are offered to more fully illustrate the disclosure, but are not construed as limiting the scope thereof.

EXAMPLE 1

The polypeptides of the present disclosure can be prepared according to recombinant DNA techniques that are well known to those of skill in the art. In this example, the preparation of the hybrid soluble ActRIIB-ECD polypeptides is generally described.

Various hybrid ActRIIB-ECD polypeptides were designed by substituting multiple amino acid residues at selective positions within the human ActRIIB extracellular domain with amino acid residues derived from the human ActRIIA extracellular domain at corresponding positions based on sequence alignment at the amino acid level. DNA expression cassettes encoding the hybrid ActRIIB-ECD polypeptides were generated by using site-directed mutagenesis and subsequently engineered into Fc fusion protein constructs by placing in frame a cDNA fragment encoding human immunoglobulin light chain signal peptide at the 5' end and a DNA fragment encoding a peptide linker followed by human Fc at the 3' end.

EXAMPLE 2

In this example, the preparation of the hybrid ActRIIB ligand trap proteins configured as depicted in FIG. 1 is generally described.

Synthetic DNA cassettes encoding various hybrid ActRIIB ligand trap proteins, each containing a signal peptide leader sequence (SEQ ID NO: 49 or 50), a hybrid soluble ActRIIB-ECD polypeptide from Example 1 (or a wild-type ActRIIB-ECD sequence), a peptide linker sequence (SEQ ID NO: 44), a hinge linker sequence (SEQ ID NO: 118) and an Fc domain sequence (SEQ ID NO: 39 or 41 or 43), are cloned into Freedom pCHO 1.0 and pcDNA3.1 expression vectors (Life Technologies).

For stable transfection, the pCHO 1.0 expression vectors encoding the various hybrid ActRIIB ligand trap proteins were each transfected in CHO-S cells using FreeStyle MAX Reagent (Life Technologies). 48 hours after transfection, the cells were grown in serum-free CD FortiCHO medium containing puromycin and methotrexate (MTX) selection for 3-7 weeks at 37° C. in a shaker $CO_2$ incubator. The stable pool were generated until cells exceed 90% viability containing 30 M puromycin and 500 nM methotrexate. Stable clones were generated by dilution cloning following the manufacturer's recommended protocols (Life Technologies). For transient transfection, pcDNA3.1 expression plasmids encoding various hybrid ActRIIB ligand trap proteins were each transfected in Expi293 cells using Expri-Fectamine293 transfection reagent (Life Technologies).

Following transfection, stably transfected CHO-S cells were grown in completed serum-free CD FortiCHO medium supplied with glucose at 37° C. in a $CO_2$ shaker incubator for up to 14 days. The conditioned medium was collected for protein purification. Transiently transfected Expi293 cells were cultured in Expi293 expression medium at 37° C. in a $CO_2$ shaker incubator for up to 7 days and the medium was collected for protein purification.

For purification, condition medium containing the hybrid ActRIIB ligand trap protein was purified via a Hitrap Protein A High Performance Column by using AKTA FPLC (GE Healthcare). The hybrid ActRIIB ligand trap proteins were eluted with acetic acid buffer (pH 3.6), neutralized with 1 M Tris-HCl (pH 8.0), and then subjected to buffer-exchange. Protein concentrations were determined by using a spectrophotometer (Beckman).

EXAMPLE 3

In this example, the myostatin and BMP9 binding activities of seven of the hybrid ActRIIB ligand trap proteins is evaluated.

Myostatin and BMP9 binding activities of various hybrid ActRIIB ligand trap proteins were initially analyzed using Octect Red (ForteBio). Purified proteins or conditioned media were individually loaded to AHC biosensors with maximum loading. Following a baseline washing phase, the sensors were exposed to 10 nM myostatin or BMP9, respectively, for an association step followed by a dissociation step. All experiments were performed with shaking at 1,000 rpm. Binding activity was analyzed using ForteBio's software with KD being calculated using the ratio Kd/Ka.

Results

Hybrid ActRIIB ligand trap proteins were examined in comparison with the wild-type ActRIIB-ECD-Fc fusion protein for binding activities against myostatin and BMP9. The results indicate that the hybrid ActRIIB ligand trap proteins exhibit a marked reduction in binding affinity to BMP9 as compared to the wild-type ActRIIB-ECD-Fc fusion protein. A number of the hybrid ActRIIB ligand trap proteins showed dramatically decreased BMP9 binding affinities that are more than 100-fold weaker than that of the wild-type ActRIIB-ECD-Fc protein and in the meantime, they retained a strong myostatin binding affinity that is similar to that of the wild-type ActRIIB-ECD-Fc protein. A summary of the preliminary binding data obtained by Octet Red analysis is shown in Table 3.

TABLE 3

| ActRIIB-ECD-polypeptide | Myostatin Binding | BMP9 Binding |
|---|---|---|
| Wild-type | +++ | +++ |
| AG-0003 (SEQ ID NO: 5) | +++ | ++ |
| AG-0005 (SEQ ID NO: 7) | +++ | + |
| AG-0006 (SEQ ID NO: 8) | +++ | + |
| AG-0007 (SEQ ID NO: 9) | +++ | + |
| AG-0008 (SEQ ID NO: 10) | +++ | ++ |
| AG-0014 (SEQ ID NO: 16) | +++ | N.D. |
| AG-0027 (SEQ ID NO: 29) | +++ | N.D. |

+++ KD <$10^{-8}$M
++ KD: $10^{-6}$-$10^{-7}$M
+ KD $10^{-4}$-$10^{-6}$M
N.D. No detectable binding AG-0014 and AG-0027 were analyzed by kinetic exclusion assay (KinExA) (Sapidyne Instruments, Inc.). 20-30 µg/ml of myostatin, activin A or BMP-9 was separately coupled to NHS-Activated Sepharose 4 Fast Flow beads (GE Healthcare) using experimental procedures recommended by Sapidyne Instruments. The concentration for each hybrid ActRIIB ligand trap protein was held constant as the ligand was titrated in a 2.5-fold serial dilution. Solutions were allowed to reach equilibrium by incubation at room temperature up to 24 hours and subsequently passed through a flow cell pre-packed with ligand-coated Sepharose beads on a KinExA 3000 machine (Sapidyne Instruments). The free hybrid ActRIIB ligand trap proteins captured on the beads was detected by Alexa Fluor 647-labeled goat anti-human-Fc antibody (Jackson ImmunoResearch Laboratories, Inc.). The ligand binding affinity values ($K_D$) were calculated using the KinExA Pro software (Sapidyne Instruments).

Results

A summary of the preliminary binding data obtained by KinExA analysis is shown in Table 4. The data indicate that similar to wild-type ActRIIB-Fc, the two exemplary hybrid ActRIIB ligand trap proteins have high affinities for both myostatin and activin A at the single-digit pM range. However, the two hybrid ActRIIB ligand trap proteins show no detectable binding to BMP9, in contrast to the wild-type ActRIIB-Fc which displays a strong binding affinity to BMP9 at the single-digit pM range.

TABLE 4

| Molecule | Myostatin $K_D$ (pM) | Activin A $K_D$ (pM) | BMP9 $K_D$ (pM) |
|---|---|---|---|
| WT ActRIIB-Fc | 5.06 pM | 1.38 pM | 4.25 pM |
| AG-0014 (SEQ ID NO: 16) | 8.75 pM | 0.357 pM | No binding |
| AG-0027 (SEQ ID NO: 29) | 7.87 pM | 1.09 pM | No binding |

EXAMPLE 4

In this example, a myostatin/activin A signaling assay and a BMP9 signaling assay are described which were used to quantify the myostatin/activin A-blocking activities, and BMP9-blocking activity, respectively, of the hybrid ActRIIB ligand trap proteins.

To evaluate myostatin/activin A signaling, a reporter construct with 12 repeats of CAGA sequence (Dennler et al, EMBO 17: 3091-3100, 1998) was cloned into a pGL3-luc reporter vector (Promega). The engineered pGL3-CAGA$_{12}$-luc vector was stably transfected in C2C12 cells to generate a luciferase reporter cell line, C2C12-CAGA-luc, capable of sensing Smad3/4 signaling mediated by myostatin or activin A. To measure myostatin- and activin A-neutralizing activities, 4 nM of recombinant myostatin or activin A was preincubated with increasing concentrations of various hybrid ActRIIB ligand trap proteins as well as a wild-type ActRIIB-ECD-Fc fusion protein (as a control) for 1 hour at room temperature. Subsequently, the reaction mixtures were added to the C2C12-CAGA-luc cell cultures. After incubation for 5 hours in $CO_2$ incubator at 37° C., the luciferase activities of the C2C12-CAGA-luc reporter cultures were measured by using LuminoSkan Ascent (Thermo Scientific).

BMP9 signaling was tested in C2C12 cells that had been stably transfected with a luciferase reporter containing BMP responsive element (BRE) that senses Smad1/5/8-signaling (Korchynski et. al, J. Biol. Chem. 277:4883-4891, 2002). Specifically, a two-repeat BMP-responsive element (Briter et at, PLoS One, 2012) was synthesized and cloned into the pGL3-luc vector (Promega). The pGL3-2XBRE-luc vector was then stably transfected into C2C12 cells. A stably transfected reporter cell line, C2C12-BRE-luc, was used to quantify the BMP9-mediated Smad1/5/8 signaling. To measure the BMP-neutralizing activity, 4 nM of BMP9 was preincubated with increasing concentrations of various hybrid ActRIIB ligand trap proteins as well as a wild-type ActRIIB-ECD-Fc fusion protein (as a control) for 1 hour at room temperature. The reaction mixtures were then added to the C2C12-BRE-luc cell cultures. After 5 hours of incubation at 37° C. in a CO2 incubator, the luciferase activities of the C2C12 BRE-luc reporter cultures were measured by using Luminoskan Ascent (Thermo Scientific).

Results

Figure 2:
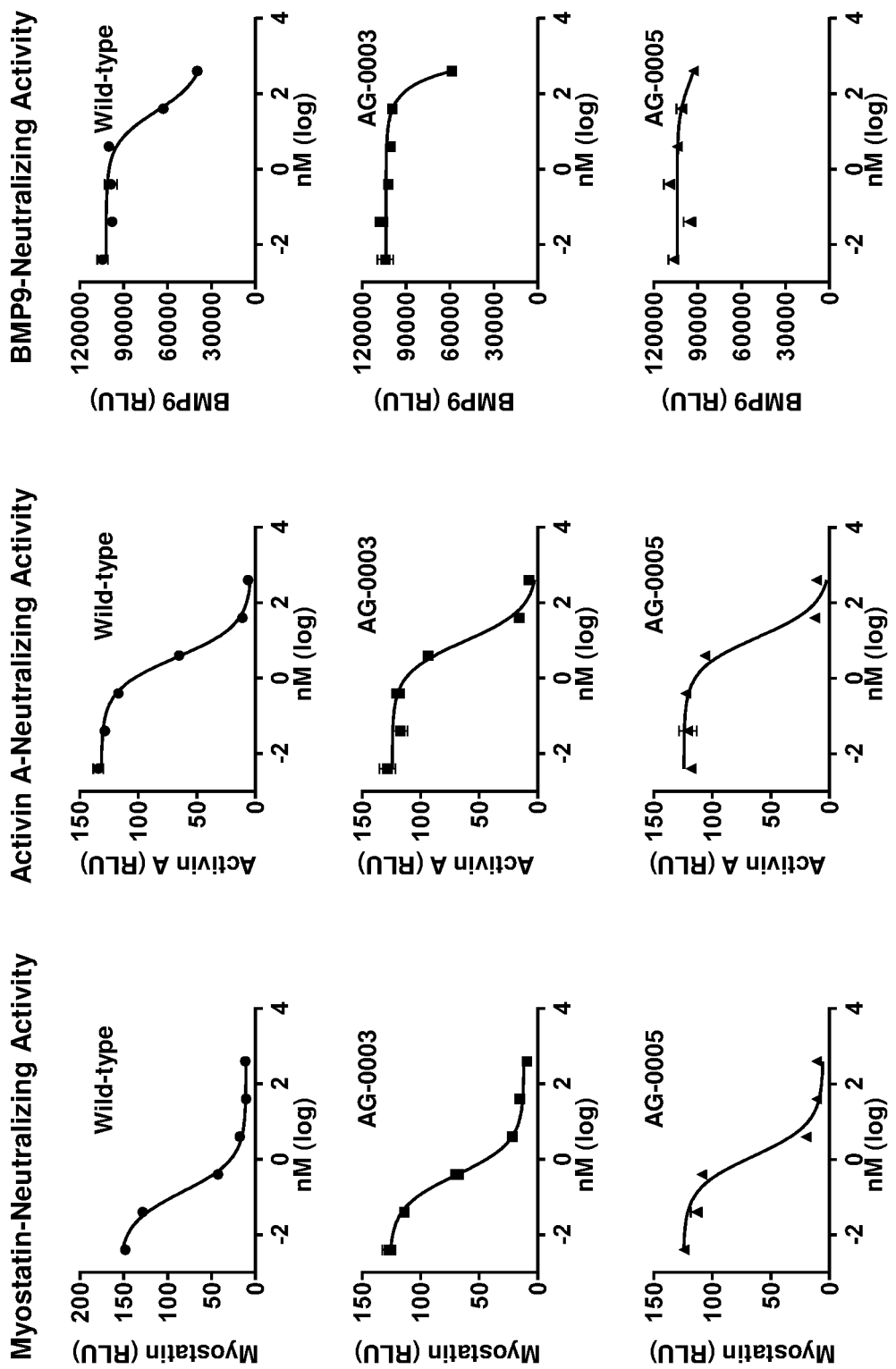
FIG. 2 shows line graphs depicting the results of the cell-based assays used to evaluate the myostatin-neutralizing (left panels), activin A-neutralizing (middle panels), and BMP9-neutralizing (right panels) abilities for the hybrid ActRIIB ligand trap protein having the amino acid sequence of AG-0003 (SEQ ID NO: 5) and the hybrid ActRIIB ligand trap protein having the amino acid sequence of AG-0005 (SEQ ID NO: 7), in comparison to those of the wild-type ActRIIB-Fc protein as a benchmark (WT).

The results revealed that in comparison to the wild-type ActRIIB-ECD-Fc fusion protein, two exemplary hybrid ActRIIB ligand trap proteins retained strong myostatin- and activin A-neutralizing activities but had marked reductions in BMP9-neutralizing activity (see FIG. 2). FIG. 2 shows the cell-based neutralizing activities against myostatin, activin A and BMP9 for two exemplary hybrid ActRIIB ligand trap proteins, AG-0003 (SEQ ID NO: 5) and AG-0005 (SEQ ID NO: 7), in comparison to those of the wild-type control ActRIIB-ECD-Fc fusion protein.

EXAMPLE 5

In this Example, the myostatin/activin A signaling assay and BMP9 signaling assay described in Example 4 were used to quantify the myostatin/activin A-blocking activities, and BMP9-blocking activity, respectively, of the following hybrid ActRIIB ligand trap protein: AG-0003 (SEQ ID NO: 5), AG-0014 (SEQ ID NO: 16), AG-0023 (SEQ ID NO: 25), AG-0024 (SEQ ID NO: 26), AG-0025 (SEQ ID NO: 27), AG-0027 (SEQ ID NO: 29), AG-0028 (SEQ ID NO: 30), AG-0029 (SEQ ID NO: 31), and AG-0035 (SEQ ID NO: 37).

Results

Figure 3:
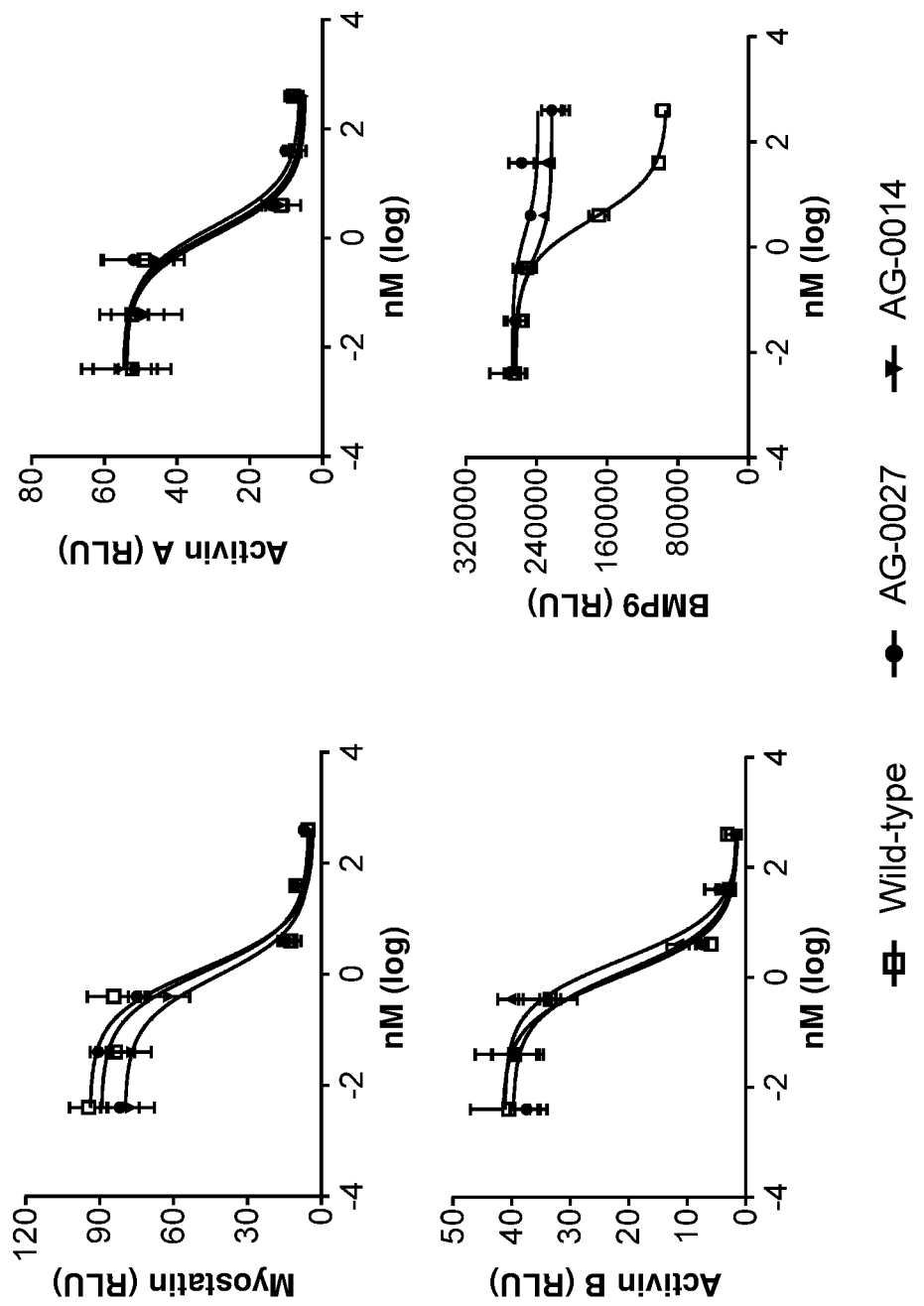
FIG. 3 shows line graphs depicting the results of the cell-based neutralizing activities on myostatin (top left), activin A (top right), activin B (bottom left) and BMP9 (bottom right) for the hybrid ActRIIB ligand trap protein having the amino acid sequence of AG-0014 (SEQ ID NO: 16) and the hybrid ActRIIB ligand trap protein having the amino acid sequence of AG-0027 (SEQ ID NO: 29) in comparison to those of the wild-type ActRIIB-Fc protein as a benchmark (WT). Myostatin-, activin A- and activin B-neutralizing activities were examined by using C2C12-CAGA-luc reporter assay and BMP9-neutralizing activities were analyzed by using C2C12-BRE-luc reporter assay as described in the Examples.

The results revealed that in comparison to the wild-type ActRIIB-ECD-Fc fusion protein, several of these hybrid ActRIIB ligand trap proteins retained strong myostatin- and activin A-neutralizing activities but had marked reductions in BMP9-neutralizing activity. FIG. 3 shows the cell-based neutralizing activities against myostatin, activin A and BMP9 for two exemplary hybrid ActRIIB ligand trap proteins, AG-0014 and AG-0027, in comparison to those of the wild-type control ActRIIB-ECD-Fc fusion protein.

Figure 10:
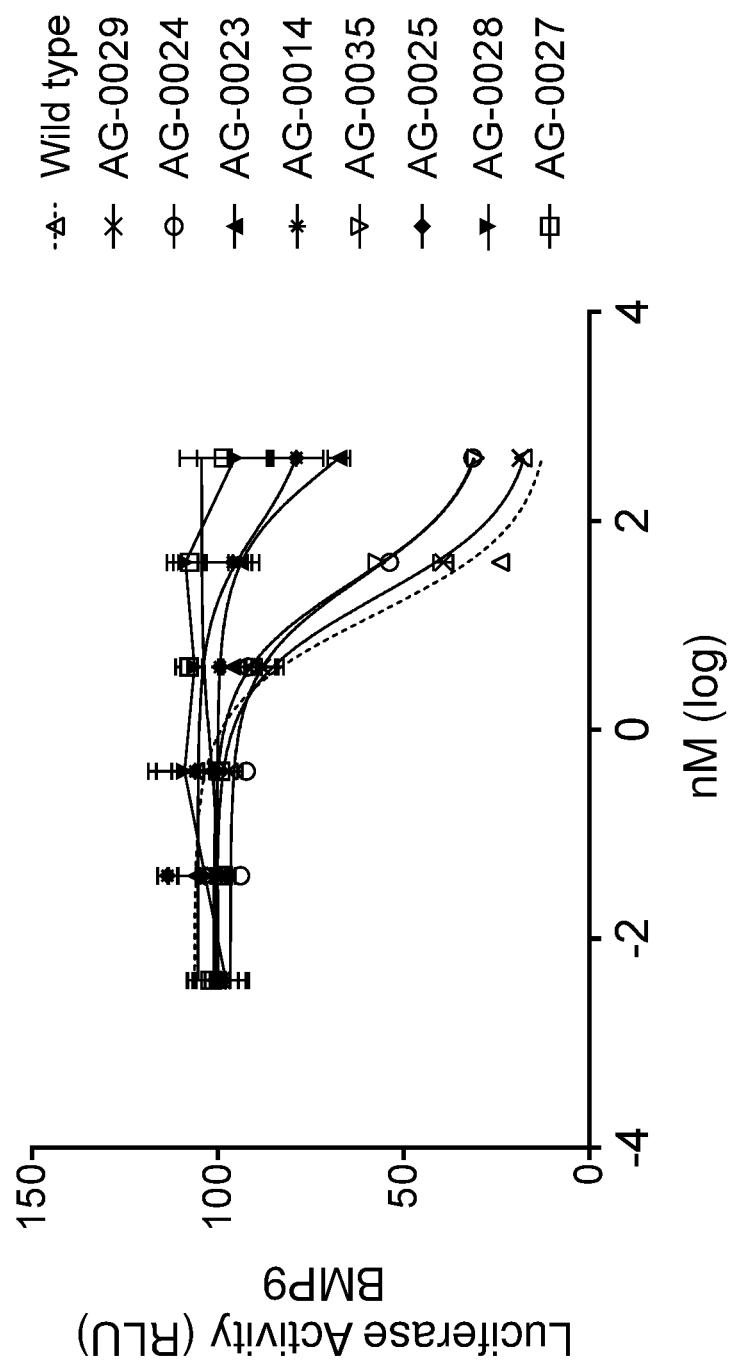
FIG. 10 shows line graphs depicting the results of the cell-based neutralizing activities on BMP9 for a number of exemplary hybrid ActRIIB ligand trap proteins including AG-0014 (SEQ ID NO: 16), AG-0023 (SEQ ID NO: 25), AG-0024 (SEQ ID NO: 26), AG-0025 (SEQ ID NO: 27), AG-0027 (SEQ ID NO: 29), AG-0028 (SEQ ID NO: 30), AG-0029 (SEQ ID NO: 31) and AG-0035 (SEQ ID NO: 37) in comparison to those of the wild-type ActRIIB-Fc protein as a benchmark (Wild type). BMP9-neutralizing activities were analyzed by using C2C12-BRE-luc reporter assay.
Figure 11:
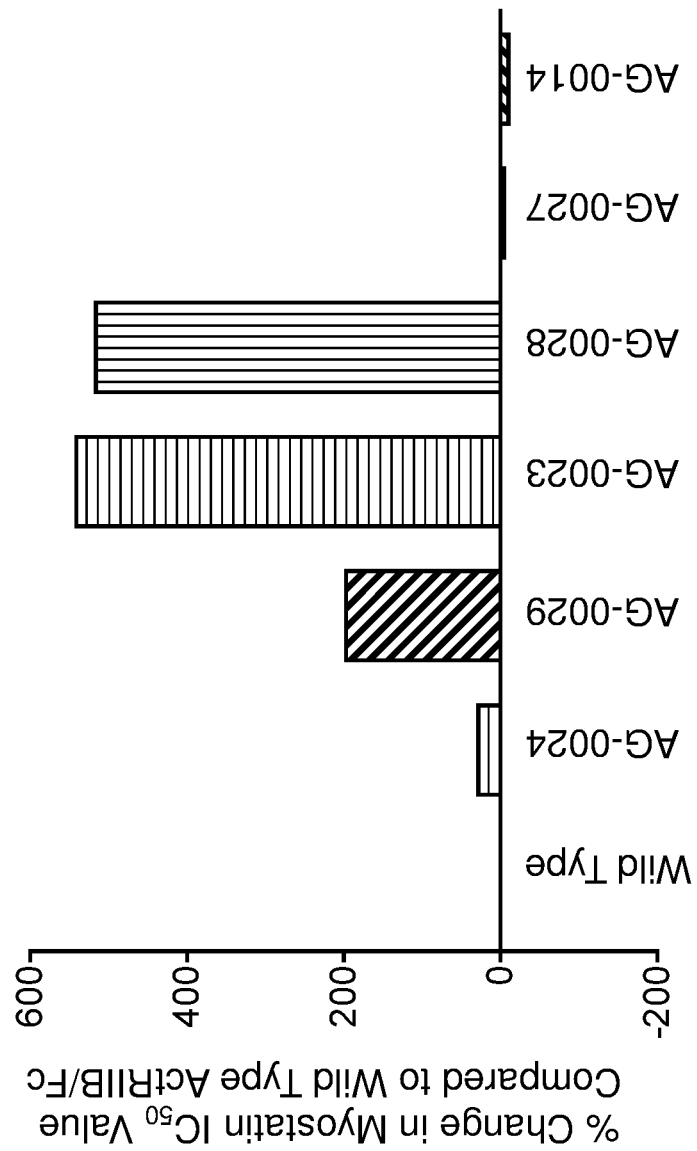
FIG. 11 illustrates the differences in myostatin-neutralizing $IC_{50}$ values between several exemplary hybrid ActRIIB ligand trap proteins relative to that of the wild type ActRIIB-Fc protein. Myostatin-neutralizing activities of the individual proteins were examined using C2C12-CAGA-luc reporter cultures and the $IC_{50}$ values were calculated by using Prism software. The graph shows the percentage difference in myostatin-neutralizing $IC_{50}$ value of each of the exemplary hybrid ActRIIB ligand trap proteins, including AG-0014 (SEQ ID NO: 16), AG-0023 (SEQ ID NO: 25), AG-0024 (SEQ ID NO: 26), AG-0027 (SEQ ID NO: 29), AG-0028 (SEQ ID NO: 30) and AG-0029 (SEQ ID NO: 31), compared to that of the wild-type ActRIIB-Fc.

And as shown in Tables 5 and 6, in comparison to the wild-type ActRIIB-ECD-Fc fusion protein (WT ActRIIB-Fc), various exemplary hybrid ActRIIB ligand trap proteins showed dramatically reduced BMP9-neutralizing activity in cell-based Smad1/5/8 BRE-luc reporter assay, while retaining strong neutralizing activities against myostatin, activin A and activin B in cell-based Smad2/3 CAGA-luc reporter assay. Table 5 shows the $IC_{50}$ values on cell-based neutralization against myostatin, activin A, activin B and BMP9 of AG-0014 and AG-0027, respectively, in comparison to those of WT ActRIIB-Fc. Table 6 outlines the BMP9- and myostatin-neutralizing activities of several exemplary hybrid ActRIIB ligand trap proteins in comparison to those of WT ActRIIB-Fc. Compared to WT ActRIIB-Fc, hybrid proteins AG-0003, AG-0004, AG-0005, AG-0014, AG-0023, AG-0024, AG-0025, AG-0027 and AG-0028 showed dramatically reduced or virtually no BMP9-neutralizing activity (also see FIG. 10); AG-0003, AG-0005, AG-0014 and AG-0027 retained full myostatin-neutralizing activity, whereas AG-0004, AG-0023, AG-0024, AG-0025 and AG-0028 exhibited a loss in myostatin-neutralizing activity (also see FIG. 11). Overall, these results demonstrate an ability of various hybrid ActRIIB ligand trap proteins to preferentially block myostatin/activin-mediated Smad2/3 signaling with minimal or no impact on BMP9-mediated Smad1/5/8 signaling.

TABLE 5

| | Cell-Based $IC_{50}$ (nM) | | | |
|---|---|---|---|---|
| | Against Myostatin | Against Activin A | Against Activin B | Against BMP9 |
| WT ActRIIB-Fc (SEQ ID NO: 1) | 1.24 | 1.27 | 1.04 | 3.40 |
| AG-0014 (SEQ ID NO: 16) | 0.95 | 1.15 | 2.10 | N.D. |
| AG-0027 (SEQ ID NO: 29) | 1.14 | 1.62 | 1.30 | N.D. |

N.D.: No detectable neutralizing activity

TABLE 6

| | ActRIIB Extracellular Domain Mutation | BMP9-Neutralizing Activity | Myostatin-Neutralizing Activity |
|---|---|---|---|
| WT ActRIIB-Fc (SEQ ID NO: 1) | Wild-type | ++++ | ++++ |
| AG-0003 (SEQ ID NO: 5) | F58I + Q64T + E65D + A68E + T69K + E70K + E71D + N72S + Q74E | +/− | ++++ |
| AG-0004 (SEQ ID NO: 6) | F58I + Q64T + E65D + A68E + T69K + E70K + E71D + N72S | +/− | ++ |
| AG-0005 (SEQ ID NO: 7) | Q64T + E65D + A68E + T69K + E70K + E71D + N72S | − | ++++ |
| AG-0007 (SEQ ID NO: 9) | A68E + T69K + E70K + E71D + N72S + Q74E | +++ | ++ |
| AG-0008 (SEQ ID NO: 10) | A68E + T69K + E70K + E71D + N72S | +++ | +++ |
| AG-0014 (SEQ ID NO: 16) | E26Y + E28D + Q29K + L33R | −/+ | ++++ |
| AG-0027 (SEQ ID NO: 29) | E28D + F58I + E70K | − | ++++ |
| AG-0029 (SEQ ID NO: 31) | E28D | +++ | ++ |
| AG-0024 (SEQ ID NO: 26) | F58I | +++ | ++++ |
| AG-0023 (SEQ ID NO: 25) | E70K | − | + |
| AG-0028 (SEQ ID NO: 30) | E28D + E70K | − | + |
| AG-0025 (SEQ ID NO: 27) | F58I + E70K | − | +++ |
| AG-0035 (SEQ ID NO: 37) | E28D + F58I | +++ | +++ |

++++: Full neutralizing activity;
+++: Partial neutralizing activity;
++: Weak neutralizing activity;
+: Very weak neutralizing activity;
+/−: Little or no neutralizing activity;
−: No neutralizing activity

EXAMPLE 6

Figure 4:
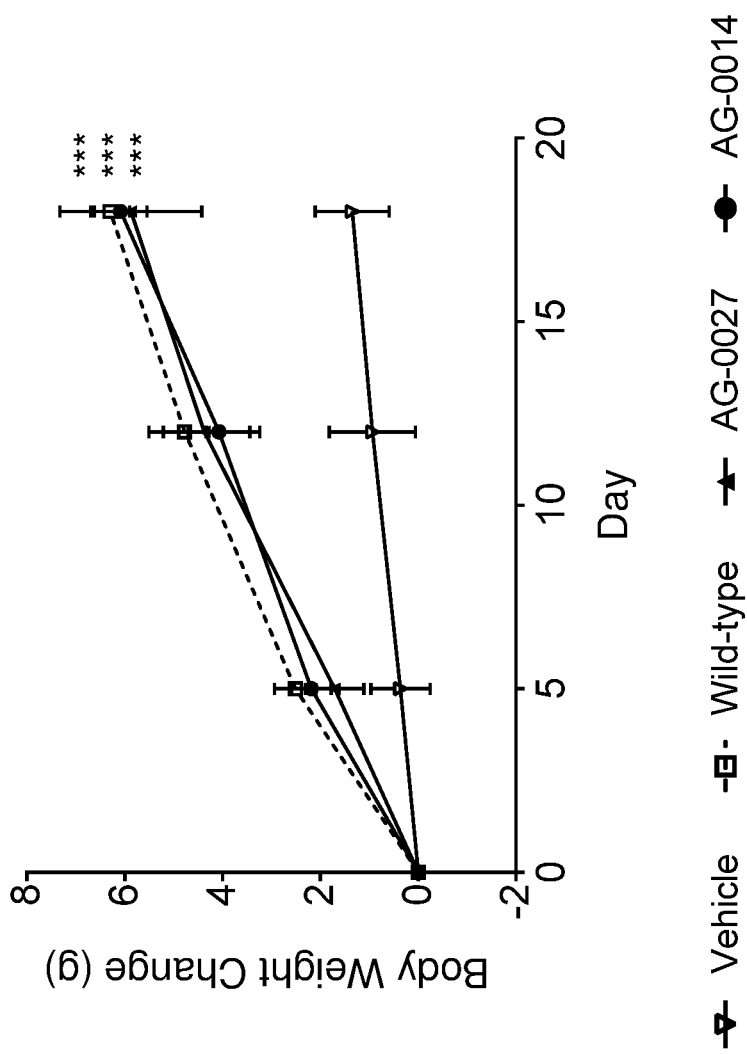
FIG. 4 shows line graphs depicting the effects on body weight in 9-week-old male C57Bl/6 mice subcutaneously injected with PBS (Vehicle), wild-type ActRIIB-Fc (WT), AG-0014 (SEQ ID NO: 16) and AG-0027 (SEQ ID NO: 29), respectively, at the dosage of 10 mg/kg, once per week. Body weights were recorded at day 0, day 5, day 12 and day 18. n=6/8 per group. Student's t-test was performed for statistical analysis. ***: P<0.001 vs. Vehicle group.
Figure 5:
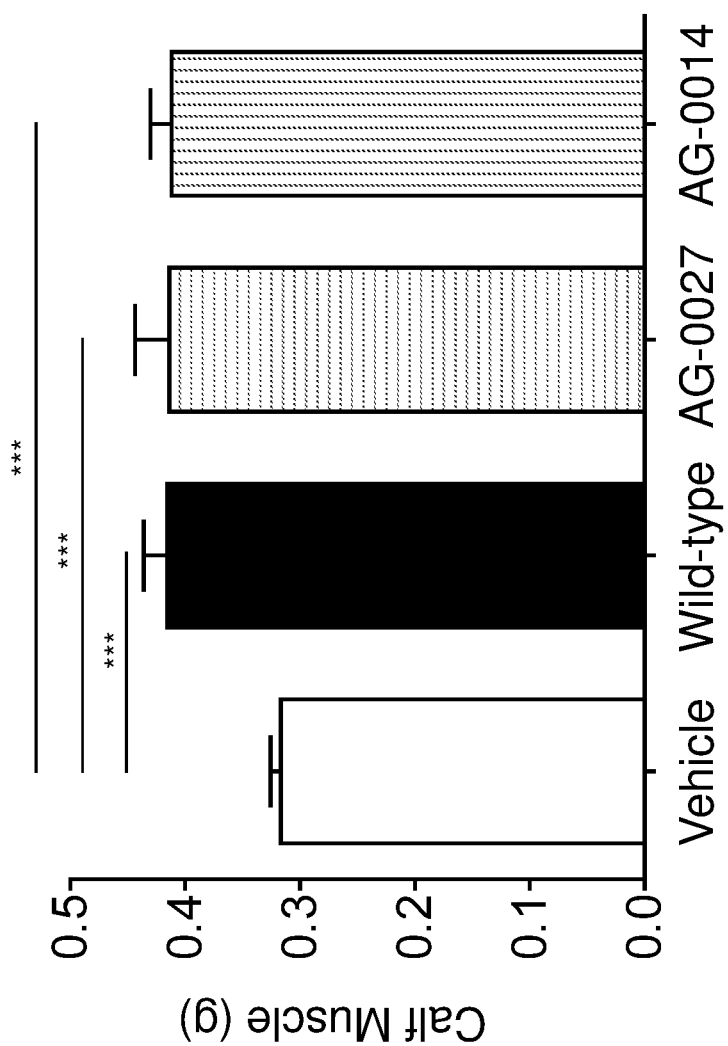
FIG. 5 is a bar graph depicting the effects on muscle mass in 9-week-old male C57Bl/6 mice subcutaneously injected with PBS (Vehicle), wild-type ActRIIB-Fc (WT), AG-0014 (SEQ ID NO: 16) and AG-0027 (SEQ ID NO: 29), respectively, at the dosage of 10 mg/kg, once per week (n=6/8 per group). Individual calf muscles from each animal were dissected and weighed during terminal necropsy. Statistical analysis was performed by Student's t-test. ***: P<0.001 vs. Vehicle group.

In this Example, the effects on body weight and muscle mass in 9-week-old male C57Bl/6 mice subcutaneously injected with PBS (Vehicle), wild-type ActRIIB-Fc, AG-0014 (SEQ ID NO: 16) and AG-0027 (SEQ ID NO: 29), respectively, at the dosage of 10 mg/kg, once per week were evaluated. Body weights were recorded at day 0, day 5, day 12 and day 18. n=6/8 per group. The values for body weight change are calculated as percentage of weight increase from the baseline at day 0. Individual calf muscles from each animal were dissected and weighed during terminal necropsy. The values are expressed as percent increase of the average calf muscle mass in each treatment group compared to that of the vehicle group. As depicted in FIGS. 4 and 5 and Table 7, administration of each of the two exemplary hybrid ligand trap proteins is capable of markedly increasing body weight gain in the mice, in a similar manner as wild type ActRIIB-Fc.

TABLE 7

Body Weight Increase from Baseline

| Groups | Day 5 | Day 12 | Day 18 |
|---|---|---|---|
| Vehicle | 1.5% | 3.9% | 5.6% |
| WT ActRIIB-Fc | 9.4% | 20.1% | 25.8% |
| AG-0014 | 9.0% | 16.8% | 25.2% |
| AG-0027 | 7.1% | 18.1% | 24.3% |

As depicted in FIG. 5 and Table 8, administration of the two exemplary hybrid ligand trap proteins AG-0014 and AG-0027, respectively, is capable of markedly increasing muscle mass in the mice in a similar manner as wild type ActRIIB-Fc.

TABLE 8

Muscle Mass Increase Compared to Vehicle

| Groups | Increase in Calf Muscle Mass Compared to Vehicle |
|---|---|
| WT ActRIIB-Fc | 31.3% |
| AG-0014 | 30.0% |
| AG-0027 | 30.7% |

EXAMPLE 7

Figure 6:
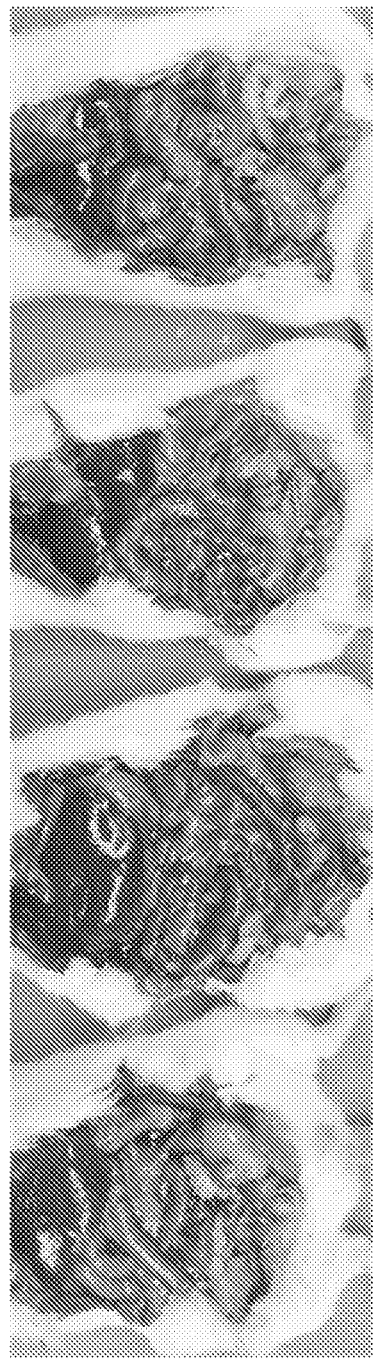
FIG. 6 shows Evans blue vascular permeability test images of mouse abdominal cavity. Representative images of surgically exposed abdominal cavity of each group are shown as labeled in the figure. 8-week-old male BalbC mice were treated with PBS (Vehicle), wild-type ActRIIB-Fc (WT), AG-0014 (SEQ ID NO: 16) and AG-0027 (SEQ ID NO: 29), respectively, at the dosage of 10 mg/kg, once per week. Two weeks after treatment, 200 µl of Evans blue dye (0.5% in PBS, pH7.2) was injected into each group of animals (n=4) via the tail vein. Necropsy was performed at 90 min after Evans blue dye injection.
Figure 7:
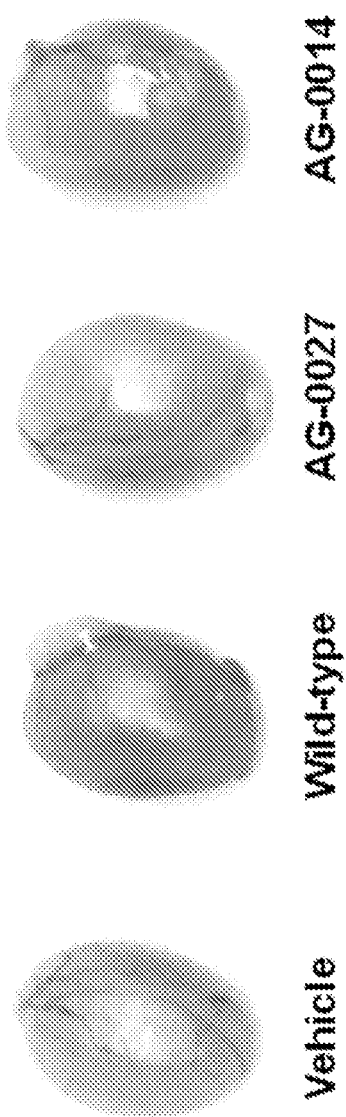
FIG. 7 shows Evans blue vascular permeability test images of mouse testis. Representative images of the dissected testis organ from each group are shown as labeled in the figure. 8-week-old male BalbC mice were treated with PBS (Vehicle), wild-type ActRIIB-Fc (WT), AG-0014 (SEQ ID NO: 16) and AG-0027 (SEQ ID NO: 29), respectively, at 10 mg/kg, once per week. Two weeks after treatment, 200 µl of Evans blue dye (0.5% in PBS, pH7.2) was injected into each group of animals (n=4) via the tail vein. Necropsy was performed at 90 min post Evans blue dye injection.
Figure 8:
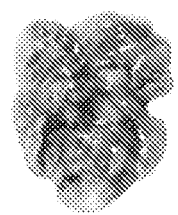
FIG. 8 shows Evans blue vascular permeability test images of mouse lung. Representative images of the dissected lung tissues from each group are shown as labeled in the figure. 8-week-old male BalbC mice were treated with PBS (Vehicle), wild-type ActRIIB-Fc (WT), AG-0014 (SEQ ID NO: 16) and AG-0027 (SEQ ID NO: 29), respectively, at 10 mg/kg, once per week. Two weeks after treatment, 200 µl of Evans blue dye (0.5% in PBS, pH7.2) was injected into each group of animals (n=4) via the tail vein. Necropsy was performed at 90 min after Evans blue dye injection.
Figure 8:
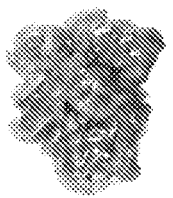
Figure 8:
Figure 8:
Figure 9:
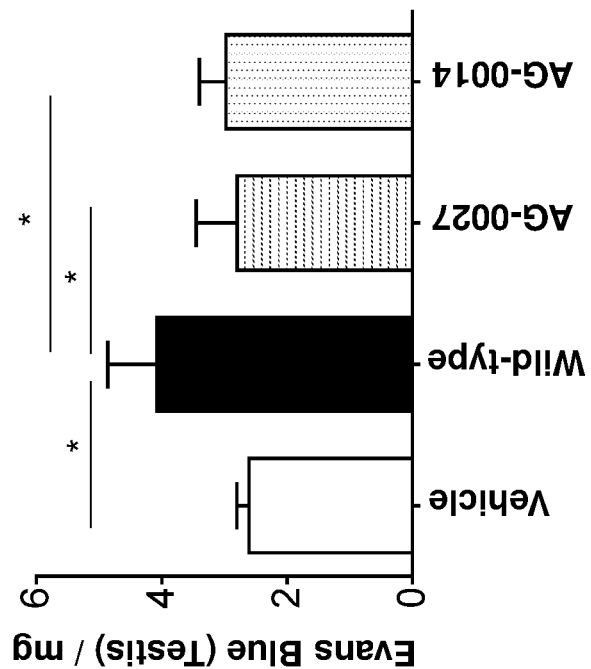
FIG. 9 shows bar graphs depicting the amounts of extravasated Evans blue dye per mg of wet lung tissue (left panel) and testis tissue (right panel) in different treatment groups as labeled in the figure. 8-week-old male BalbC mice were treated with PBS (Vehicle), the wild-type ActRIIB-Fc protein (WT), AG-0014 (SEQ ID NO: 16) and AG-0027 (SEQ ID NO: 29), respectively, at 10 mg/kg, once per week. Two weeks after treatment, 200 µl of Evans blue dye (0.5% in PBS, pH7.2) was injected into each group of animals (n=4) via the tail vein. Necropsy was performed at 90 min after Evans blue dye injection to collect testis and lung tissues. The tissues were weighed and then placed individually into vials containing formamide to extract the Evans blue dye. After incubation at 55° C. for 24 hours, the samples were centrifuge and the absorbance of the aqueous phase of each sample was measured at the wavelength of 610 nm using a spectrophotometer. Statistical analysis was performed by using Student's t-test. *: P<0.05.
Figure 9:
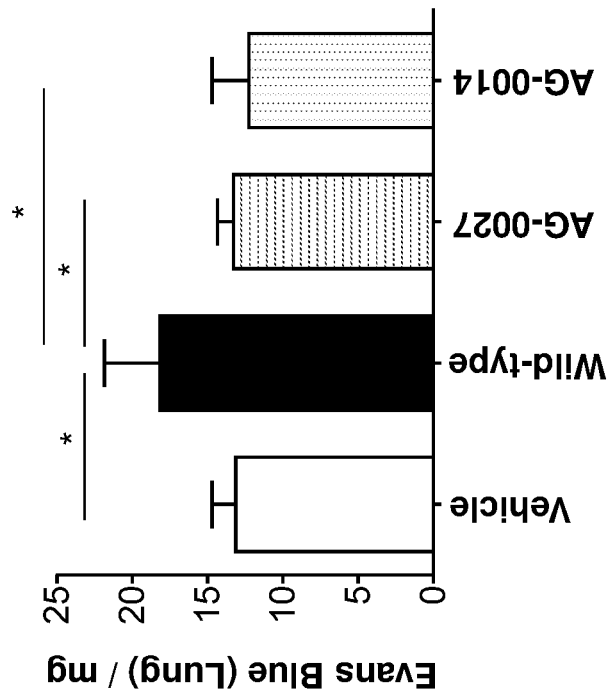

In this Example, the effects on Evans blue permeability in mouse abdominal cavity, mouse testis, and mouse lung tissues in 8-week-old male BalbC mice treated with PBS (Vehicle), wild-type ActRIIB-Fc, AG-0014 (SEQ ID NO: 16) and AG-0027 (SEQ ID NO: 29), respectively, at the dosage of 10 mg/kg, once per week, were evaluated. Two weeks after treatment, 200 µl of Evans blue dye (0.5% in PBS, pH7.2) was injected into each group of animals (n=4) via the tail vein. Necropsy was performed at 90 min after Evans blue dye injection. Representative images of surgically exposed abdominal cavity, dissected testis organ, and dissected lung tissue of each group are shown as labeled in FIGS. 6-8, respectively. Blue color indicates the leakage of blood vessel. Testis and lung tissues were weighed and then placed individually into vials containing formamide to extract the Evans blue dye. After incubation at 55° C. for 24 hours, the samples were centrifuged. The absorbance of the aqueous phase of each sample was measured at the wavelength of 610 nm using a spectrophotometer. The amounts of extravasated Evans blue dye per mg of wet lung tissue (left panel) and testis tissue (right panel) in different treatment groups are shown in FIG. 9.

Importantly, as depicted in FIGS. 6-9, administration of the two exemplary hybrid ligand trap proteins markedly decreases the level of blood vessel leakage as compared to wild type ActRIIB-Fc protein in all tissues evaluated in the treated animals.

EXAMPLE 8

Figure 12:
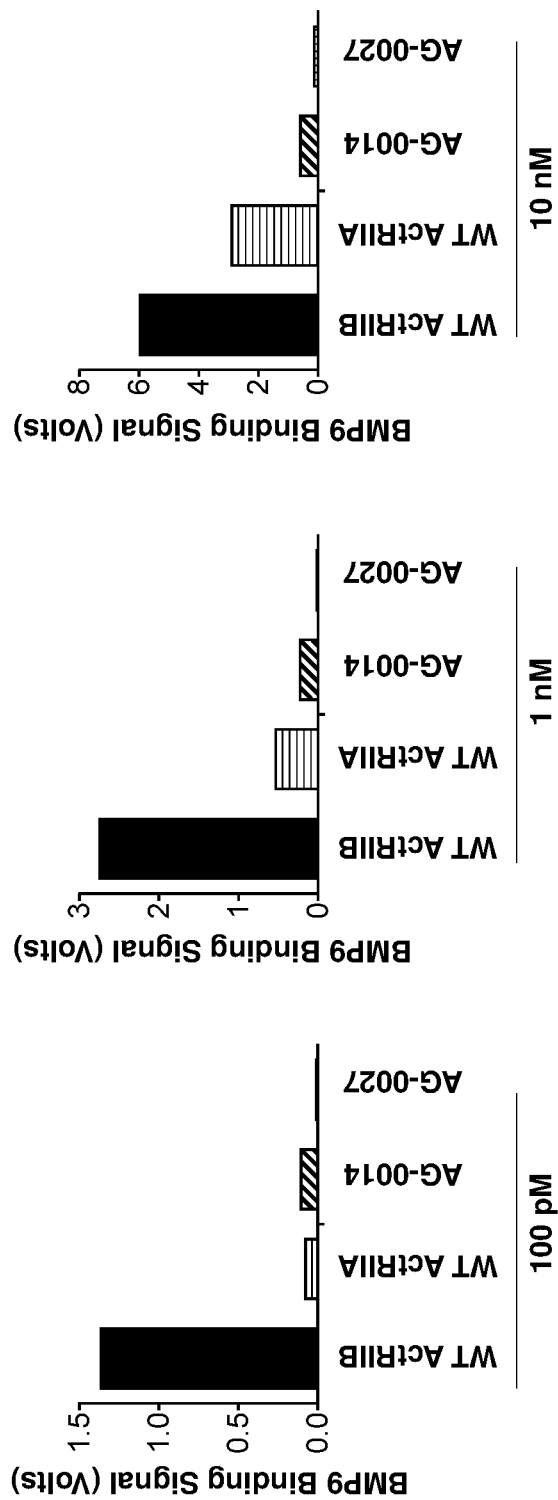
FIG. 12 shows the results of ELISA analysis on BMP9 binding of two exemplary hybrid ActRIIB ligand trap proteins AG-0014 (SEQ ID NO: 16) and AG-0027 (SEQ ID NO: 29), respectively, in comparison to wild-type (WT) ActRIIB-Fc as well as to wild-type ActRIIA-Fc at increasing concentrations. Automated ELISA was performed using KinEXA instrument (Sapidyne Instruments). 20 µg/ml of BMP9 was coupled to NHS-Activated Sepharose 4 Fast Flow beads (GE Healthcare) using the experimental procedure recommended by Sapidyne Instruments. WT ActRIIB-Fc, WT ActRIIA-Fc and each hybrid ActRIIB ligand trap protein were tested for BMP9 binding at 100 pM, 1 nM and 10 nM concentrations as shown in the figure. The wild-type and hybrid proteins were captured on the BMP9-coated beads and detected by Alexa Fluor 647-labeled goat anti-human-Fc antibody (Jackson ImmunoResearch Laboratories, Inc.). The BMP9 binding signals were recorded with KinExA Pro software (Sapidyne Instruments).

Automated ELISA analysis was performed to further characterize the BMP9 binding of hybrid ActRIIB ligand trap proteins at different concentrations in comparison to both wild-type ActRIIB ECD-Fc and wild-type ActRIIA ECD-Fc. As shown in FIG. 12, data reveal that the two exemplary hybrid proteins AG-0014 and AG-0027, respectively, exhibited greatly reduced BMP9 binding compared to either WT ActRIIB-Fc or WT ActRIIA-Fc. These data indicate that the hybrid ActRIIB ligand trap proteins have a remarkable selectivity in BMP9 binding that differs from WT ActRIIB-Fc and WT ActRIIA-Fc.

EXAMPLE 9

In this Example, the differences between the hybrid ActRIIB ligand trap proteins AG-0014 (SEQ ID NO: 16) and AG-0027 (SEQ ID NO: 29) and the benchmark wild-type ActRIIB-Fc was evaluated, with special reference to their potential impact on vascular integrity and bleeding in the nail beds in female 129S1/SvImJ mice.

24 young adult female 129S1/SvImJ mice (Jackson Laboratory) were separated into 4 experimental groups (n=6 per group) and subsequently treated with vehicle (PBS) or with repeated high dose of wild-type ActRIIB-Fc (WT), AG-0027 and AG-0014, respectively, using the dosing regimens as shown in Table 9 below:

TABLE 9

| Group (n = 6) | Compound | Dose | Frequency | Duration | Route |
|---|---|---|---|---|---|
| 1 | Vehicle (PBS) | — | Twice per week | 4 weeks | SC |
| 2 | WT-ActRIIB-Fc | 30 mg/kg | Twice per week | 4 weeks | SC |
| 3 | AG-0027 | 30 mg/kg | Twice per week | 4 weeks | SC |
| 4 | AG-0014 | 30 mg/kg | Twice per week | 4 weeks | SC |

After 4 weeks of treatment, each animal was placed into a transparent-bottom container and examined for any sign of bleeding in the paw nail beds using an inverted microscope.

Figure 13:
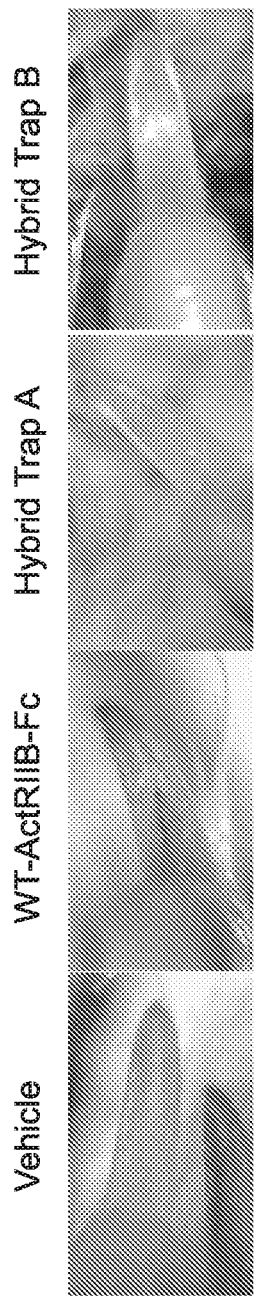
FIG. 13 shows microscopic examination on gross morphology of hindlimb paw nail beds of 129S1/SvImJ mice treated with PBS (vehicle control), Wild-Type ActRIIB-Fc (WT-ActRIIB-Fc), Hybrid Trap A (AG-0027; SEQ ID NO: 29) or Hybrid Trap B (AG-0014; SEQ ID NO: 16). The hindlimb paw nail beds were inspected for signs of bleeding by using an inverted microscope and photographed using a digital camera.

As shown in FIG. 13, microscopic examination on gross morphology revealed that in each of the six 129S1/SvImJ mice that had been treated with the repeated high dose of wild-type ActRIIB-Fc (WT-ActRIIB-Fc), virtually all the paw nail beds had a clear sign of bleeding (FIG. 13, second panel). In contrast, no sign of bleeding in the paw nail beds was observed in the 129S1/SvImJ mice that had been treated with repeated high dose of either of the two hybrid ActRIIB ligand trap proteins. The morphology of the paw nail beds in hybrid ActRIIB ligand trap-treated mice appeared similar to that of the vehicle-treated control animals. These findings suggest that the benchmark compound wild-type ActRIIB-Fc disrupted vasculature and caused bleeding in the nail beds, whereas the hybrid ActRIIB ligand trap proteins did not interfere with vascular homeostasis and maintained normal vascular integrity in the nail beds.

Taken collectively, the results of the present example demonstrate that repeated high dose of WT-ActRIIB-Fc administered SC at 30 mg/kg, twice per week, for 4 weeks led to clear signs of bleeding in the paw nail beds and the Brunner's glands in 129S1/SvImJ female mice. In contrast, 4 weeks of repeated high dose treatment with AG-0027 or AG-0014 caused no sign of bleeding in the nail beds in the 129S1/SvImJ female mice. Thus, the hybrid ActRIIB ligand trap molecules had no negative influence on blood vessel integrity as the wild-type ActRIIB-Fc did. These findings demonstrate that the hybrid ActRIIB ligand trap molecules differ dramatically from wild-type ActRIIB-Fc with respect to in vivo selectivity and, unlike the wild-type ActRIIB-Fc that disrupts vasculature, the hybrid ActRIIB ligand trap proteins maintain normal vasculature integrity without interfering with vascular homeostasis. As such, with superior in vivo selectivity and in vivo efficacy (see examples below), hybrid ActRIIB ligand trap proteins clearly offer distinct therapeutic advantages in safety and efficacy over wild-type ActRIIB-Fc or any similar prior-generation molecules.

EXAMPLE 10

In this Example, the in vivo efficacy of AG-0027 (SEQ ID NO: 29) in enhancing muscle mass and bone density as well as the ability of AG-0027 to reverse androgen deprivation-induced muscle wasting and bone loss in orchiectomized C57BL/6 mice was evaluated.

18 male C57BL/6 mice of 10 weeks of age including 6 normal control mice and 12 orchiectomized (ORX) mice (Charles River Laboratory) were subcutaneously injected with either vehicle (PBS, pH7.4) or AG-0027 using the dosing regimens as shown in the Table 10 below:

TABLE 10

| Group | Mice | n | Treatment | Dose | Frequency | Route | Duration |
|---|---|---|---|---|---|---|---|
| 1 | Normal | 6 | Vehicle | — | 2×/week | SC | 6 weeks |
| 2 | ORX | 6 | Vehicle | — | 2×/week | SC | 6 weeks |
| 3 | ORX | 6 | AG-0027 | 10 mg/kg | 2×/week | SC | 6 weeks |

Longitudinal body weights were recorded twice per week throughout the 6-week treatment period. On day 42, the mice were euthanized with $CO_2$ asphyxiation. Tissues, including the lean carcass, heart, and individual hindlimb muscles (gastrocnemius, quadriceps and soleus), as well as the femur and the lumbar vertebrae, were dissected from each animal. The lean carcass, heart, and individual hindlimb muscle pairs (both left and right) were weighed using digital balances with the values being recorded. Bone tissues, including the distal femur and the 4th lumbar vertebrae from each animal, were analyzed by high-resolution micro-computed tomography (microCT) using a microCT imaging system. Bone volume (BV/TV, %), trabecular number (Tb.N, mm−1), trabecular thickness (Tb.Th, mm) and trabecular separation (Tb.Sp, mm) of the distal femur and the $4^{th}$ lumbar vertebrae were calculated based on consecutive microCT scans of the 6 femur and lumbar bone samples from each group.

Figure 14:
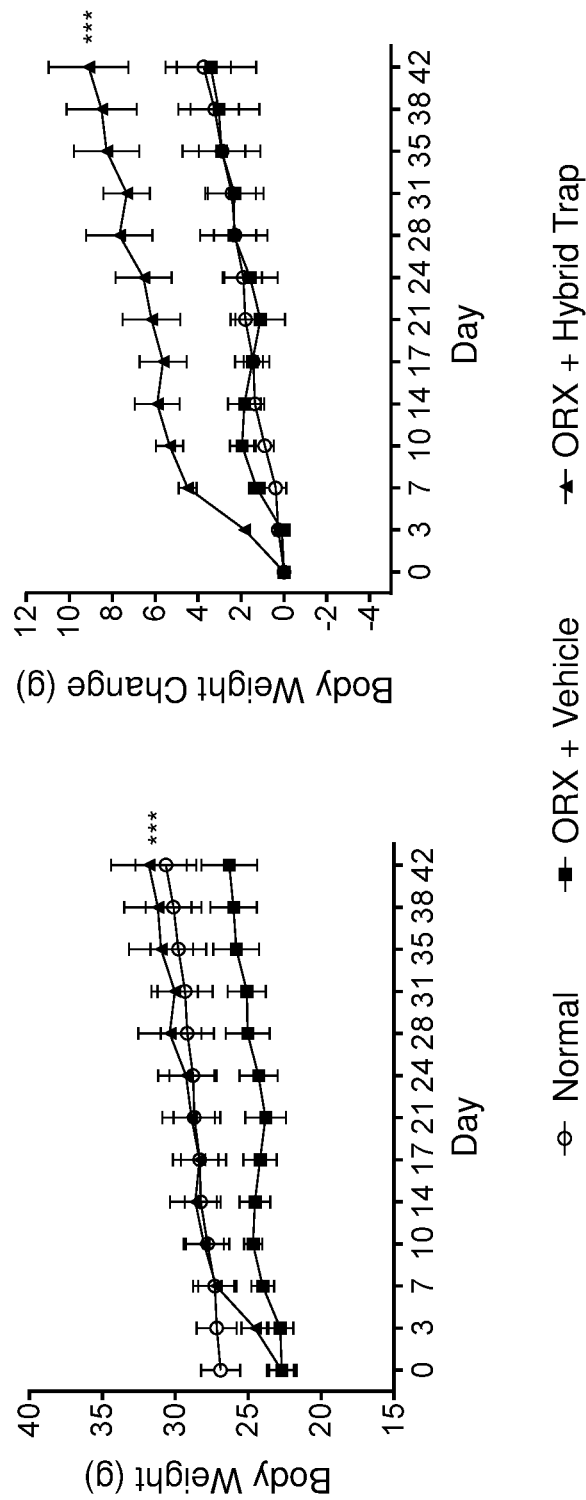
FIG. 14 shows line graphs depicting the effect of Hybrid Trap (AG-0027; SEQ ID NO: 29) administration on body weight in ORX C57BL/6 mice. Data illustrate the longitudinally recorded body weights (left panel) and body weight changes (right panel) in normal control group, vehicle-treated ORX group, and Hybrid Trap-treated ORX group. Statistical analysis was performed using Student's t-test. ***: P<0.001 vs. vehicle-treated ORX group. n=6.

As shown in FIG. 14, body weight data (left panel) indicates that the ORX C57BL/6 mice had a marked reduction in body weight compared to the normal control C57BL/6 mice. Within one week of treatment, AG-0027 led to complete reversal of weight loss in the ORX mice (left panel) and AG-0027 administration resulted in a rapid, sustained and statistically significant body weight gain compared to both vehicle-treated ORX mice and normal control mice (see right panel).

Figure 15:
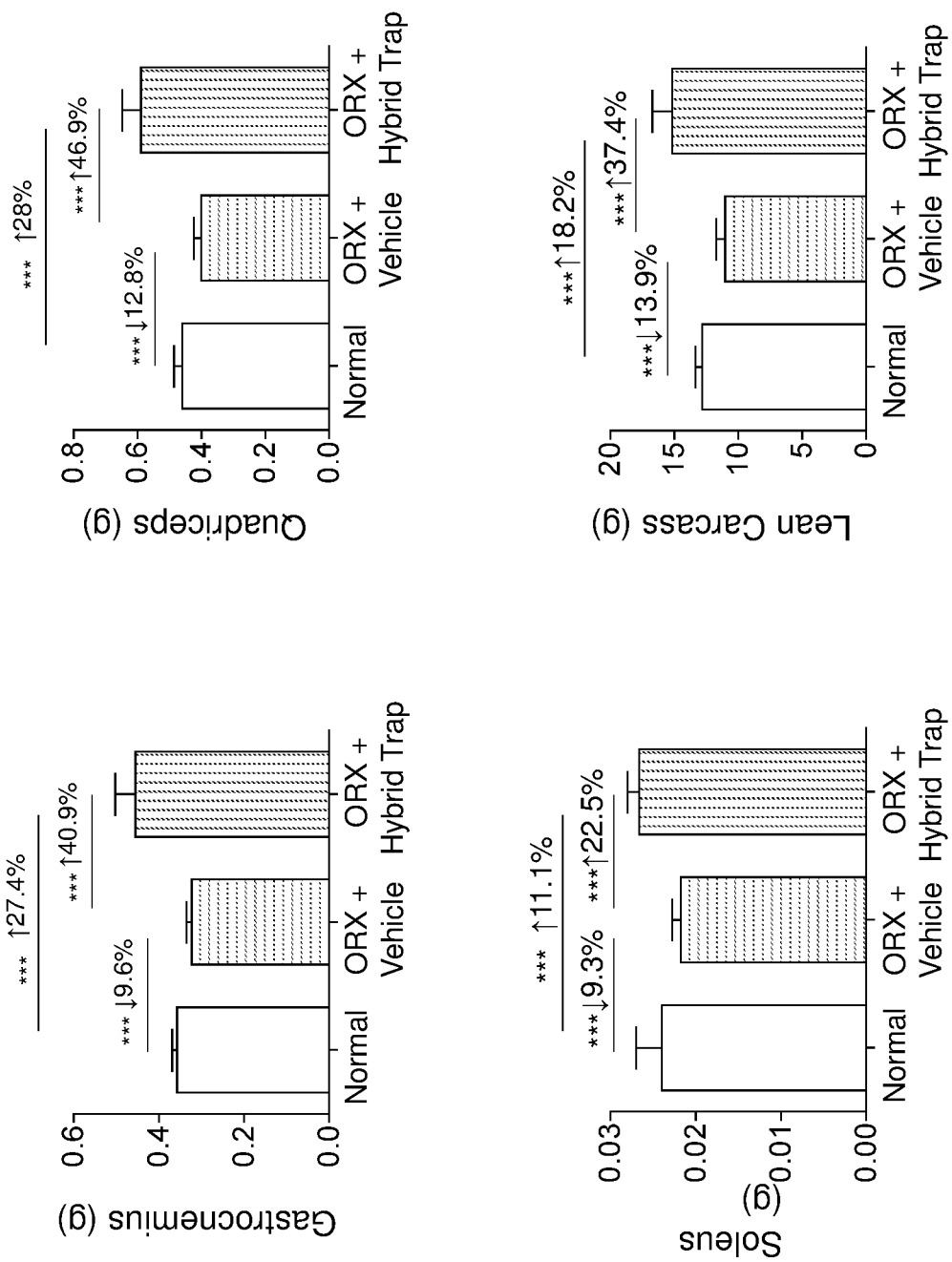
FIG. 15 shows bar graphs depicting the effect of hybrid ActRIIB ligand trap (AG-0027; SEQ ID NO: 29) treatment on hindlimb muscle mass and lean carcass mass in orchiectomized (ORX) mice. Gastrocnemius, quadriceps and soleus muscle weights and lean carcass weights were recorded during terminal necropsy on day 42 for normal control group, vehicle-treated ORX group and hybrid ActRIIB ligand trap-treated ORX group. Data on the average gastrocnemius, quadriceps and soleus muscle weights were based on each hindlimb muscle pairs. Statistical analysis was performed using Student's t-test. ***: P<0.001. n=6.

FIG. 15 shows the changes in individual hindlimb muscle mass and lean carcass weights. Data indicate that the vehicle-treated ORX group had a significant loss of hindlimb muscle mass by 9%-13% and loss of lean carcass mass by nearly 14% compared to the normal control group. In contrast, the AG-0027-treated ORX group showed marked increases in hindlimb muscle mass by 22%-47% and in lean carcass mass by nearly 37% compared to the vehicle-treated ORX group and also showed significant increases in hindlimb muscle mass by 11%-28% and in lean carcass mass by 18% compared to the normal control group. Remarkably, not only did AG-0027 completely reverse the muscle atrophy in ORX mice, it also caused a strong muscle gain in the treated ORX mice that exceeded the level in the normal control group. In the vehicle-treated ORX group, there was a significant loss of both fast-twitch (i.e., gastrocnemius and quadriceps) and slow-twitch (i.e., soleus) muscles and AG-0027 treatment effectively reversed the loss of both these muscle types in the ORX mice (see FIG. 15). These findings demonstrate that AG-0027 has a potent in vivo efficacy on muscle growth and is highly capable of reversing muscle atrophy.

Figure 16:
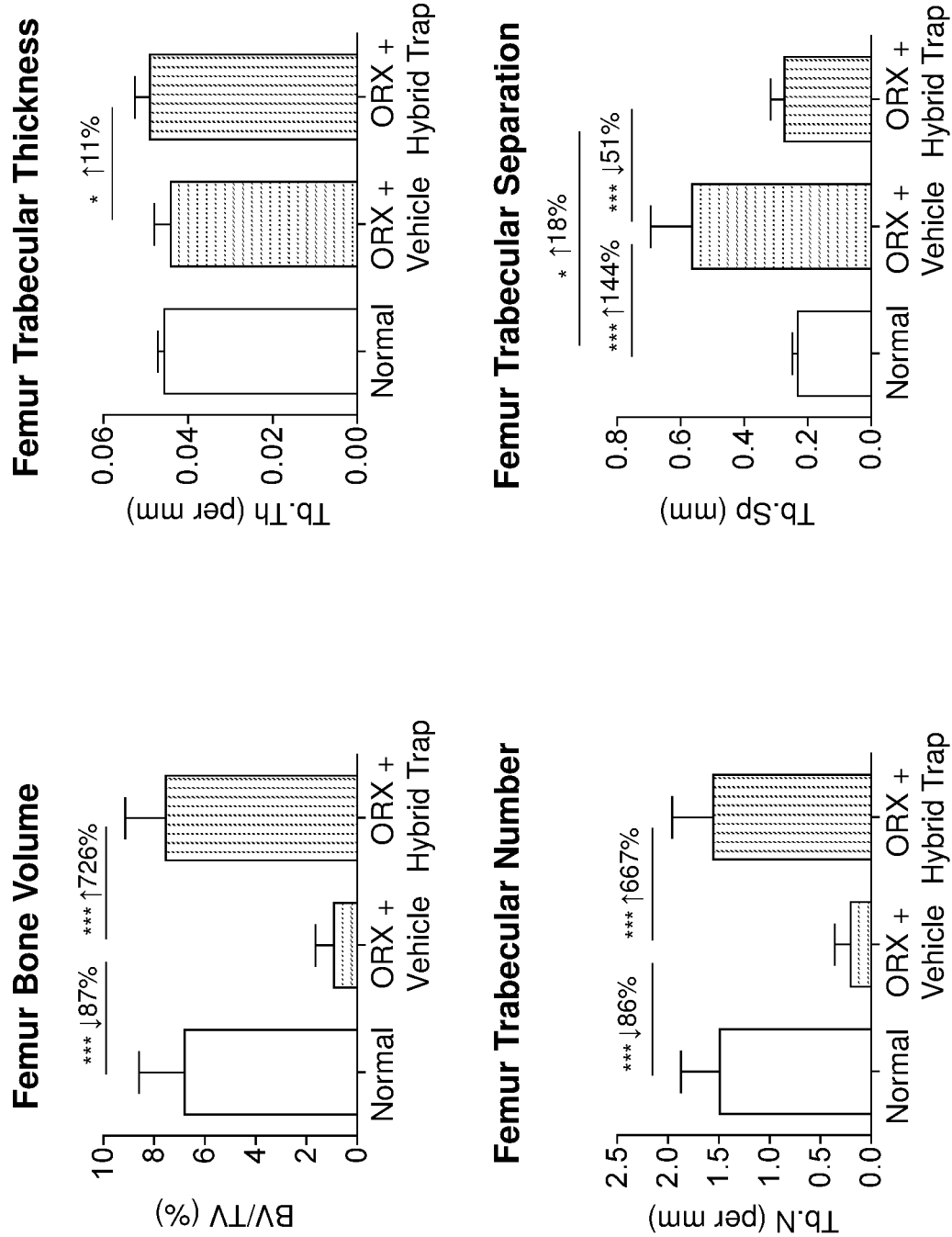
FIG. 16 shows bar graphs depicting microCT analysis of bone volume fraction (BV/TV, %), trabecular thickness (Tb.Th, mm), trabecular number (Tb.N, mm−1) and trabecular separation (Tb.Sp, mm) of the distal femur in normal mice (Normal), vehicle-treated ORX mice (ORX+Vehicle) and hybrid ActRIIB ligand trap (AG-0027; SEQ ID NO: 29)-treated ORX mice (ORX+Hybrid Trap). Student's t-test was used for statistical analysis. *: P<0.05; : P<0.01; *: P<0.001. n=6.
Figure 17:
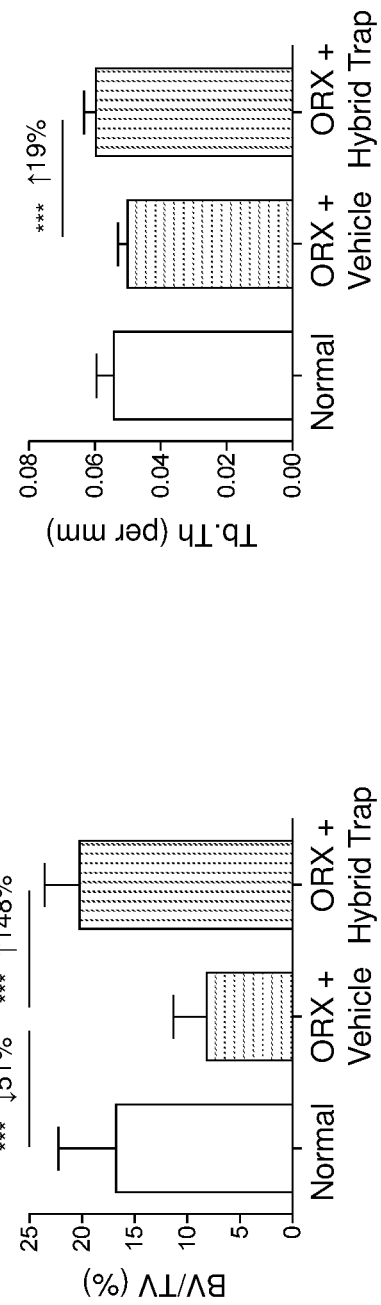
FIG. 17 shows bar graphs depicting MicroCT analysis of bone volume fraction (BV/TV, %), trabecular thickness (Tb.Th, mm), trabecular number (Tb.N, mm−1) and trabecular separation (Tb.Sp, mm) of the $4^{th}$ lumbar vertebrae in normal mice (Normal), vehicle-treated ORX mice (ORX+Vehicle) and hybrid ActRIIB ligand trap (AG-0027; SEQ ID NO: 29)-treated ORX mice (ORX+Hybrid Trap). Student's t-test was used for statistical analysis. *: P<0.05; : P<0.01; *: P<0.001. n=6.
Figure 17:
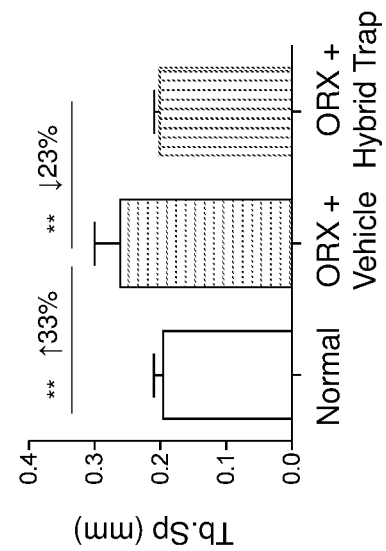
Figure 17:
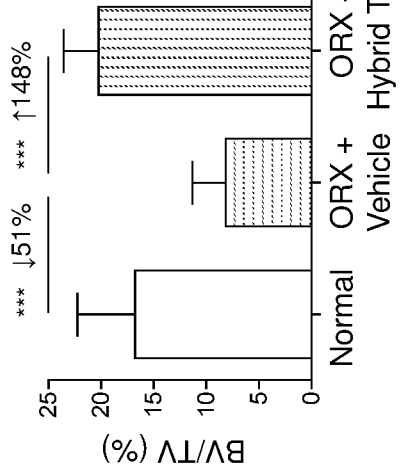
Figure 17:
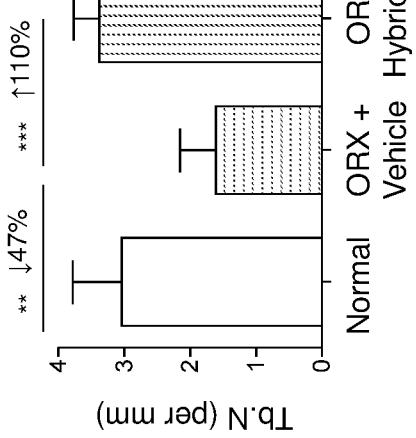
Figure 18:
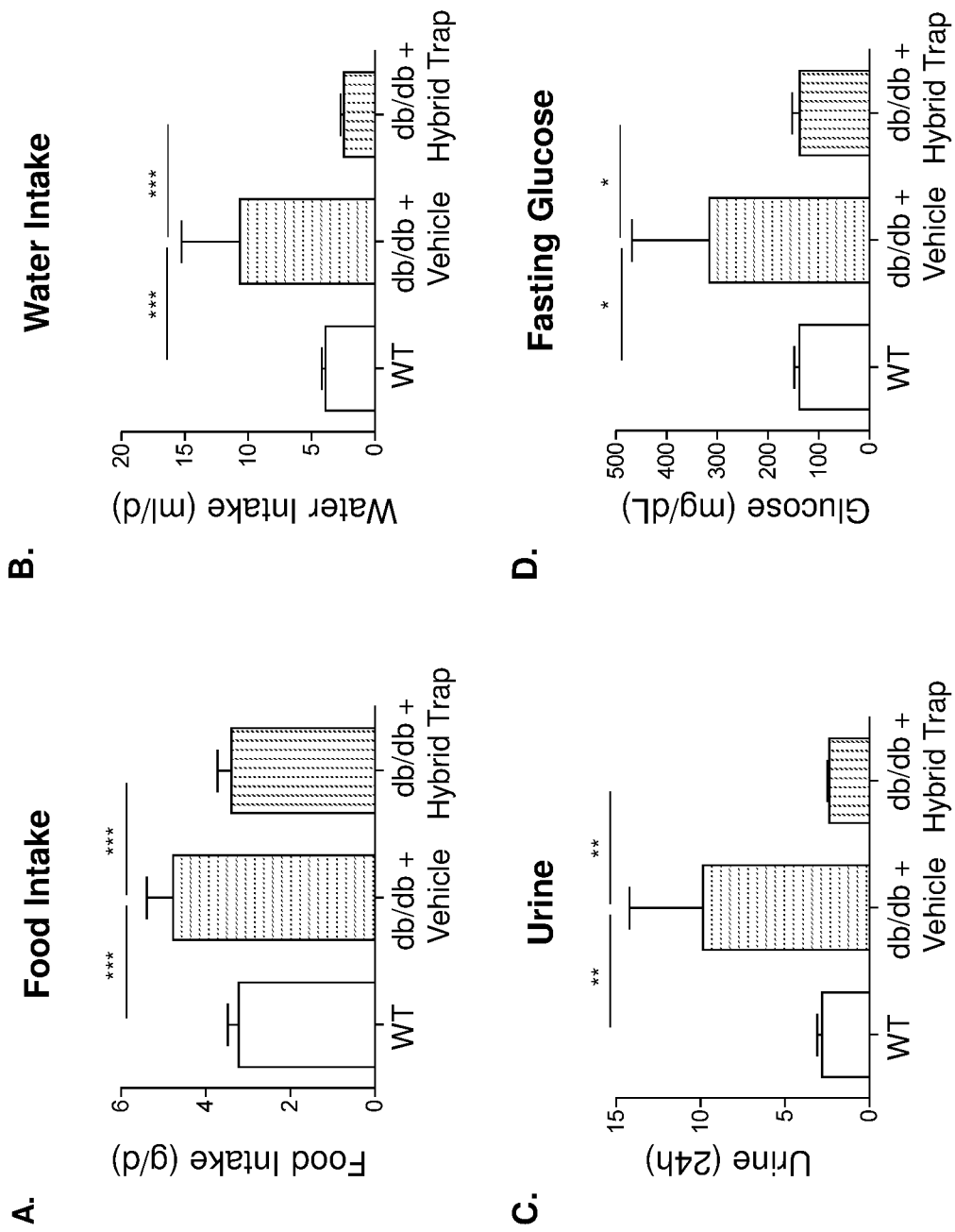
FIG. 18 shows bar graphs depicting the effect of hybrid ActRIIB ligand trap (AG-0027; SEQ ID NO: 29) treatment on food intake (A), water consumption (B), 24-hour urine volume (C) and fasting blood glucose level (D) in diabetic db/db mice. Heterozygous db/db mice (n=6) are used as non-diabetic control. Food intake, water consumption, 24-hour urine volume and fasting blood glucose level are measured after 10 weeks of treatment. Statistical analysis is performed by Student's t-test. *: P<0.05; : P<0.01; *: P<0.001. n=6 per group.

FIG. 16 and FIG. 17 also show the results of microCT analysis of bone density in the distal femur (FIG. 16) and the $4^{th}$ lumbar vertebrae (FIG. 17) in normal control mice, vehicle-treated ORX mice, and AG-0027-treated ORX mice. As shown in FIG. 18, ORX mice showed marked loss of bone mass in the distal femur with statistically significant decreases in bone volume fraction (BV/TV, %) and trabecular number (Tb.N, mm−1) in the distal femur by >86% and a marked increase in trabecular separation (Tb.Sp, mm) by 144% in comparison to the normal control mice; however, treatment of the ORX mice with AG-0027 dramatically increased the bone volume fraction (BV/TV, %) by 726% and the trabecular number (Tb.N, mm−1) by 667% and decreased trabecular separation (Tb.Sp, mm) by 51%, thereby completely reversing the loss of distal femur bone density in the ORX mice resulting from androgen deprivation. Furthermore, as shown by the microCT data, AG-0027 treatment significantly increased the trabecular thickness of the distal femur in the ORX mice to 11% beyond the normal control level seen in normal mice. As shown in FIG. 17, the orchiectomy-induced androgen deprivation led to a marked loss of bone mass in the lumbar vertebrae in the ORX mice, which was completely reversed by AG-0027 treatment (see FIG. 17). Specifically, the vehicle-treated ORX mice showed statistically significant decreases in bone volume fraction (BV/TV, %) and trabecular number (Tb.N, mm−1) in the $4^{th}$ lumbar vertebrae by approximately 50% compared and also a statistically significant decrease in (Tb.Sp, mm) by 33% in comparison to normal control mice; however, treatment of the ORX mice with AG-0027 dramatically increased the lumbar bone volume fraction by 148% and the lumbar trabecular number by 110% and decreased the lumbar trabecular separation (Tb.Sp, mm) by 23%, thereby completely ameliorating the marked loss of the lumbar bone density in ORX mice resulting from androgen deprivation. Moreover, AG-0027 treatment significantly increased the trabecular thickness of the lumbar spine in the ORX mice to 19% beyond the normal control value seen in normal mice. These data demonstrate that AG-0027 has a potent bone anabolic effect in vivo and AG-0027 treatment is highly effective in reversing bone loss.

In summary, the data in this example for the ORX mice show that subcutaneous administration of AG-0027 led to dramatic increases in body weight, muscle mass and bone mass and completely reversed the profound muscle atrophy and bone loss due to androgen deprivation. The remarkable in vivo efficacy on muscle and bone anabolism demonstrates that AG-0027 as a next-generation therapeutic offers strong therapeutic potential for the treatment of various muscle and bone disorders.

EXAMPLE 11

Diabetes is a major public health problem that is approaching epidemic proportions globally. It has been shown that increasing muscle mass and function with exercise can improve insulin sensitivity and improve diabetic conditions. The data in the preceding examples clearly establishes that a hybrid ActRIIB ligand trap such as AG-0027 (SEQ ID NO: 29) is capable of strongly enhancing muscle growth and muscle regeneration by selectively antagonizing myostatin/activin-Smad2/3 signaling pathway. In this Example, the influence of muscle growth on glucose metabolism is examined using a diabetic mice treated with either AG-0027 or vehicle.

Homozygous db/db diabetic mice (Jackson Laboratory, Bar Harbor, ME) are treated with AG-0027 at increasing doses up to 30 mg/kg, or with vehicle (PBS, pH 7.4) for 10 or 12 weeks, and heterozygous db/db mice are used as non-diabetic control (n=6 per group). Changes in food intake, water consumption, 24-hour urine volume, fasting blood glucose and body weight are examined. At the end of the study, the mice are ethanized with $CO_2$. Blood samples are collected and serum insulin, HbA1c, adeponectin levels are measured using commercially available assay kits. Body compositions including abdominal fat, muscle mass and brown fat mass, are determined by necropsy analysis. Liver tissues are examined histologically with H&E staining and Oil-Red O staining.

FIG. 18 shows the effect of AG-0027 treatment on food intake, water cosumption, 24-hour urine volume, and fasting glucose levels in diabetic db/db mice. Subcutaneous administration of hybrid ActRIIB ligand trap protein AG-0027 dramatically normalized food consumption, water intake, 24-hour urine volume, and fasting glucose levels in the diabetic db/db mice. Therefore, the data indicate that pharmacological blockade of myostatin/activin-Smad2/3 signaling in db/db diabetic mice is able to ameliorate metabolic dysfunctions as the treatment with the hybrid ActRIIB ligand trap protein is found to effectively reduce food intake and water consumption, decrease blood glucose level, and reduce 24-hour urine volume. The treatment also ameliorated fatty liver in db/db mice. Therefore, hybrid ActRIIB ligand trap proteins like AG-0027 appear to offer therapeutic potential for the treatment of metabolic diseases including diabetes, diabetic nephropathy, metabolic syndrome, obesity and fatty liver.

EXAMPLE 12

In this Example, the in vivo efficacy of AG-0014 (SEQ ID NO: 16) and AG-0027 (SEQ ID NO: 29) on body weight gain and muscle growth is evaluated in comparison with the wild type ActRIIB-Fc (WT-ActRIIB-Fc) as a benchmark in C57Bl/6 mice.

Figure 19:
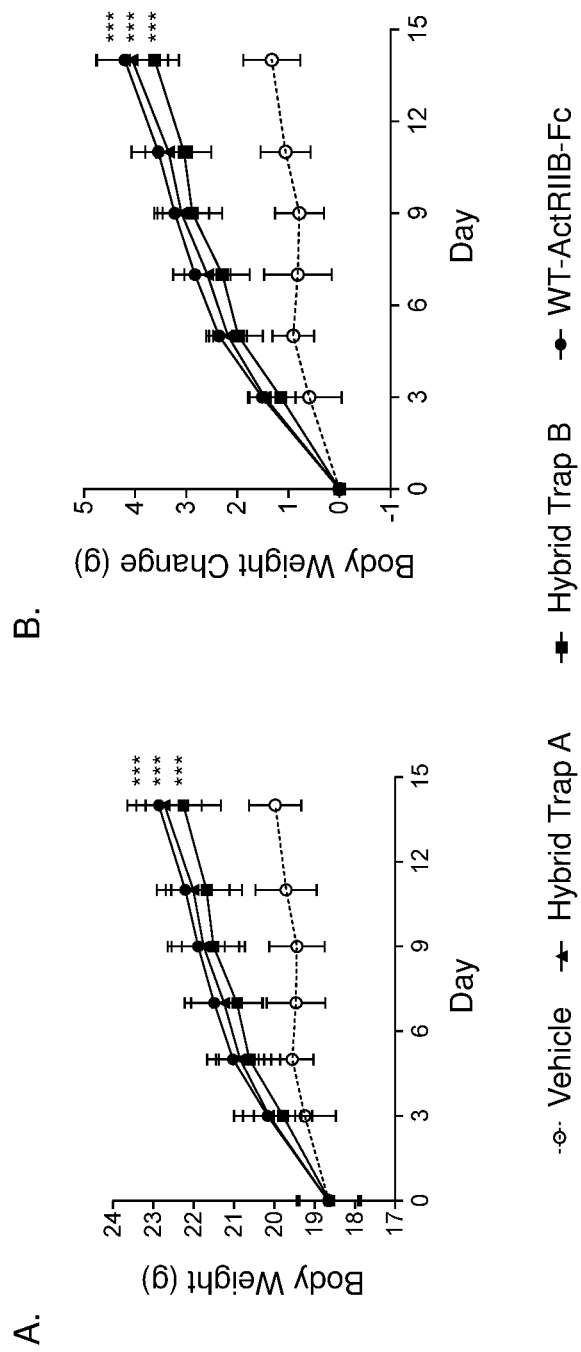
FIG. 19 shows the effect of single dose of hybrid ActRIIB ligand trap (Hybrid Trap) proteins on body weight change in female C57BL/6 mice. Seven-week-old female C57BL/6 mice (n=6 per group) were subcutaneously treated with a single injection of Hybrid Trap A (AG-0027; SEQ ID NO: 29), Hybrid Trap B (AG-0014; SEQ ID NO: 16), and wild type ActRIIB-Fc (WT-ActRIIB-Fc) at 10 mg/kg, respectively. Control group received a single injection of vehicle (PBS). Body weight (A) and body weight change from baseline (B) were recorded in PBS- and Hybrid Trap-treated mice at different time points up to 14 days post injection. Statistical analysis was performed using Student's t-test. ***: P<0.001; n=6 per group. Error bars represent standard deviation.
Figure 20:
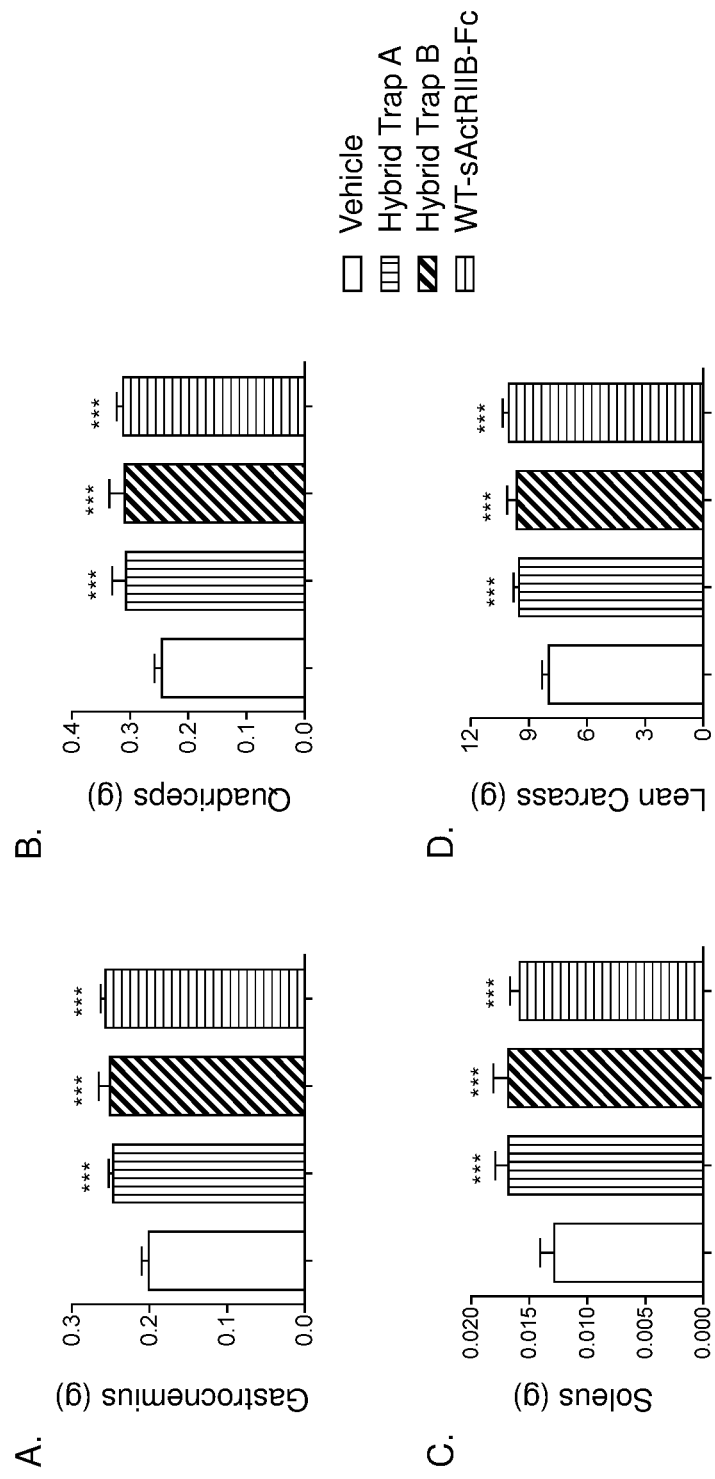
FIG. 20 shows the head-to-head comparison of the effects of single injection of hybrid ActRIIB ligand trap (Hybrid Trap) proteins on hindlimb muscle mass and lean carcass mass in C57BL/6 mice. Mice were subcutaneously treated with a single dose, at 10 mg/kg, of Hybrid Trap A (AG-0027; SEQ ID NO: 29), Hybrid Trap B (AG-0014; SEQ ID NO: 16) and WT-ActRIIB-Fc (benchmark), respectively, or with vehicle (PBS). On day 14 after injection, the mice were subjected to terminal necropsy. The weights of hindlimb muscles, including the gastrocnemius (A), the quadriceps (B) and the soleus (C), and the lean carcass weights (D) were determined for PBS-, Hybrid Trap A- and Hybrid Trap B-treated groups. Statistical analysis was performed using Student's t-test. ***: P<0.001; n=6 per group. Error bars represent standard deviation. Statistical analysis was performed using Student's t-test.

Seven-week-old female C57BL/6 mice (n=6 per group) were subcutaneously treated with a single injection of Hybrid Trap A (AG-0027; SEQ ID NO: 29), Hybrid Trap B (AG-0014; SEQ ID NO: 16), and wild type ActRIIB-Fc (WT-ActRIIB-Fc) at 10 mg/kg, respectively, or with a single injection of vehicle (PBS). Body weight recorded up to 14 days post the single injection showed that AG-0027 and AG-0014 treatment elicited equally strong weight gain as compared to WT-ActRIIB-Fc (FIG. 19). Terminal necropsy analysis was performed on day 14 and data demonstrated that treatment with AG-0014 and AG-0027 resulted in significant increases in the mass of the three individual hinadlimb muscles examined, including the gastrocnemius, the quadriceps and the soleus, at the same level as benchmark WT-ActRIIB-Fc (FIG. 20). These data demonstrate that hybrid ActRIIB ligand traps proteins like AG-0014 and AG-0027 are able to display full in vivo efficacy on muscle growth as compared to wild type ActRIIB-Fc.

EXAMPLE 13

In this Example, the dose-dependent in vivo efficacy of AG-0014 (SEQ ID NO: 16) and AG-0027 (SEQ ID NO: 29) in enhancing body weight gain and skeletal muscle growth is evaluated in C57Bl/6 mice.

Figure 21:
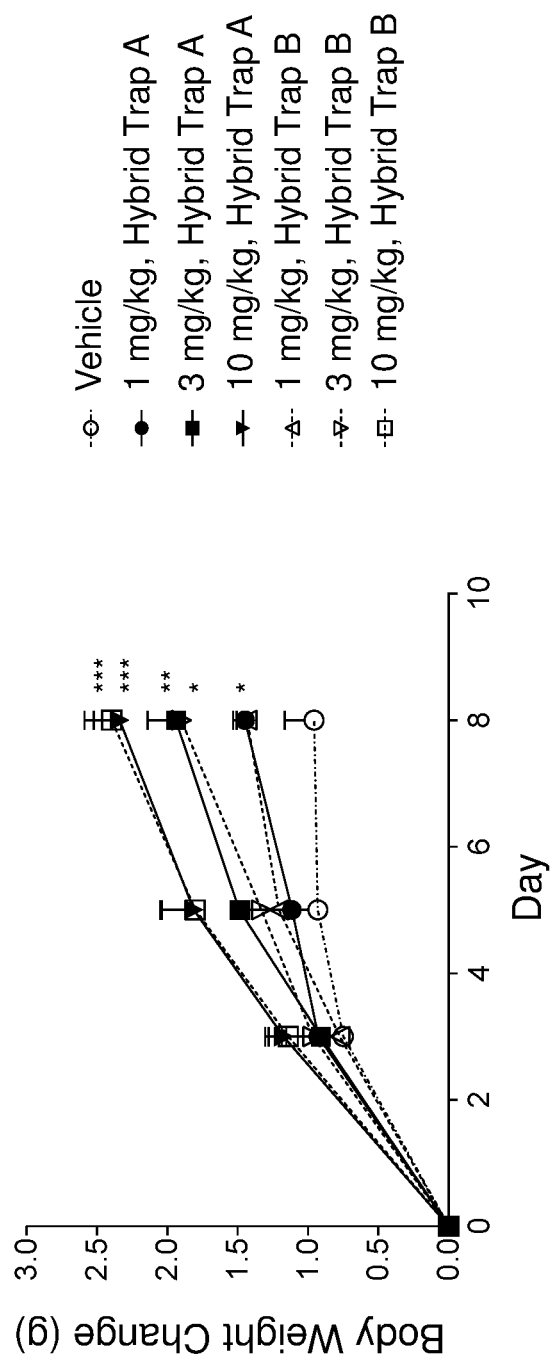
FIG. 21 shows the effect of single ascending doses of hybrid ActRIIB ligand trap (Hybrid Trap) proteins on body weight change in female C57BL/6 mice. Six-week-old female C57BL/6mice were subcutaneously treated with single ascending doses of Hybrid Trap A (AG-0027; SEQ ID NO: 29) and Hybrid Trap B (AG-0014 (SEQ ID NO: 16) at 1 mg/kg, 3 mg/kg and 10 mg/kg, respectively. Control group was treated with vehicle (PBS). Body weight and body weight change from baseline in PBS-treated and Hybrid Trap-treated mice were recorded up to 8 days post injection. Statistical analysis was performed using Student's t-test. *: P<0.05; : P<0.01; *: P<0.001; n=6 per group. Error bars represent standard deviation.
Figure 22:
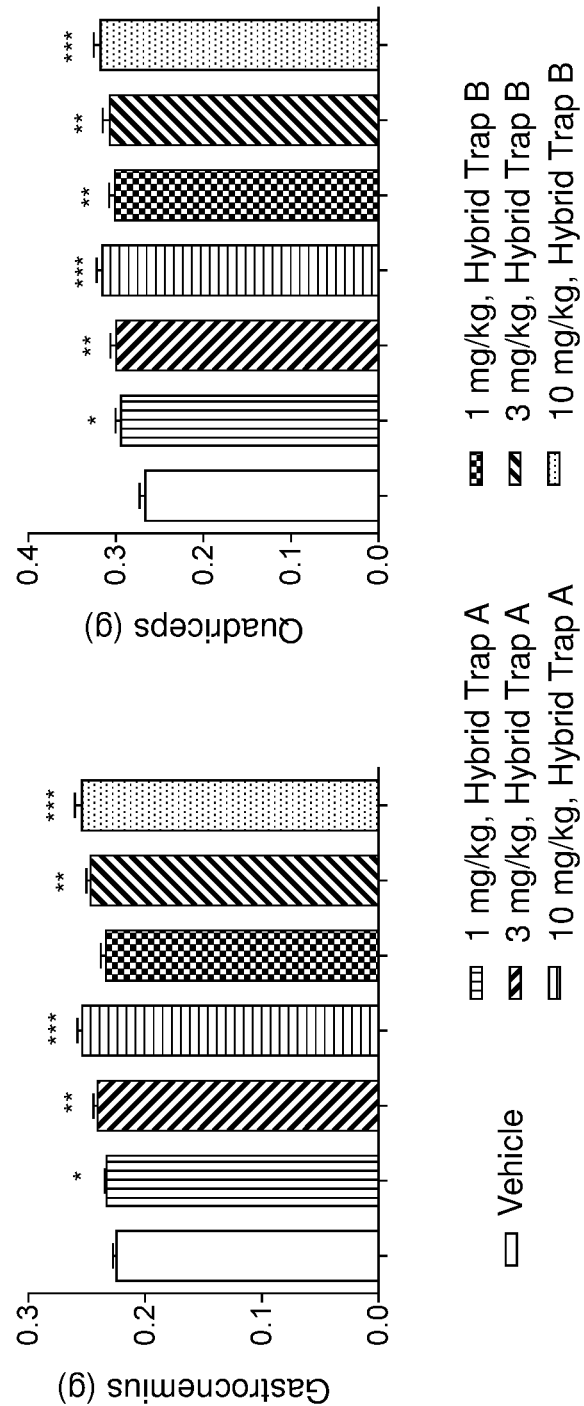
FIG. 22 illustrates the effect of single ascending doses of hybrid ActRIIB ligand trap (Hybrid Trap) proteins on hindlimb muscle mass in female C57BL/6 mice. Hybrid Trap A (AG-0027; SEQ ID NO: 29) and Hybrid Trap B (AG-0014 (SEQ ID NO: 16) were given subcutaneously at 1 mg/kg, 3/mg/kg and 10 mg/kg, respectively. On day 8, the mice were euthanized for terminal necropsy. The weights of hindlimb muscles including the gastrocnemius (A) and the quadriceps (B) were determined by necropsy procedures for PBS-, Hybrid Trap A- and Hybrid Trap B-treated groups. Statistical analysis was performed using Student's t-test. *: P<0.05; : P<0.01; *: P<0.001; n=6 per group. Error bars represent standard deviation. Statistical analysis was performed using Student's t-test.
Figure 23:
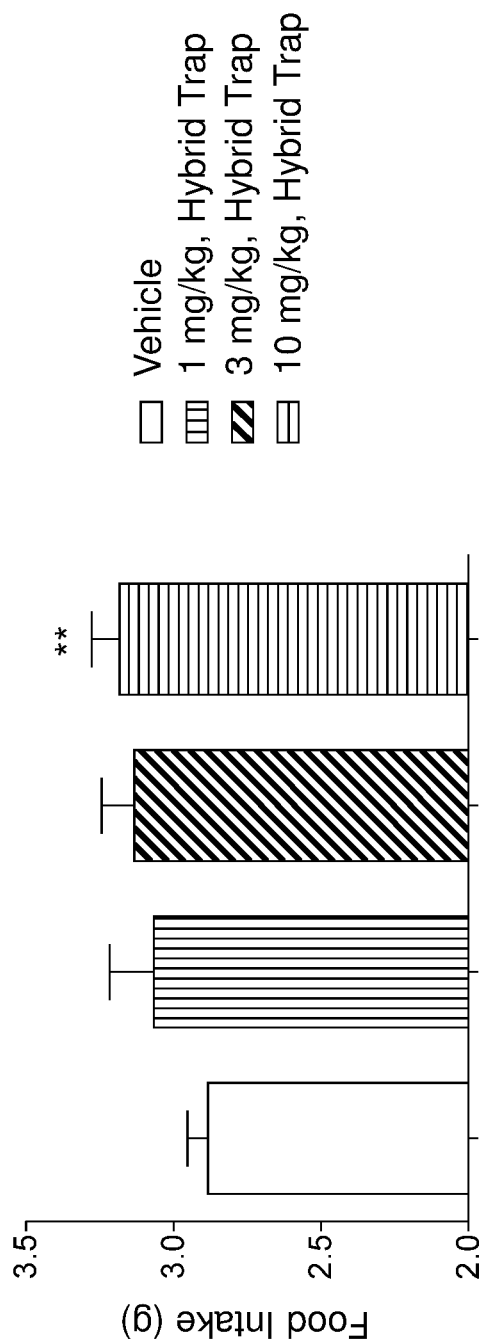
FIG. 23 shows the effect of single ascending doses of hybrid ActRIIB ligand trap (Hybrid Trap) protein on food intake in female C57BL/6 mice. Six-week-old female C57BL/6mice were treated with single ascending doses of Hybrid Trap (AG-0027; SEQ ID NO: 29), SC, at 1 mg/kg, 3 mg/kg and 10 mg/kg, respectively. Data illustrate the recorded food intake on day 8 in PBS-treated and Hybrid Trap-treated mice. Statistical analysis was performed using Student's t-test. **: P<0.01; n=6 per group. Error bars represent standard deviation.

Six-week-old female C57BL/6mice were subcutaneously treated with single ascending doses of Hybrid Trap A (AG-0027; SEQ ID NO: 29) and Hybrid Trap B (AG-0014 (SEQ ID NO: 16), respectively, at 1 mg/kg, 3 mg/kg and 10 mg/kg. Body weight and body weight change from baseline in PBS-treated and Hybrid Trap-treated mice were recorded up to 8 days post injection. Body weight data demonstrate that hybrid ActRIIB lingand trap proteins AG-0014 and AG-0027 are able to stimulate body weight gain in a dose-dependent manner (FIG. 21). Terminal necropsy analysis of the weights of hindlimb muscles further demonstrate that treatment with AG-0014 or AG-0027 resulted in statistically significant increases in gastrocnemius muscle mass (A) and quadriceps muscle mass (B) in a dose-dependent manner. These data show that hybrid ActRIIB lingand trap proteins like AG-0014 and AG-0027 are capable of stimulating muscle growth in a dose-dependent manner.

EXAMPLE 14

Muscular dystrophy is a group of highly debilitating diseases that cause progressive weakness and loss of muscle mass as well as bone fragility. The data in the preceding examples clearly establishes that a hybrid ActRIIB ligand trap proteins such as AG-0014 (SEQ ID NO: 16) and AG-0027 (SEQ ID NO: 29) are capable of strongly enhancing muscle growth, muscle regeneration and bone formation in MDX mice, a disease model of Duchenne muscular dystrophy, by selectively antagonizing myostatin/activin-Smad2/3 signaling pathway. In this Example, the therapeutic potential of AG-0014 and AG-0027 for treating muscular dystrophy is evaluated.

Figure 24:
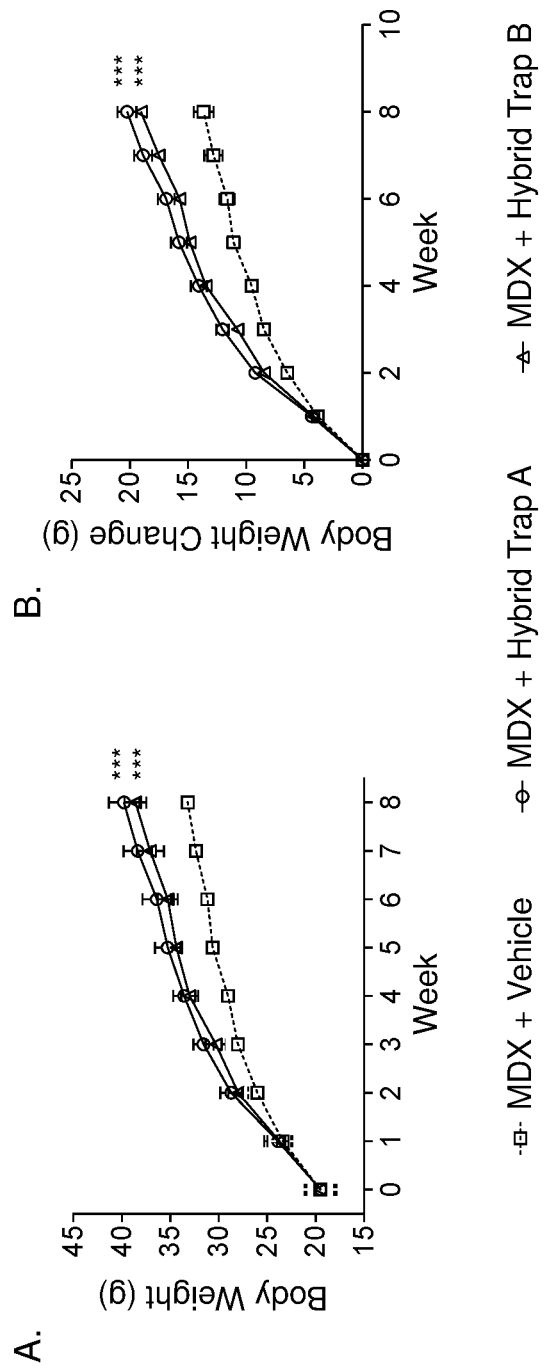
FIG. 24 illustrates the effect of subcutaneous administration of hybrid ActRIIB ligand trap (Hybrid Trap) proteins on body weight in Duchenne muscular dystrophy (MDX) mice. Four-week-old MDX mice were treated with vehicle (PBS) or with Hybrid Trap A (AG-0027; SEQ ID NO: 29) or with Hybrid Trap B (AG-0014 (SEQ ID NO: 16), SC, at 10 mg/kg, once per week, for eight weeks. Data show the longitudinally recorded body weight (A) and body weight change from baseline (B) in PBS-treated and Hybrid Trap-treated MDX mice. Statistical analysis was performed using Student's t-test. ***: P<0.001; n=8 per group. Error bars represent standard deviation.
Figure 25:
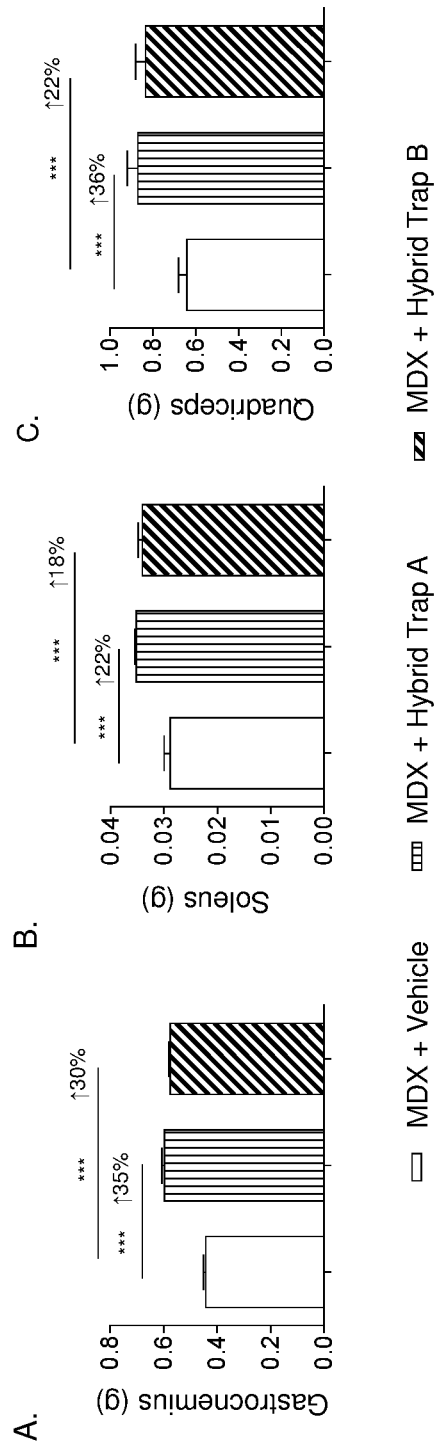
FIG. 25 shows the effect of subcutaneous administration of hybrid ActRIIB ligand trap (Hybrid Trap) proteins on hindlimb muscle mass in MDX mice. MDX mice were subcutaneously treated with Hybrid Trap A (AG-0027; SEQ ID NO: 29) and Hybrid Trap B (AG-0014 (SEQ ID NO: 16) at 10 mg/kg, once per week, or with vehicle (PBS) for 8 weeks. On day 56, the MDX mice were euthanized for terminal necropsy. The weights of individual hindlimb muscles including the gastrocnemius (A), the quadriceps (B) and the soleus (C) were determined by necropsy procedures in the MDX mice treated with PBS (MDX+PBS) or with Hybrid Trap A (MDX+Hybrid Trap A) or with Hybrid Trap B (MDX+Hybrid Trap B). Statistical analysis was performed using Student's t-test. ***: P<0.001; n=8 per group. Error bars represent standard deviation.
Figure 26:
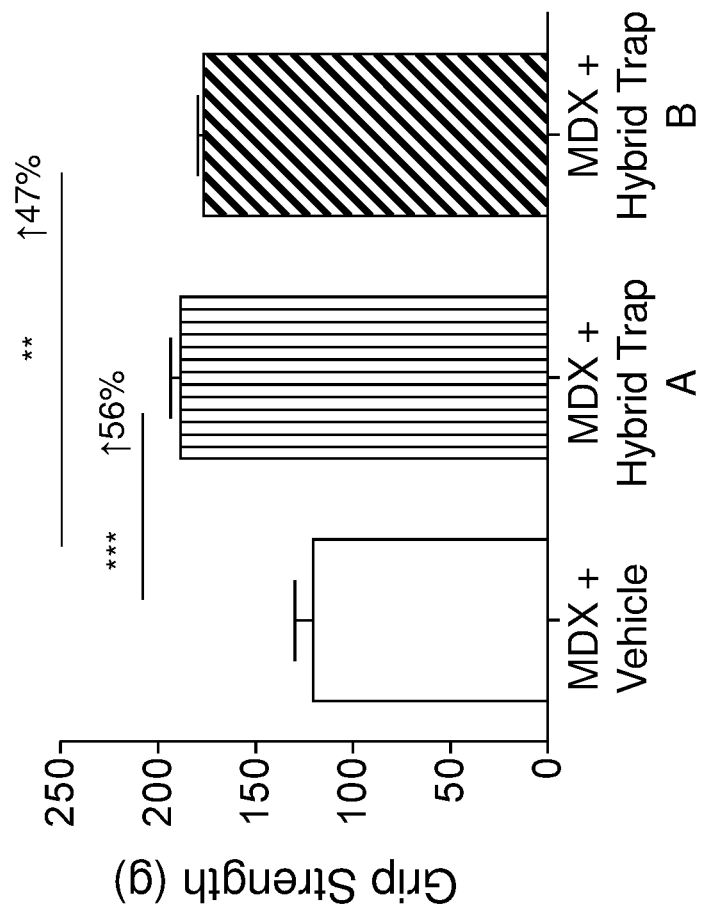
FIG. 26 shows the effect of subcutaneous administration of hybrid ActRIIB ligand trap (Hybrid Trap) proteins on grip strength in MDX mice. Grip strength was analyzed on week 8 in the MDX mice treated with PBS (MDX+PBS) or with Hybrid Trap A (AG-0027; SEQ ID NO: 29) (MDX+Hybrid Trap A) or Hybrid Trap B (MDX+Hybrid Trap B) (AG-0014 (SEQ ID NO: 16) by using BIOSEB grip strength meter (EB-instruments). Statistical analysis was performed using Student's t-test. ***: P<0.001; n=8 per group. Error bars represent standard deviation.
Figure 27:
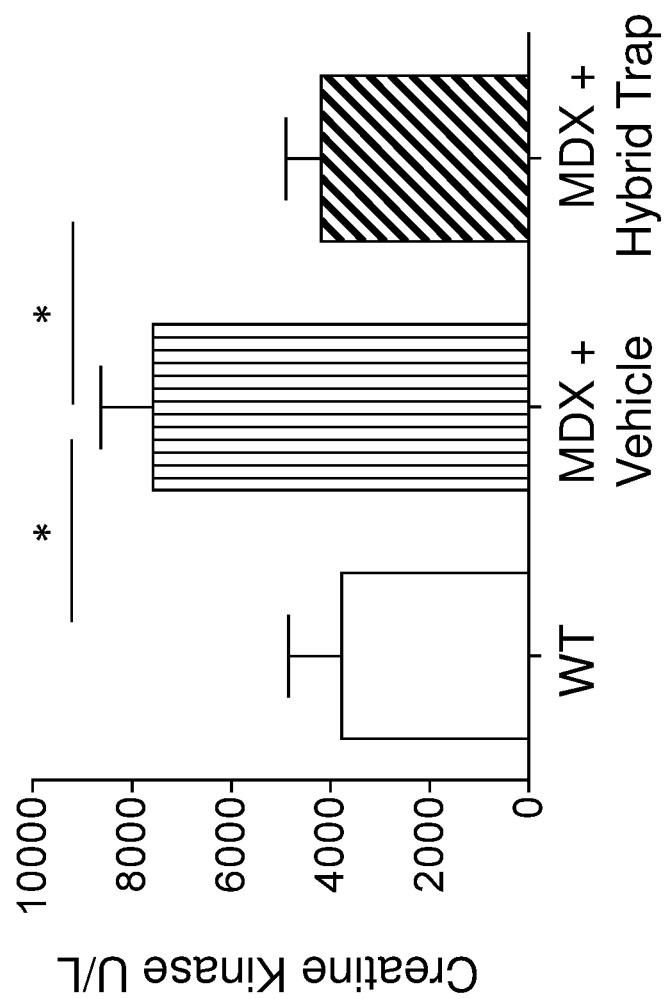
FIG. 27 illustrates the effect of subcutaneous administration of hybrid ActRIIB ligand trap (Hybrid Trap) proteins on circulating creatine kinase (CK) levels in MDX mice. MDX mice were treated with PBS or with Hybrid Trap (AG-0027; SEQ ID NO: 29) at 10 mg/kg, SC, weekly, for 8 weeks. Age-matched wild type mice were used as the normal control. Serum CK levels were measured in age-matched wild type mice (WT) and in MDX mice treated with PBS (MDX+PBS) or Hybrid Trap (Hybrid Trap+PBS). *: P<0.05, Student's t-test. n=8 per group. Error bars represent standard deviation.
Figure 28:
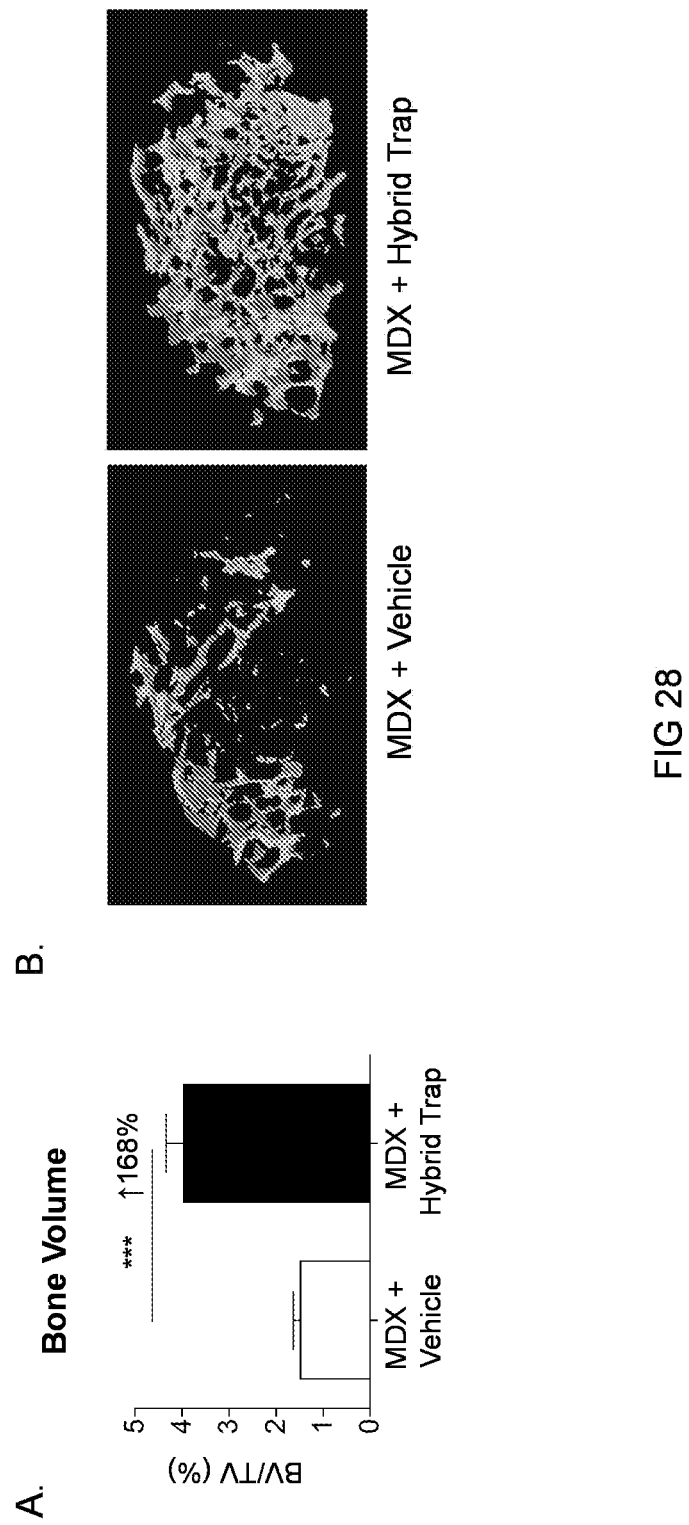
FIG. 28 shows the results of micro-CT analysis of trabecular bone density changes in the distal femur resulting from hybrid ActRIIB ligand trap (Hybrid Trap) treatment. MDX mice were treated with PBS (MDX+PBS) or Hybrid Trap (AG-0027; SEQ ID NO: 29) (MDX+Hybrid Trap) at 10 mg/kg, SC, weekly, for 8 weeks. A. Bone volume (BV/TV, %) of the distal femur in PBS- and Hybrid Trap-treated groups. Student's t-test was used for statistical analysis. ***: P<0.001. n=8 per group. Error bars represent standard deviation. B. Representative images of the distal femur trabecular architectures of PBS- and Hybrid Trap-treated groups.
Figure 29:
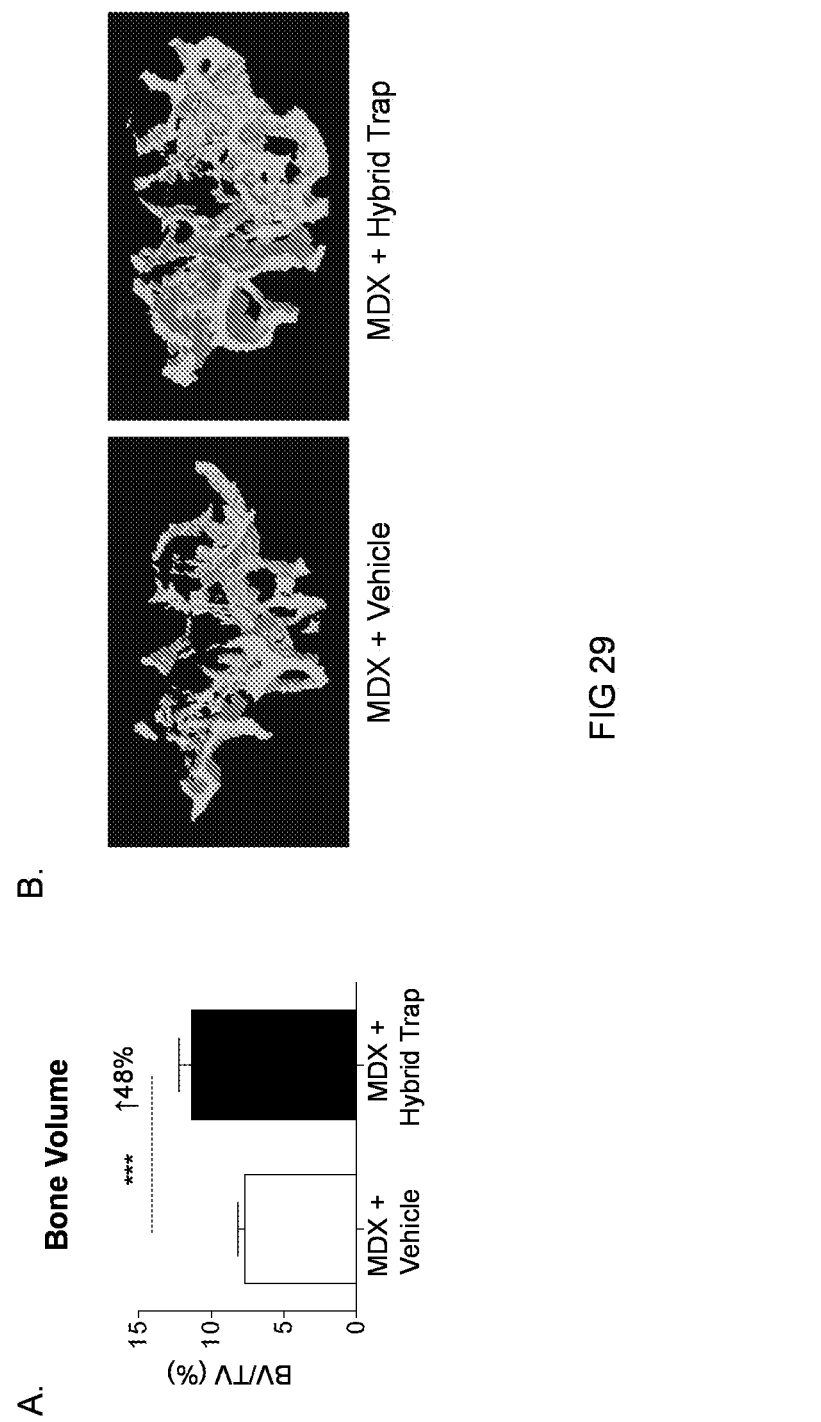
FIG. 29 shows the results of micro-CT analysis of trabecular bone density changes in the lumbar spine resulting from hybrid ActRIIB ligand trap (Hybrid Trap) treatment. MDX mice were treated with PBS (MDX+PBS) or Hybrid Trap (AG-0027; SEQ ID NO: 29) (MDX+Hybrid Trap) at 10 mg/kg, SC, weekly, for 8 weeks. A. Bone volume (BV/TV, %) of the lumbar spine in PBS- and Hybrid Trap-treated groups. Student's t-test was used for statistical analysis. ***: $P<0.001$. n=8 per group. Error bars represent standard deviation. B. Representative images of the lumbar spine trabecular architectures of PBS- and Hybrid Trap-treated groups.

[0317] 4-week-old male C57BL/10ScSn-Dmdmdx/J (mdx) and age-matched C57BL/10ScSn wild-type mice are purchased from Jackson Laboratories (Bar Harbor, ME). The mdx mice are separated into body weight-balanced groups according to their body weights and subsequently treated with AG-0027 (n=8) at dose of 10 mg/kg or with sterile PBS injections (n=8) administered subcutaneously once per week for 12 weeks. Age-matched C57BL/10ScSn mice (n=6) are used as untreated wild-type controls. The mice are weighed twice per week longitudinally and body composition is determined at beginning (week 1) and end of the study (week 12). Forelimb grip strength is assessed weekly using a BIOSEB's grip strength meter (Bioseb) by placing the animal on a horizontal grid and allowing it to pull away from the experimenter by using its forelimbs. At the end of the study, animals are euthanized using CO2, and the individual tissues, including the lean carcass, quadriceps, gastrocnemius, soleus and diaphragm muscles, are collected and weighed. Blood serum samples are collected from all experimental mice via cardiac puncture to quantify creatine kinase (CK) levels using Pointe Scientific Creatine Kinase test kit (Fisher Scientific). Data indicates that hybrid trap proteins (AG-0027 and AG-0014) effectively enhanced body weight gain, muscle mass and grip strength in the MDX mice (FIGS. 24 and 25). As shown in FIG. 24, subcutaneous administration of hybrid trap proteins (AG-0027 and AG-0014) led to sustained increase in body weight in the MDX mice in a statistically significant manner. The treatment resulted in marked and statistically significant increases in the mass of hindlimb muscles of the MDX mice (gastrocnemius, soleus and quadriceps) by 18%-36% beyond the vehicle-treated controls (see FIG. 25). In addition, the treatment significantly increased the grip strength of the MDX mice by 47-56%. The treatment also resulted in a dramatic and statistically significant reduction in serum CK levels in mdx mice (see FIG. 27), indicating that the treatment improved muscle repair and reduced muscle damage. Moreover, microCT analysis revealed that the treatment increased the trabecular bone volume by 168% in the distal femur and 48% in the lumbar spine in the MDX mice (see FIGS. 28 and 29). Thus, hybrid ActRIIB ligand trap proteins such as AG-0014 and AG-0027 are able to promote muscle growth, increase muscle strength, improve muscle repair and enhance bone density in MDX mice. Taken together, these data indicate that hybrid ActRIIB ligand trap proteins such as AG-0014 and AG-0027 have therapeutic potential to combat muscular dystrophy, including, but not limited to, Duchenne's muscular dystrophy.

EXAMPLE 15

The activins (activin A, activin B and activin AB) are upregulated in many inflammatory disease states. Elevated activins in circulation play an important role in inflammation. In this Example, the anti-inflammatory effect of AG-0027 (SEQ ID NO: 29) is examined using a mouse model of endotoxemia wherein the ability of AG-0027 to attenuate the induction of proinflammatory cytokines and mortality induced by lipopolysaccharide (LPS) is determined.

To examine the serum proinflammatory cytokine levels, four-week-old male BALB/c mice (Charles River Laboratory) are randomly grouped into 3 groups (n=8) to receive vehicle (PBS pH 7.4) or AG-0027 treatment. For baseline control, the $1^{st}$ group of mice with no treatment is sacrificed with $CO_2$ and the basal serum cytokine levels are analyzed. The $2^{nd}$ and $3^{rd}$ groups are given one subcutaneous injection of AG-0027 (20 mg/kg) or vehicle one hour prior to LPS immunization. LPS (400 μg/kg) is then injected i.p. one hour later. Ninety minutes after LPS injection, all the animals are euthanized with $CO_2$ to collect blood samples and serum levels of proinflammatory cytokines including activin A, TNF-alpha, IL-6 and IL-17 are determined by Luminex assays. To evaluate the protective effect of hybrid ActRIIB ligand trap against LPS-induced endotoxemia, 40 male BALB/c mice are randomly allocated into control group and AG-0027-treated group (n=20). One hour before LPS immunization, one group is subcutaneously injected with AG-0027 (20 mg/kg) and the other with vehicle. One hour after treatment, both groups are injected with LPS (30 mg/kg, i.p.) and the survival rates of mice are monitored twice daily starting immediately after LPS administration until 7 days post the LPS injection. Data indicates that pharmacological sequestration of activins is able to attenuate the LPS-mediated induction of proinflammatory cytokines and to reduce mortality rate in mice with lipopolysaccharide-induced endotoxemia. Therefore, hybrid ActRIIB ligand trap proteins like AG-0027 have therapeutic potential for treating inflammatory diseases.

EXAMPLE 16

Fibrosis is a serious and progressive disease condition affecting many different organs, including lung, kidney, heart, liver, bone marrow, GI tract, skin and skeletal muscle and can cause organ failure. Activation of activin-Smad2/3 signaling pathway has been implicated in pathogenesis of fibrosis. In this Example, the therapeutic potential of AG-0027 (SEQ ID NO: 29) is examined for its ability to counter fibrosis in mice with bleomycin-induced lung fibrosis, a disease model widely used for studying potential fibrosis therapies.

Lung fibrosis is induced in 6-week-old male C57BL/6 mice (Charles River Laboratory) with an intratracheal instillation of bleomycin (Calbiochem) at the dosage of 3 U/kg. Half of the mice are then treated with AG-0027 at 10 mg/kg one day after bleomycin instillation and again on days 5, 9, and 12, and the other half of the mice are treated with vehicle (PBS, pH 7.4) (n=8) on the same days. As normal control, age-matched male C57BL/6 mice (n=6) are treated with vehicle. On day 14, the mice are euthanized. Blood samples and lung tissues are harvested to quantify the severity of fibrosis by histological examination of fibrosis scores and measurement of hydroxyproline levels and collagen contents. Data suggests that blocking the actions of activins can effectively attenuate bleomycin-induced fibrosis. Therefore, hybrid ActRIIB ligand trap proteins like AG-0027 appear to offer therapeutic potential for the treatment of fibrotic diseases.

EXAMPLE 17

Osteogenesis imperfecta (OI) is a highly debilitating genetic disease characterized by brittle bones, frequent fractures and disuse muscle atrophy. It has been shown that activation of the Smad2/3 signaling pathway may play an important part in pathogenesis and progression of OI. In this Example, the effectiveness of AG-0027 (SEQ ID NO: 29) in treating bone loss and disuse muscle atrophy in osteogenesis imperfecta is evaluated.

Figure 30:
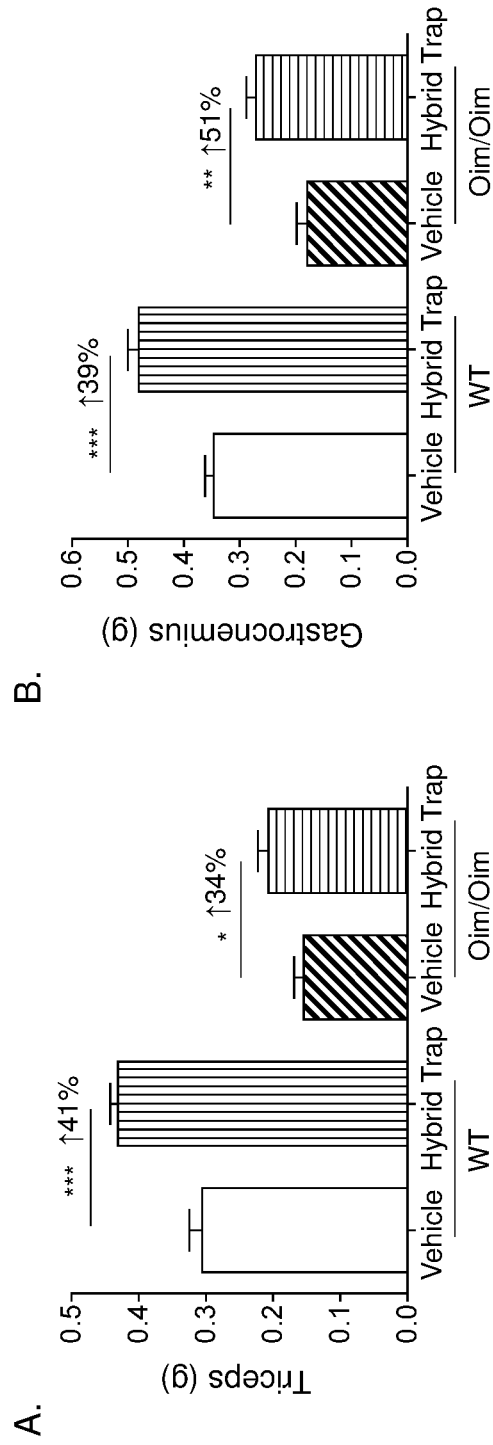
FIG. 30 shows the effect of hybrid ActRIIB ligand trap (Hybrid Trap) on muscle mass in wild type and oim/oim (type III osteogenesis imperfecta) mice. Eight-week-old wild type control mice and oim/oim mice were treated with PBS or Hybrid Trap (AG-0027; SEQ ID NO: 29) for 6 weeks. Triceps (A) and gastrocnemius muscle (B) weights were recorded during terminal necropsy. Statistical analysis was performed using Student's t-test. *: $P<0.05$; : $P<0.01$; *: $P<0.001$. n=9-12 per group. Error bars represent standard deviation.
Figure 31:
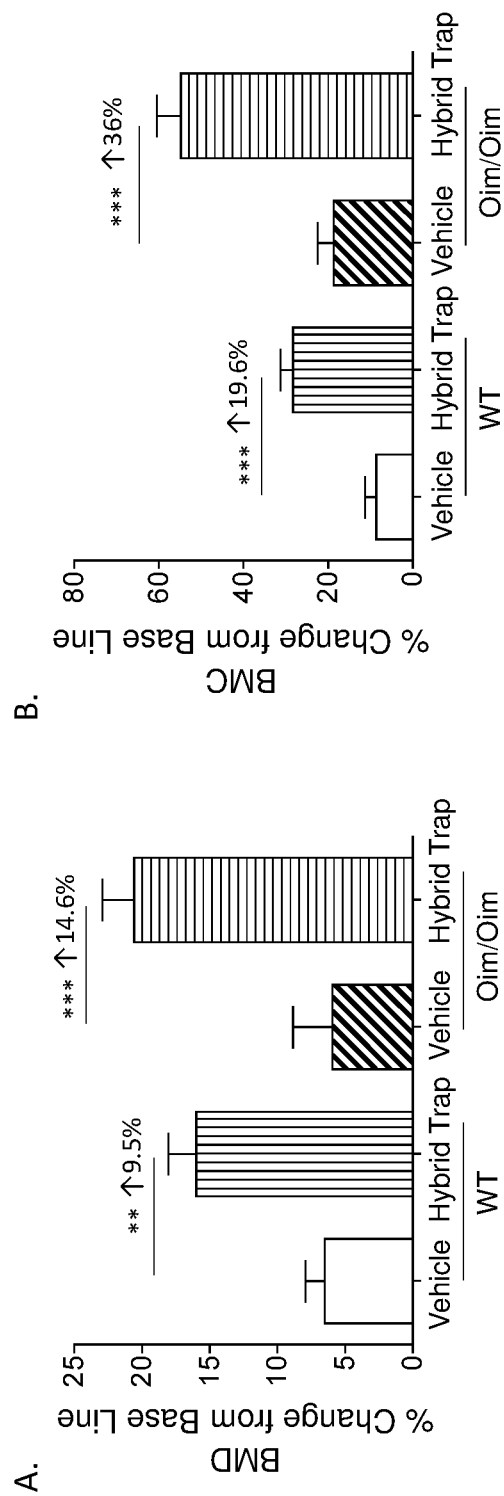
FIG. 31 shows the results of dual-energy X-ray absorptiometry (DEXA) analysis of the changes in BMD and BMC in wild type and oim/oim mice resulting from hybrid ActRIIB ligand trap (Hybrid Trap) treatment. Eight-week-old wild type control mice and oim/oim mice were treated with PBS or Hybrid Trap (AG-0027; SEQ ID NO: 29) for 6 weeks. DEXA scans on BMD (A) and BMC (B) were conducted immediately before and after the 6-week treatment with PBS or Hybrid Trap. Statistical analysis was performed using Student's t-test. : $P<0.01$; *: $P<0.001$. n=9-12 per group. Error bars represent standard deviation.
Figure 32:
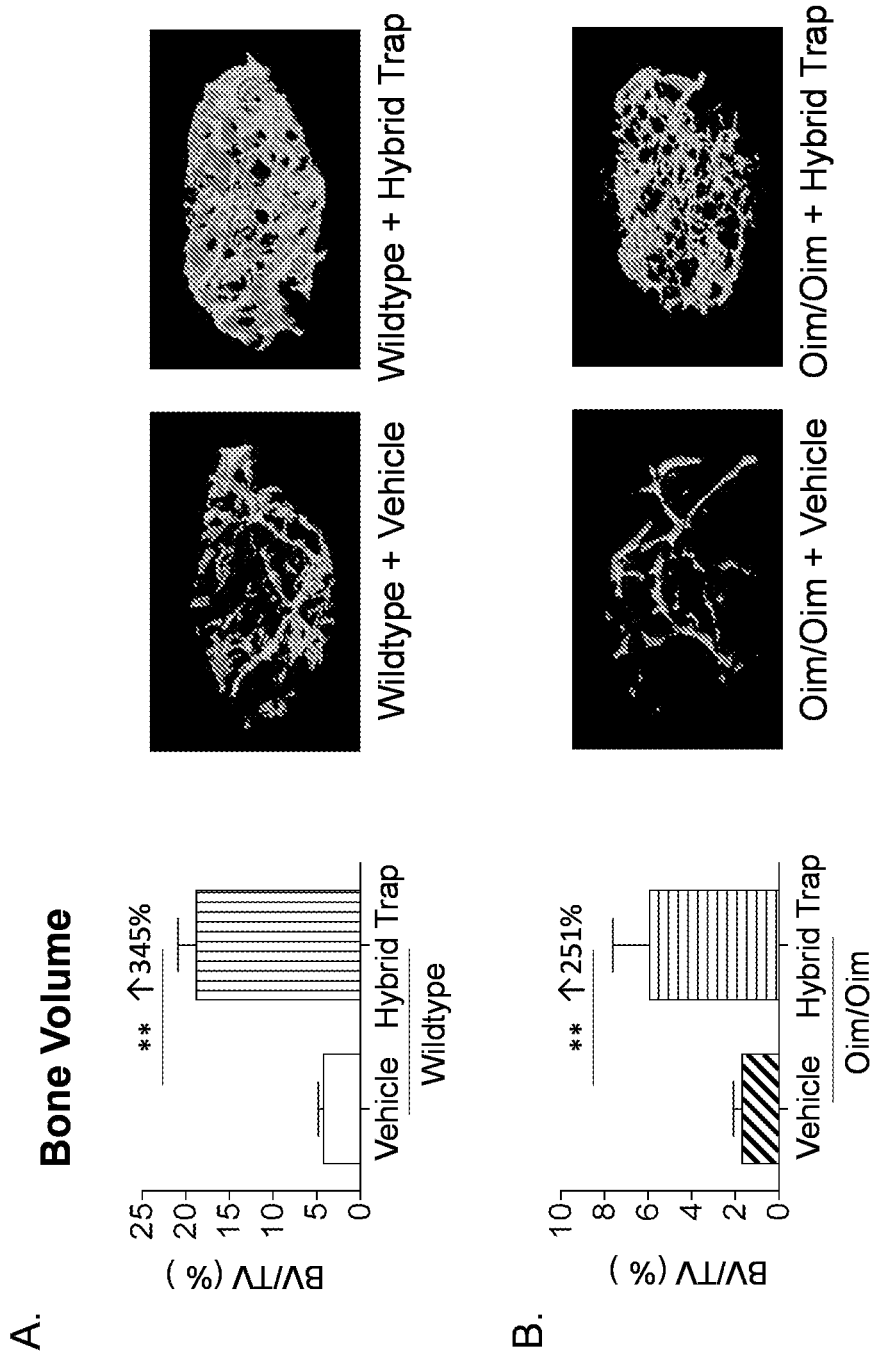
FIG. 32 shows the results of micro-CT analysis of the changes in trabecular bone density in the distal femur resulting from hybrid ActRIIB ligand trap (Hybrid Trap) treatment. Eight-week-old wild type control mice and oim/oim mice were treated with PBS or Hybrid Trap (AG-0027; SEQ ID NO: 29) for 6 weeks. Data illustrate bone volume fracture (BV/TV %) as well as the representative microCT images of trabecular architecture in the distal femur in PBS- and Hybrid Trap-treated wild type mice and in PBS- and Hybrid Trap-treated wildtype mice (panel A) and oim/oim mice (panel B). Student's t-test was used for statistical analysis. *: $P<0.05$; : $P<0.01$; *: $P<0.001$. Error bars represent standard deviation.
Figure 33:
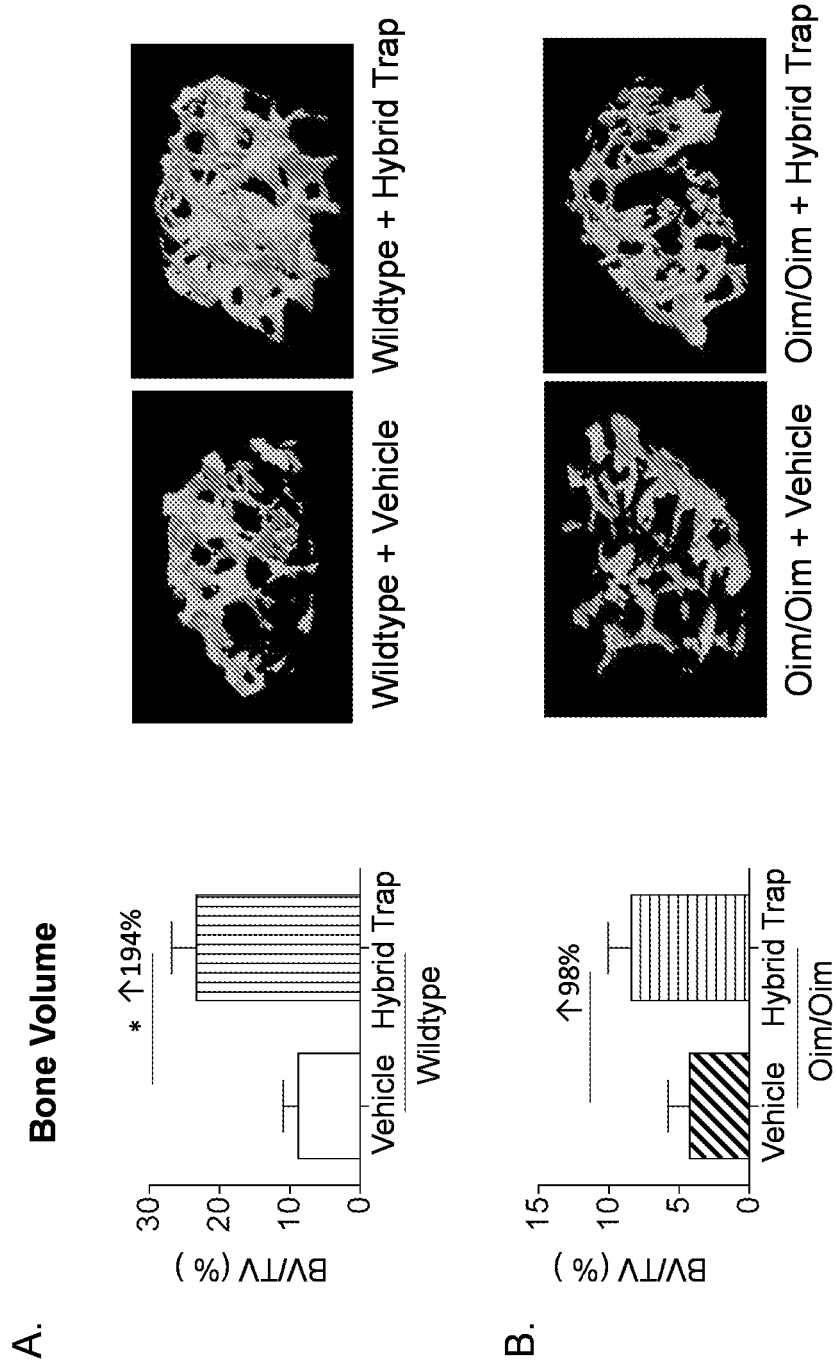
FIG. 33 shows the results of micro-CT analysis of the changes in trabecular bone density in lumbar spine resulting from hybrid ActRIIB ligand trap (Hybrid Trap) treatment. Data illustrate bone volume fracture (BV/TV %) as well as the representative microCT images of trabecular architecture in the 5$^{th}$ lumbar vertebrae in wildtype mice (panel A) and oim/oim mice (panel B) treated with PBS or Hybrid Trap (AG-0027; SEQ ID NO: 29). Student's t-test was used for statistical analysis. *: $P<0.05$; : $P<0.01$; *: $P<0.001$. Error bars represent standard deviation.
Figure 34:
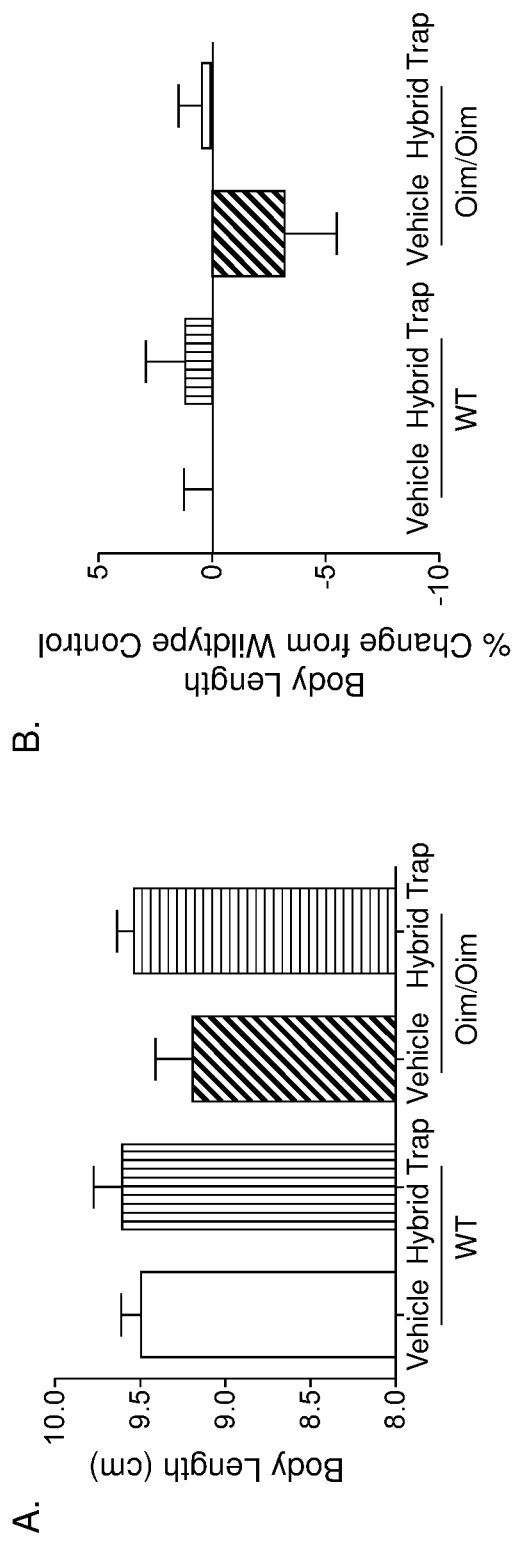
FIG. 34 illustrates the effect of hybrid ActRIIB ligand trap (Hybrid Trap) treatment on body length in oim/oim mice. The body lengths of oim/oim mice and age-matched wild type control mice were measured after 6-week treatment with PBS or Hybrid Trap (AG-0027; SEQ ID NO: 29). A. Body length in wild type and oim/oim mice after 6-week treatment. B. Body length plotted as percent change from wild type control. Error bars represent standard deviation.
Figure 35:
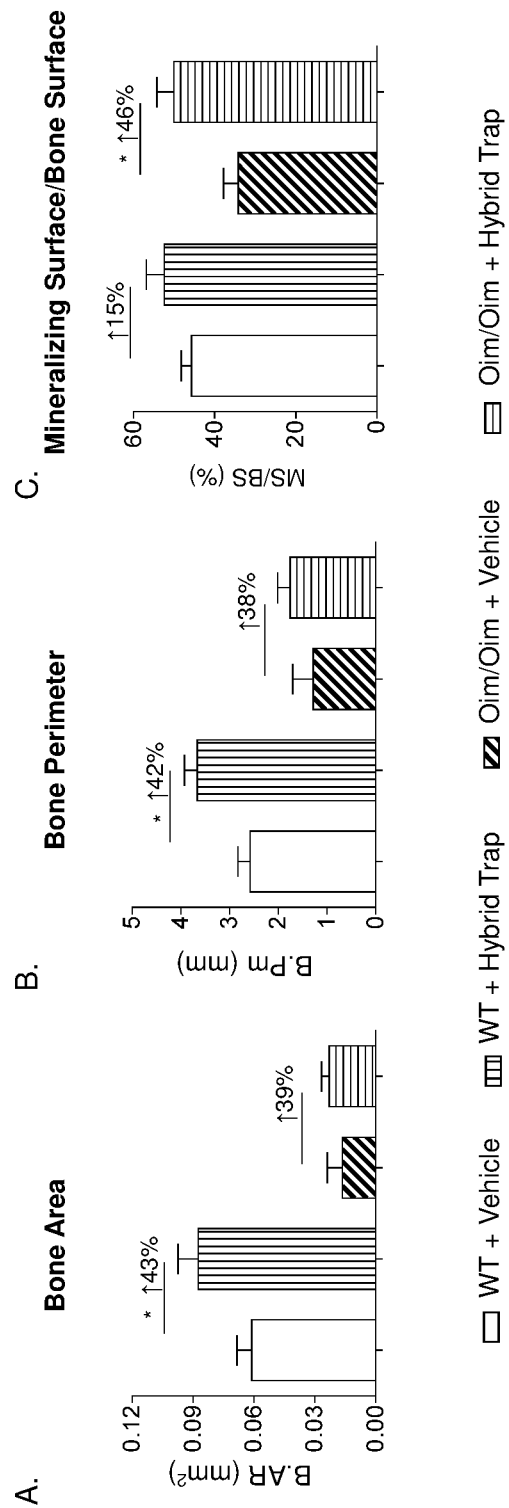
FIG. 35 shows the results of bone histomorphometry analysis of the effect of hybrid ActRIIB ligand trap (Hybrid Trap) treatment on Bone Area (A), Bone Perimeter (B) and Mineralizing Surface/Bone Surface Ratio (C) in the distal femurs. Bone histomorphometry analysis was performed after 6-week treatment with PBS or Hybrid Trap (AG-0027; SEQ ID NO: 29).
Figure 36:
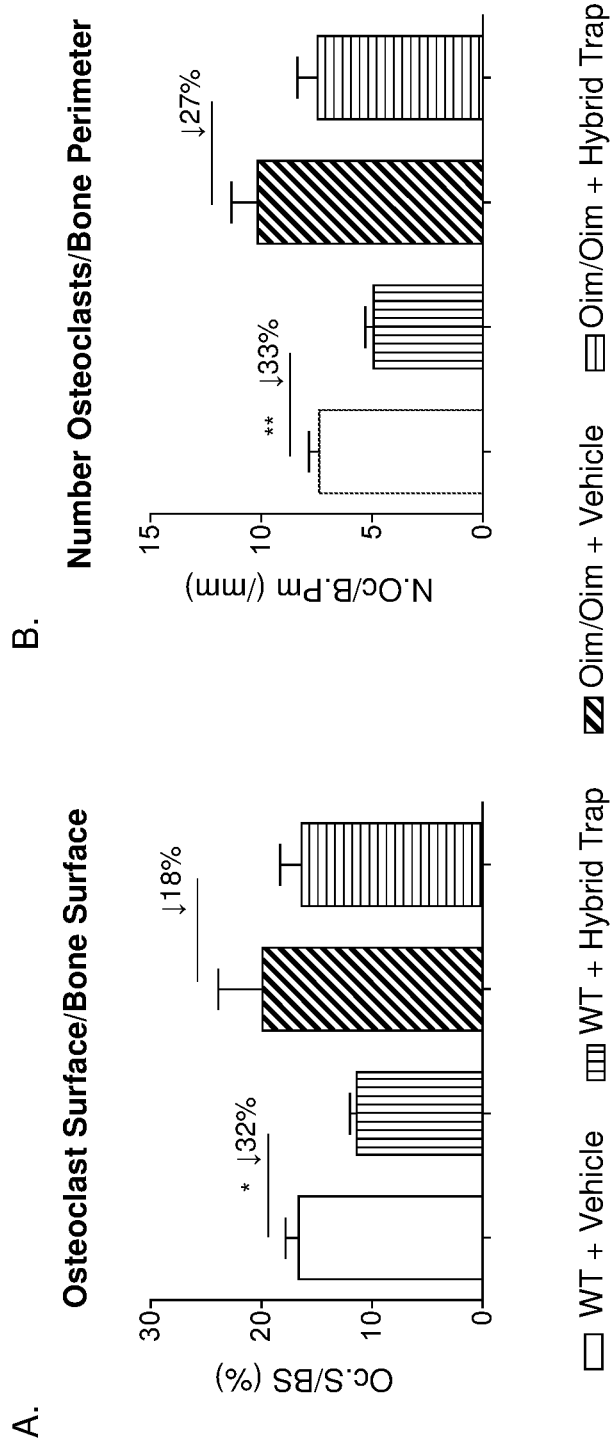
FIG. 36 shows the results of bone histomorphometry analysis of the effect of hybrid ActRIIB ligand trap (Hybrid Trap) treatment on Osteoclast/Bone Surface Ratio (A) and Number of Osteoclasts/Bone Perimeter Ratio (B) in the distal femurs. Bone histomorphometry analysis was performed after 6-week treatment with PBS or Hybrid Trap (AG-0027; SEQ ID NO: 29).

Homozygous B6C3Fe a/a Col1a2oim/J mice, a preclinical disease model of OI, are investigated. Specifically, eight-week-old male homozygous of B6C3Fe a/a Col1a2oim/J oim/oim mice (OI mice) and age-matched wild-type littermate normal control mice are obtained from Jackson Laboratory (Bar Harbor, ME, USA). The OI mice are grouped into two groups based on randomization of body weights as well as of the bone mass measured by dual energy X-ray absorptiometry (DEXA). 24 homozygous Col1a2oim mice (n=12 per group) are treated with AG-0027 (15 mg/kg, i.p.) or with vehicle (PBS, pH7.4) once per week for 6 weeks. As controls, 20 wild-type littermate control mice (n=10 per group) are treated with AG-0027 (15 mg/kg, i.p.) or vehicle once per week for 6 weeks. Body weights are longitudinally measured weekly for 6 weeks. To evaluate the bone mass, homozygous OI mice and wild-type littermate control mice are anesthetized and subjected to DEXA scans (Lunar PIXImus) to measure bone mineral density and content at the beginning and immediately before the termination of the experiment. At the end of the study, animals are euthanized using $CO_2$, the triceps, quadriceps and gastrocnemius muscles are harvested and weighed. Blood samples are collected from all experimental mice via cardiac puncture, sera are collected for analysis of bone turnover markers including bone formation markers procollagen type 1 N-terminal propeptide (P1NP), bone-specific alkaline phosphatase (BAP) and osteocalcin (OC) and bone resorption markers such as C-telopeptide of type 1 collagen (CTX-1). Femurs and fourth lumbar vertebras are collected and the bone volumes are assessed using a microtomographic imaging system (μCT, Skyscan, Kontich, Belgium). Data demonstrate that subcutaneous administration of hybrid ActRIIB ligand trap protein is able to dramatically enhance both muscle growth and bone formation in the OI mice (oim/oim mice). Treatment with AG-0027 (SEQ ID NO: 29) significantly increased skeletal muscle mass by 34% in the triceps and 51% in the gastrocnemius in the OI mice (see FIG. 30). Moreover, as revealed by DEXA scans, the treatment dramatically increased BMD and BMC significantly by 14.6% and 36%, respectively (see FIG. 31). Moreover, as shown by microCT analysis, the treatment increased the trabecular bone volume by 251% in the distal femur and 98% in the lumbar spine in the OI mice (oim/oim mice) (see FIGS. 32 and 33). Remarkably, with the improvements in muscle mass and bone mass, the treatment also appeared to have normalized the short stature by improving the body length of the OI mice (FIG. 34). Thus, pharmacological inhibition of myostatin/activin-Smad2/3 signaling with hybrid ActRIIB ligand trap AG-0027 is found to be highly effective in reversing bone loss and disuse muscle atrophy as well as in improving short stature in the OI mice. Therefore, hybrid ActRIIB ligand trap proteins like AG-0027 hold therapeutic potential for the treatment of OI.

The collective teachings of the present disclosure demonstrates that the novel hybrid ActRIIB ligand trap proteins described herein potently bind and neutralize multiple atrophy-inducing cytokines. And, importantly, the hybrid ActRIIB ligand trap proteins have dramatically improved selectivity for muscle, i.e, while potently blocking the actions of muscle atrophy-inducing cytokines, they leave the signaling of non-muscle related cytokines intact, thus maintaining the normal physiological functioning of non-muscle cells. As stated above, BMP plays an important role in a number of physiological processes and BMP9 signaling has been shown to be essential in maintaining normal blood vasculature/permeability. By sparing BMP9 signaling and preferentially antagonizing myostatin and activin signaling, the hybrid ActRIIB ligand trap proteins of the present disclosure offer a more effective and safer treatment than existing soluble ActRIIB proteins, which potently neutralize BMP-9, i.e., by selectively targeting multiple atrophy-inducing cytokines in parallel and by avoiding interfering with the signaling of non-muscle related cytokines, these hybrid ActRIIB ligand trap proteins represent a class of clinical candidates armed with a superior muscle growth efficacy and an improved safety profile and thereby it offers the potential to become a best-in-class treatment for combating muscle wasting and/or bone disorders associated with the development of a number of chronic, neurological, genetic, inflammatory, fibrotic or infectious pathologies.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

SEQUENCE LISTING

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is the amino acid sequence of a truncated wild-type human ActRIIB-ECD polypeptide.

SEQ ID NO: 2 is the amino acid sequence of a truncated wild-type human ActRIIA-ECD polypeptide.

SEQ ID NOS: 3-37 are the amino acid sequences of various hybrid soluble ActRIIB-ECD polypeptides.

SEQ ID NO: 38 is the amino acid sequence of a human immunoglobulin gamma-1 (IgG1) heavy chain constant region SEQ ID NO: 39 is the amino acid sequence of an IgG1 Fc Domain SEQ ID NO: 40 is the amino acid sequence of a human immunoglobulin gamma-2 chain heavy constant region SEQ ID NO: 41 is the amino acid sequence of an IgG2 Fc Domain SEQ ID NO: 42 is the amino acid sequence of a human immunoglobulin gamma-4 chain heavy constant region SEQ ID NO: 43 is the amino acid sequence of an IgG4 Fc Domain SEQ ID NO: 44 is the amino acid sequence of peptide linker.

SEQ ID NO: 45 is the full length amino acid sequence of Human ActRIIB polypeptide SEQ ID NO: 46 is the amino acid sequence of wild-type human ActRIIB extracellular domain (19-134 of SEQ ID NO: 45)

SEQ ID NO: 47 is the full length amino acid sequence of Human ActRIIA polypeptide SEQ ID NO: 48 is the amino acid sequence of wild-type human ActRIIA extracellular domain (20-135 of SEQ ID NO: 47)

SEQ ID NO: 49 is the amino acid sequence of a ActRIIB native signal peptide

SEQ ID NO: 50 is the amino acid sequence of an Immunoglobulin light chain signal peptide.

SEQ ID NOS: 51-117 are the amino acid sequences of various hybrid soluble ActRIIB-ECD polypeptides.

SEQ ID NO: 118 is the amino acid sequence of peptide linker.

```
                       SEQUENCE LISTINGS

Truncated wild-type ActRIIB-ECD
                                                       (SEQ ID NO: 1)
ETRECIYYNANWELERTNQSGLERCEGEQDKRLHCYASWRNSSGTIELVKKGCWLDDFNCYD

RQECVATEENPQVYFCCCEGNFCNERFTHLPEAGGPEVTYEPPPTAPT

Truncated wild-type ActRIIA-ECD
                                                       (SEQ ID NO: 2)
ETQECLFFNANWEKDRTNQTGVEPCYGDKDKRRHCFATWKNISGSIEIVKQGCWLDDINCYD

RTDCVEKKDSPEVYFCCCEGNMCNEKFSYFPEMEVTQPTSNPVTPKPP

Hybrid hu-ActRIIB-ECD (AG-0001)
                                                       (SEQ ID NO: 3)
ETRECIYYNANWELERTNQSGLERCYGDKDKRRHCYASWRNSSGTIELVKKGCWLDDINCYD

RTDCVEKKDSPEVYFCCCEGNFCNERFTHLPEAGGPEVTYEPPPTAPT

Hybrid hu-ActRIIB-ECD (AG-0002)
                                                       (SEQ ID NO: 4)
ETRECIYYNANWELERTNQSGLERCYGDKDKRRHCYASWRNSSGTIELVKKGCWLDDFNCYD

RTDCVEKKDSPEVYFCCCEGNFCNERFTHLPEAGGPEVTYEPPPTAPT

Hybrid hu-ActRIIB-ECD (AG-0003)
                                                       (SEQ ID NO: 5)
ETRECIYYNANWELERTNQSGLERCEGEQDKRLHCYASWRNSSGTIELVKKGCWLDDINCYD

RTDCVEKKDSPEVYFCCCEGNFCNERFTHLPEAGGPEVTYEPPPTAPT

Hybrid hu-ActRIIB-ECD (AG-0004)
                                                       (SEQ ID NO: 6)
ETRECIYYNANWELERTNQSGLERCEGEQDKRLHCYASWRNSSGTIELVKKGCWLDDINCYD

RTDCVEKKDSPQVYFCCCEGNFCNERFTHLPEAGGPEVTYEPPPTAPT

Hybrid hu-ActRIIB-ECD (AG-0005)
                                                       (SEQ ID NO: 7)
ETRECIYYNANWELERTNQSGLERCEGEQDKRLHCYASWRNSSGTIELVKKGCWLDDFNCYD

RTDCVEKKDSPQVYFCCCEGNFCNERFTHLPEAGGPEVTYEPPPTAPT

Hybrid hu-ActRIIB-ECD (AG-0006)
                                                       (SEQ ID NO: 8)
ETRECIYYNANWELERTNQSGLERCEGEQDKRLHCYASWRNSSGTIELVKKGCWLDDFNCYD

RTDCVEKKDSPEVYFCCCEGNFCNERFTHLPEAGGPEVTYEPPPTAPT
```

SEQUENCE LISTINGS

Hybrid hu-ActRIIB-ECD (AG-0007)  (SEQ ID NO: 9)
ETRECIYYNANWELERTNQSGLERCEGEQDKRLHCYASWRNSSGTIELVKKGCWLDDFNCYD
RQECVEKKDSPEVYFCCCEGNFCNERFTHLPEAGGPEVTYEPPPTAPT Hybrid hu-ActRIIB-ECD (AG-0008)  (SEQ ID NO: 10)
ETRECIYYNANWELERTNQSGLERCEGEQDKRLHCYASWRNSSGTIELVKKGCWLDDFNCYD
RQECVEKKDSPQVYFCCCEGNFCNERFTHLPEAGGPEVTYEPPPTAPT Hybrid human ActRIIA-ECD (AG-0009)  (SEQ ID NO: 11)
ETRECIYYNANWELERTNQSGLERCEGEQDKRLHCYASWRNSSGTIELVKKGCWLDDINCYD
RQECVEKKDSPEVYFCCCEGNFCNERFTHLPEAGGPEVTYEPPPTAPT Hybrid hu-ActRIIB-ECD (AG-0010)  (SEQ ID NO: 12)
ETRECIYYNANWELERTNQSGLERCEGEQDKRLHCYASWRNSSGTIELVKKGCWLDDFNCYD
RTDCVEKKDSPEVYFCCCEGNMCNERFTHLPEAGGPEVTYEPPPTAPT Hybrid hu-ActRIIB-ECD (AG-0011)  (SEQ ID NO: 13)
ETRECIYYNANWELERTNQSGLERCEGDQDKRLHCYASWRNSSGTIELVKKGCWLDDFNCYD
RQECVEKKDSPEVYFCCCEGNMCNERFTHLPEAGGPEVTYEPPPTAPT Hybrid hu-ActRIIB-ECD (AG-0012)  (SEQ ID NO: 14)
ETQECIYYNANWEKDRTNQTGVEPCYGDKDKRRHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0013)  (SEQ ID NO: 15)
ETQECIYYNANWEKDRTNQTGVEPCEGDQDKRLHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0014)  (SEQ ID NO: 16)
ETRECIYYNANWELERTNQSGLERCYGDKDKRRHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0015)  (SEQ ID NO: 17)
ETRECIYYNANWEKDRTNQTGVEPCEGDQDKRLHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0016)  (SEQ ID NO: 18)
ETQECIYYNANWEKDRTNQTGVEPCEGDQDKRLHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0017)  (SEQ ID NO: 19)
ETQECIYYNANWEKDRTNQTGLERCEGEQDKRLHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0018)  (SEQ ID NO: 20)
ETQECIYYNANWEKDRTNQSGLERCEGEQDKRLHCYASWRNSSGTIELVKKGCWLDDFNCYD
RQECVATEENPQVYFCCCEGNFCNERFTHLPEAGGPEVTYEPPPTAPT

| SEQUENCE LISTINGS |
| --- |

Hybrid hu-ActRIIB-ECD (AG-0019)
(SEQ ID NO: 21)
ETRECIYYNANWEKDRTNQSGLERCEGEQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD (AG-0020)
(SEQ ID NO: 22)
ETQECIYYNANWELERTNQSGLERCEGEQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD (AG-0021)
(SEQ ID NO: 23)
ETRECIYYNANWELERTNQSGLERCEGEQDKRLHCFATWRNSSGTIELVKQGCWLDDFNCYD

RQECVATEENPQVYFCCCEGNFCNERFTHLPEAGGPEVTYEPPPTAPT

Hybrid hu-ActRIIB-ECD (AG-0022)
(SEQ ID NO: 24)
ETRECIYYNANWELERTNQSGLERCYGDKDKRRHCYASWRNSSGTIELVKKGCWLDDINCYD

RQECVATEENPQVYFCCCEGNFCNERFTHLPEAGGPEVTYEPPPTAPT

Hybrid hu-ActRIIB-ECD (AG-0023)
(SEQ ID NO: 25)
ETRECIYYNANWELERTNQSGLERCEGEQDKRLHCYASWRNSSGTIELVKKGCWLDDFNCYD

RQECVATKENPQVYFCCCEGNFCNERFTHLPEAGGPEVTYEPPPTAPT

Hybrid hu-ActRIIB-ECD (AG-0024)
(SEQ ID NO: 26)
ETRECIYYNANWELERTNQSGLERCEGEQDKRLHCYASWRNSSGTIELVKKGCWLDDINCYD

RQECVATEENPQVYFCCCEGNFCNERFTHLPEAGGPEVTYEPPPTAPT

Hybrid hu-ActRIIB-ECD (AG-0025)
(SEQ ID NO: 27)
ETRECIYYNANWELERTNQSGLERCEGEQDKRLHCYASWRNSSGTIELVKKGCWLDDINCYD

RQECVATKENPQVYFCCCEGNFCNERFTHLPEAGGPEVTYEPPPTAPT

Hybrid hu-ActRIIB-ECD (AG-0026)
(SEQ ID NO: 28)
ETRECIYYNANWELERTNQSGLERCEGDKDKRLHCYASWRNSSGTIELVKKGCWLDDINCYD

RQECVATKENPQVYFCCCEGNFCNERFTHLPEAGGPEVTYEPPPTAPT

Hybrid hu-ActRIIB-ECD (AG-0027)
(SEQ ID NO: 29)
ETRECIYYNANWELERTNQSGLERCEGDQDKRLHCYASWRNSSGTIELVKKGCWLDDINCYD

RQECVATKENPQVYFCCCEGNFCNERFTHLPEAGGPEVTYEPPPTAPT

Hybrid hu-ActRIIB-ECD (AG-0028)
(SEQ ID NO: 30)
ETRECIYYNANWELERTNQSGLERCEGDQDKRLHCYASWRNSSGTIELVKKGCWLDDFNCYD

RQECVATKENPQVYFCCCEGNFCNERFTHLPEAGGPEVTYEPPPTAPT

Hybrid hu-ActRIIB-ECD (AG-0029)
(SEQ ID NO: 31)
ETRECIYYNANWELERTNQSGLERCEGDQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD (AG-0030)
(SEQ ID NO: 32)
ETRECIYYNANWELERTNQSGLERCYGDKDKRRHCYASWRNSSGTIELVKKGCWLDDINCYD

RQECVEKKDSPEVYFCCCEGNFCNERFTHLPEAGGPEVTYEPPPTAPT

SEQUENCE LISTINGS

Hybrid hu-ActRIIB-ECD (AG-0031)
(SEQ ID NO: 33)
ETRECIFFNANWEKDRTNQTGVEPCEGEQDKRLHCYASWRNSSGTIELVKKGCWLDDFNCYD
RQECVATEENPQVYFCCCEGNFCNERFTHLPEAGGPEVTYEPPPTAPT Hybrid hu-ActRIIB-ECD (AG-0032)
(SEQ ID NO: 34)
ETRECIYYNANWELERTNQSGLERCEGEQDKRLHCFATWKNISGSIELVKQGCWLDDFNCYD
RQECVATEENPQVYFCCCEGNFCNERFTHLPEAGGPEVTYEPPPTAPT Hybrid hu-ActRIIB-ECD (AG-0033)
(SEQ ID NO: 35)
ETRECIYYNANWELERTNQSGLERCEGEQDKRLHCYASWRNSSGTIELVKKGCWLDDFNCYD
RTDCVATEENPQVYFCCCEGNFCNERFTHLPEAGGPEVTYEPPPTAPT Hybrid hu-ActRIIB-ECD (AG-0034)
(SEQ ID NO: 36)
ETRECIYYNANWELERTNQSGLERCEGEQDKRLHCYASWRNSSGTIELVKKGCWLDDFNCYD
RQECVATEENPQVYFCCCEGNMCNERFTHLPEAGGPEVTYEPPPTAPT Hybrid hu-ActRIIB-ECD (AG-0035)
(SEQ ID NO: 37)
ETRECIYYNANWELERTNQSGLERCEGDQDKRLHCYASWRNSSGTIELVKKGCWLDDINCYD
RQECVATEENPQVYFCCCEGNFCNERFTHLPEAGGPEVTYEPPPTAPT Human immunoglobulin gamma-1 heavy chain constant region
(SEQ ID NO: 38)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSV
MHEALHNHYTQKSLSLSPGK IgG1 Fc Domain
(SEQ ID NO: 39)
VFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSC
SVMHEALHNHYTQKSLSLSPGK Human immunoglobulin gamma-2 heavy chain constant region
(SEQ ID NO: 40)
ASTKGPSVFPLAPCSRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKNQVSLTCLVK
GFYPSDIAVEWESNGQPENNYKTTPPMLDSDGSFFLYSKLTVDKSRWQQGNVFSCSVMHEAL
HNHYTQKSLSLSPGK IgG2 Fc Domain
(SEQ ID NO: 41)
VFLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKNQV

SLTCLVKGFYPSDIAVEWESNGQPENNYKTTPPMLDSDGSFFLYSKLTVDKSRWQQGNVFCS

VMHEALHNHYTQKSLSLSPGK

Human immunoglobulin gamma-4 heavy chain constant region
(SEQ ID NO: 42)
ASTKGPSVFPLAPCSRSTSESTAALGCLVKDYFPEPVTVSWNSGALTSGVHTFPAVLQSSGL

YSLSSWTVPSSSLGTKTYTCNVDHKPSNTKVDKRVESKYGPPCPSCPAPEFLGGPSVFLFPP

KPKDTLMISRTPEVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSRWQEGNVFSCSVMHEA

LHNHYTQKSLSLSLGK

IgG4 Fc Domain
(SEQ ID NO: 43)
APEFLGGPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVDKSR

WQEGNVFSCSVMHEALHNHYTQKSLSLSLGK

Peptide Linker sequence
(SEQ ID NO: 44)
GGGGS

Full Length Amino Acid Sequence of Human ActRIIB
polypeptide
(SEQ ID NO: 45)
MTAPWVALALLWGSLCAGSGRGEAETRECIYYNANWELERTNQSGLERCEGEQDKRLHCYAS

WRNSSGTIELVKKGCWLDDFNCYDRQECVATEENPQVYFCCCEGNFCNERFTHLPEAGGPEV

TYEPPPTAPTLLTVLAYSLLPIGGLSLIVLLAFWMYRHRKPPYGHVDIHEDPGPPPPSPLVG

LKPLQLLEIKARGRFGCVWKAQLMNDFVAVKIFPLQDKQSWQSEREIFSTPGMKHENLLQFI

AAEKRGSNLEVELWLITAFHDKGSLTDYLKGNIITWNELCHVAETMSRGLSYLHEDVPWCRG

EGHKPSIAHRDFKSKNVLLKSDLTAVLADFGLAVRFEPGKPPGDTHGQVGTRRYMAPEVLEG

AINFQRDAFLRIDMYAMGLVLWELVSRCKAADGPVDEYMLPFEEEIGQHPSLEELQEVVVHK

KMRPTIKDHWLKHPGLAQLCVTIEECWDHDAEARLSAGCVEERVSLIRRSVNGTTSDCLVSL

VTSVTNVDLPPKESSI

Wild-type human ActRIIB extracellular domain
(19-134 of SEQ ID NO: 45)
(SEQ ID NO: 46)
SGRGEAETRECIYYNANWELERTNQSGLERCEGEQDKRLHCYASWRNSSGTIELVKKGCWLD

DFNCYDRQECVATEENPQVYFCCCEGNFCNERFTHLPEAGGPEVTYEPPPTAPT

Full Length Amino Acid Sequence of Human ActRIIA
polypeptide
(SEQ ID NO: 47)
MGAATKLAFAVFLISCSSGAILGRSETQECIYYNANWEKDKTNRSGIEPCYGDKDKRRHCFA

TWKNISGSIEIVKQGCWLDDINCYDRNDCIEKKDSPEVFFCCCEGNMCNERFFYFPEMEVTQ

PTSNPVTPKPPLFNTLLYSLVPIMGIAVIVLFSFWMYRHHKLAYPPVLVPTQDPGPPPPSPL

MGLKPLQLLEIKARGRFGCVWKAQLLNEYVAVKIFPIQDKQSWQNEYEIYSLPGMKHDNILQ

FIGAEKRGTSIDVDLWLITAFHEKGSLTDFLKANVVSWNELCHIAQTMARGLAYLHEDIPGL

KDGHKPAISHRDIKSKNVLLKNNLTACIADFGLALKFEAGKSAGDTHGQVGTRRYMAPEVLE

GAINFQRDAFLRIDMYAMGLVLWELASRCTASDGPVDEYMLPFEEEIGQHPSLEDMQEVVVH

```
                            SEQUENCE LISTINGS
```

KKKRPVLRECWQKHSGMAMLCETIEECWDHDAEARLSAGCVEERIIQMQKLTNIITTEDIVT

VVTMVTNVDFPPKESSL

Wild-type human ActRIIA extracellular domain
(20-135 of SEQ ID NO: 47)
                                                    (SEQ ID NO: 48)
AILGRSETQECLFFNANWEKDRTNQTGVEPCYGDKDKRRHCFATWKNISGSIEIVKQGCWLD

DINCYDRTDCVEKKDSPEVYFCCCEGNMCNEKFSYFPEMEVTQPTSNPVTPKPP

ActRIIB native signal peptide:
                                                    (SEQ ID NO: 49)
MTAPWVALALLWGSLCAG Immunoglobulin light chain signal peptide:
                                                    (SEQ ID NO: 50)
MDMRVPAQLLGLLLLWLRGARC Hybrid hu-ActRIIB-ECD
                                                    (SEQ ID NO: 51)
ETQECLFFNANWEKDRTNQSGVEPCYGDKDKRRHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 52)
ETQECLFFNANWEKDRTNQSGVEPCEGEQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 53)
ETRECLFFNANWEKDRTNQSGVEPCEGEQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 54)
ETQECLFFNANWEKDRTNQSGVEPCYGEQDKRLHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 55)
ETRECLFFNANWEKDRTNQSGVEPCYGDKDKRRHCYASWRNSSGTIELVKKGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 56)
ETRECLFFNANWEKDRTNQTGVEPCYGDKDKRRHCFATWKNISGSIEIVKQGCWLDDFNCYD

RQECVATEENPQVYFCCCEGNFCNERFTHLPEAGGPEVTYEPPPTAPT

Hybrid hu-ActRIIB-ECD
                                                    (SEQ ID NO: 57)
ETRECLFFNANWEKDRTNQTGVEPCYGDKDKRRHCFATWKNISGSIEIVKQGCWLDDINCYD

RQECVATEENPQVYFCCCEGNFCNERFTHLPEAGGPEVTYEPPPTAPT

Hybrid hu-ActRIIB-ECD
                                                    (SEQ ID NO: 58)
ETRECLFFNANWEKDRTNQTGVEPCYGDKDKRRHCFATWKNISGSIEIVKQGCWLDDINCYD

RTDCVEKKDSPEVYFCCCEGNFCNERFTHLPEAGGPEVTYEPPPTAPT

Hybrid hu-ActRIIB-ECD
                                                    (SEQ ID NO: 59)
ETQECIYYNANWELERTNQSGLERCYGDKDKRRHCFATWKNISGSIEIVKQGCWLDDINCYD

RQECVATEENPQVYFCCCEGNFCNERFTHLPEAGGPEVTYEPPPTAPT

| SEQUENCE LISTINGS |
|---|

Hybrid hu-ActRIIB-ECD
                                                              (SEQ ID NO: 60)
ETRECIYYNANWELERTNQSGLERCYGDKDKRRHCFATWKNISGSIEIVKQGCWLDDINCYD

RTDCVEKKDSPEVYFCCCEGNFCNERFTHLPEAGGPEVTYEPPPTAPT

Hybrid hu-ActRIIB-ECD
                                                              (SEQ ID NO: 61)
ETRECIYYNANWELERTNQSGLERCYGDKDKRRHCFATWKNISGSIEIVKQGCWLDDINCYD

RTDCVEKKDSPEVYFCCCEGNMCNERFTHLPEAGGPEVTYEPPPTAPT

Hybrid hu-ActRIIB-ECD
                                                              (SEQ ID NO: 62)
ETRECIYYNANWELERTNQSGLERCEGEQDKRLHCFATWKNISGSIEIVKQGCWLDDINCYD

RTDCVEKKDSPEVYFCCCEGNFCNERFTHLPEAGGPEVTYEPPPTAPT

Hybrid hu-ActRIIB-ECD
                                                              (SEQ ID NO: 63)
ETRECIYYNANWELERTNQSGLERCEGEQDKRLHCFATWKNISGSIEIVKQGCWLDDINCYD

RTDCVATEENPQVYFCCCEGNFCNERFTHLPEAGGPEVTYEPPPTAPT

Hybrid hu-ActRIIB-ECD
                                                              (SEQ ID NO: 64)
ETRECIYYNANWELERTNQSGLERCEGEQDKRLHCFATWKNISGSIEIVKQGCWLDDFNCYD

RTDCVATEENPQVYFCCCEGNFCNERFTHLPEAGGPEVTYEPPPTAPT

Hybrid hu-ActRIIB-ECD
                                                              (SEQ ID NO: 65)
ETRECIYYNANWELERTNQSGLERCEGEQDKRLHCFATWKNISGSIEIVKQGCWLDDFNCYD

RQECVATEENPQVYFCCCEGNFCNERFTHLPEAGGPEVTYEPPPTAPT

Hybrid hu-ActRIIB-ECD
                                                              (SEQ ID NO: 66)
ETQECIYYNANWELERTNQSGLERCYGDKDKRRHCYASWRNSSGTIELVKKGCWLDDINCYD

RTDCVEKKDSPEVYFCCCEGNFCNERFTHLPEAGGPEVTYEPPPTAPT

Hybrid hu-ActRIIB-ECD
                                                              (SEQ ID NO: 67)
ETQECIYYNANWELERTNQSGLERCYGDKDKRRHCYASWRNSSGTIELVKKGCWLDDINCYD

RTDCVEKKDSPEVYFCCCEGNMCNERFTHLPEAGGPEVTYEPPPTAPT

Hybrid hu-ActRIIB-ECD
                                                              (SEQ ID NO: 68)
ETQECIYYNANWELERTNQSGLERCYGDKDKRRHCFATWKNISGSIEIVKQGCWLDDINCYD

RTDCVEKKDSPEVYFCCCEGNMCNERFTHLPEAGGPEVTYEPPPTAPT

Hybrid hu-ActRIIB-ECD
                                                              (SEQ ID NO: 69)
ETQECIYYNANWELERTNQSGLERCYGDKDKRRHCFATWKNISGSIEIVKQGCWLDDINCYD

RTDCVEKKDSPEVYFCCCEGNFCNERFTHLPEAGGPEVTYEPPPTAPT

Hybrid hu-ActRIIB-ECD
                                                              (SEQ ID NO: 70)
ETRECLFFNANWEKDRTNQTGVEPCEGEQDKRLHCFATWKNISGSIEIVKQGCWLDDINCYD

RTDCVEKKDSPEVYFCCCEGNFCNERFTHLPEAGGPEVTYEPPPTAPT

Hybrid hu-ActRIIB-ECD
                                                              (SEQ ID NO: 71)
ETRECLFFNANWEKDRTNQSGVEPCEGEQDKRLHCYASWRNSSGTIELVKKGCWLDDINCYD

RTDCVEKKDSPEVYFCCCEGNFCNERFTHLPEAGGPEVTYEPPPTAPT

SEQUENCE LISTINGS

Hybrid hu-ActRIIB-ECD
(SEQ ID NO: 72)
ETRECLFFNANWEKDRTNQSGVEPCYGDKDKRRHCYASWRNSSGTIELVKKGCWLDDINCYD

RTDCVEKKDSPEVYFCCCEGNFCNERFTHLPEAGGPEVTYEPPPTAPT

Hybrid hu-ActRIIB-ECD
(SEQ ID NO: 73)
ETRECIYYNANWELERTNQSGLERCYGDKDKRRHCYASWRNSSGTIELVKKGCWLDDFNCYD

RTDCVATEENPQVYFCCCEGNFCNERFTHLPEAGGPEVTYEPPPTAPT

Hybrid hu-ActRIIB-ECD
(SEQ ID NO: 74)
ETRECIYYNANWELERTNQSGLERCYGDKDKRRHCYASWRNSSGTIELVKQGCWLDDFNCYD

RTDCVATEENPQVYFCCCEGNFCNERFTHLPEAGGPEVTYEPPPTAPT

Hybrid hu-ActRIIB-ECD
(SEQ ID NO: 75)
ETRECIYYNANWELERTNQSGLERCYGDKDKRRHCYASWRNSSGTIEIVKKGCWLDDFNCYD

RTDCVATEENPQVYFCCCEGNFCNERFTHLPEAGGPEVTYEPPPTAPT

Hybrid hu-ActRIIB-ECD
(SEQ ID NO: 76)
ETRECIYYNANWELERTNQSGLERCYGDKDKRRHCYASWRNSSGSIELVKKGCWLDDFNCYD

RTDCVATEENPQVYFCCCEGNFCNERFTHLPEAGGPEVTYEPPPTAPT

Hybrid hu-ActRIIB-ECD
(SEQ ID NO: 77)
ETRECIYYNANWELERTNQSGLERCYGDKDKRRHCYASWRNSSGSIEIVKKGCWLDDFNCYD

RTDCVATEENPQVYFCCCEGNFCNERFTHLPEAGGPEVTYEPPPTAPT

Hybrid hu-ActRIIB-ECD
(SEQ ID NO: 78)
ETRECIYYNANWELERTNQSGLERCYGDKDKRRHCYASWRNSSGSIEIVKQGCWLDDFNCYD

RTDCVATEENPQVYFCCCEGNFCNERFTHLPEAGGPEVTYEPPPTAPT

Hybrid hu-ActRIIB-ECD
(SEQ ID NO: 79)
ETRECIYYNANWELERTNQSGLERCEGEQDKRLHCYASWRNSSGTIELVKKGCWLDDFNCYD

RTDCVATEENPQVYFCCCEGNMCNERFTHLPEAGGPEVTYEPPPTAPT

Hybrid hu-ActRIIB-ECD
(SEQ ID NO: 80)
ETRECIYYNANWELERTNQSGLERCEGEQDKRLHCYASWRNSSGTIELVKKGCWLDDFNCYD

RQECVATEENPQVYFCCCEGNFCNEKFSYFPEMEVTQPTSNPVTPKPP

Hybrid hu-ActRIIB-ECD
(SEQ ID NO: 81)
ETRECIYYNANWELERTNQSGLERCEGEQDKRLHCYASWRNSSGTIELVKKGCWLDDFNCYD

RQECVATEENPQVYFCCCEGNFCNEKFSYFPQMEVTQPTSNPVTPKPP

Hybrid hu-ActRIIB-ECD
(SEQ ID NO: 82)
ETRECIYYNANWELERTNQSGLERCYGDKDKRRHCYASWRNSSGTIELVKKGCWLDDINCYD

RTDCVEKKDSPEVYFCCCEGNFCNEKFSYFPEMEVTQPTSNPVTPKPP

Hybrid hu-ActRIIB-ECD
(SEQ ID NO: 83)
ETRECIYYNANWELERTNQSGLERCYGDKDKRRHCYASWRNSSGTIELVKKGCWLDDINCYD

RTDCVEKKDSPEVYFCCCEGNFCNEKFSYFPQMEVTQPTSNPVTPKPP

SEQUENCE LISTINGS
-continued

Hybrid hu-ActRIIB-ECD
(SEQ ID NO: 84)
ETRECIYYNANWELERTNQSGLERCYGDKDKRRHCYASWRNSSGTIELVKKGCWLDDFNCYD
RQECVATEENPQVYFCCCEGNFCNEKFSYFPQMEVTQPTSNPVTPKPP Hybrid hu-ActRIIB-ECD
(SEQ ID NO: 85)
ETRECIYYNANWELERTNQSGLERCYGDKDKRRHCYASWRNSSGTIELVKQGCWLDDFNCYD
RQECVATEENPQVYFCCCEGNFCNEKFSYFPQMEVTQPTSNPVTPKPP Hybrid hu-ActRIIB-ECD
(SEQ ID NO: 86)
ETRECIYYNANWELERTNQSGLERCYGDKDKRRHCYASWRNSSGTIEIVKKGCWLDDFNCYD
RQECVATKENPQVYFCCCEGNFCNEKFSYFPQMEVTQPTSNPVTPKPP Hybrid hu-ActRIIB-ECD
(SEQ ID NO: 87)
ETRECIYYNANWELERTNQSGLERCYGDKDKRRHCYASWRNSSGSIELVKKGCWLDDFNCYD
RQECVATKENPQVYFCCCEGNFCNEKFSYFPQMEVTQPTSNPVTPKPP Hybrid hu-ActRIIB-ECD
(SEQ ID NO: 88)
ETRECIYYNANWELERTNQSGLERCEGEQDKRLHCYASWRNSSGSIELVKKGCWLDDFNCYD
RQECVATEENPQVYFCCCEGNFCNEKFSYFPQMEVTQPTSNPVTPKPP Hybrid hu-ActRIIB-ECD
(SEQ ID NO: 89)
ETRECIYYNANWELERTNQSGLERCEGEQDKRLHCYASWRNSSGTIEIVKKGCWLDDFNCYD
RQECVATEENPQVYFCCCEGNFCNEKFSYFPQMEVTQPTSNPVTPKPP Hybrid hu-ActRIIB-ECD
(SEQ ID NO: 90)
ETRECIYYNANWELERTNQSGLERCEGEQDKRLHCYASWRNSSGTIELVKQGCWLDDFNCYD
RQECVATEENPQVYFCCCEGNFCNEKFSYFPQMEVTQPTSNPVTPKPP Hybrid hu-ActRIIB-ECD
(SEQ ID NO: 91)
ETRECIYYNANWELERTNQSGLERCEGEQDKRLHCYASWRNSSGTIELVKKGCWLDDFNCYD
RQECVETEENPQVYFCCCEGNFCNEKFSYFPQMEVTQPTSNPVTPKPP Hybrid hu-ActRIIB-ECD
(SEQ ID NO: 92)
ETRECIYYNANWELERTNQSGLERCEGEQDKRLHCYASWRNSSGTIELVKKGCWLDDFNCYD
RQECVAKEENPQVYFCCCEGNFCNEKFSYFPQMEVTQPTSNPVTPKPP Hybrid hu-ActRIIB-ECD
(SEQ ID NO: 93)
ETRECIYYNANWELERTNQSGLERCEGEQDKRLHCYASWRNSSGTIELVKKGCWLDDFNCYD
RQECVATKENPQVYFCCCEGNFCNEKFSYFPQMEVTQPTSNPVTPKPP Hybrid hu-ActRIIB-ECD
(SEQ ID NO: 94)
ETRECIYYNANWELERTNQSGLERCEGEQDKRLHCYASWRNSSGTIELVKKGCWLDDFNCYD
RQECVATEDNPQVYFCCCEGNFCNEKFSYFPQMEVTQPTSNPVTPKPP Hybrid hu-ActRIIB-ECD
(SEQ ID NO: 95)
ETRECIYYNANWELERTNQSGLERCEGEQDKRLHCYASWRNSSGTIELVKKGCWLDDFNCYD
RQECVATEESPQVYFCCCEGNFCNEKFSYFPQMEVTQPTSNPVTPKPP

| SEQUENCE LISTINGS |
| --- |

Hybrid hu-ActRIIB-ECD
(SEQ ID NO: 96)
ETRECIYYNANWELERTNQSGLERCEGEQDKRLHCYASWRNSSGTIELVKKGCWLDDFNCYD

RQECVATEENPEVYFCCCEGNFCNEKFSYFPQMEVTQPTSNPVTPKPP

Hybrid hu-ActRIIB-ECD
(SEQ ID NO: 97)
ETRECIYYNANWELERTNQSGLERCEGDKDKRLHCYASWRNSSGTIELVKKGCWLDDFNCYD

RQECVETEENPQVYFCCCEGNFCNEKFSYFPQMEVTQPTSNPVTPKPP

Hybrid hu-ActRIIB-ECD
(SEQ ID NO: 98)
ETRECIYYNANWELERTNQSGLERCEGEKDKRLHCYASWRNSSGTIELVKKGCWLDDFNCYD

RQECVAKEENPQVYFCCCEGNFCNEKFSYFPQMEVTQPTSNPVTPKPP

Hybrid hu-ActRIIB-ECD
(SEQ ID NO: 99)
ETRECIYYNANWELERTNQSGLERCEGDQDKRLHCYASWRNSSGTIELVKKGCWLDDFNCYD

RQECVATKENPQVYFCCCEGNFCNEKFSYFPQMEVTQPTSNPVTPKPP

Hybrid hu-ActRIIB-ECD
(SEQ ID NO: 100)
ETRECIYYNANWELERTNQSGLERCEGDKDKRLHCYASWRNSSGTIELVKQGCWLDDFNCYD

RQECVAKKENPQVYFCCCEGNFCNEKFSYFPQMEVTQPTSNPVTPKPP

Hybrid hu-ActRIIB-ECD
(SEQ ID NO: 101)
ETRECIYYNANWELERTNQSGLERCEGDKDKRLHCYASWRNSSGTIEIVKQGCWLDDFNCYD

RQECVAEKENPQVYFCCCEGNFCNEKFSYFPQMEVTQPTSNPVTPKPP

Hybrid hu-ActRIIB-ECD
(SEQ ID NO: 102)
ETRECIYYNANWELERTNQSGLERCYGDQDKRLHCYASWRNSSGSIEIVKQGCWLDDFNCYD

RQECVAKKENPQVYFCCCEGNFCNEKFSYFPQMEVTQPTSNPVTPKPP

Hybrid hu-ActRIIB-ECD
(SEQ ID NO: 103)
ETRECIYYNANWELERTNQSGLERCEGEKDKRRHCYASWRNSSGTIEIVKKGCWLDDFNCYD

RQECVATKENPQVYFCCCEGNFCNEKFSYFPQMEVTQPTSNPVTPKPP

Hybrid hu-ActRIIB-ECD
(SEQ ID NO: 104)
ETRECIYYNANWELERTNQSGLERCYGDQDKRRHCYASWRNSSGTIELVKKGCWLDDFNCYD

RQECVATEENPEVYFCCCEGNFCNEKFSYFPQMEVTQPTSNPVTPKPP

Hybrid hu-ActRIIB-ECD
(SEQ ID NO: 105)
ETRECIYYNANWELERTNQSGLERCEGEQDKRRHCYASWRNSSGTIELVKKGCWLDDFNCYD

RQECVATEENPQVYFCCCEGNFCNEKFSYFPQMEVTQPTSNPVTPKPP

Hybrid hu-ActRIIB-ECD
(SEQ ID NO: 106)
ETRECIYYNANWELERTNQSGLERCYGEQDKRLHCYASWRNSSGSIEIVKKGCWLDDFNCYD

RTDCVATEENPQVYFCCCEGNFCNEKFSYFPQMEVTQPTSNPVTPKPP

Hybrid hu-ActRIIB-ECD
(SEQ ID NO: 107)
ETRECIYYNANWELERTNQSGLERCEGEQDKRRHCYASWRNSSGSIELVKKGCWLDDFNCYD

RQECVAKEENPQVYFCCCEGNFCNEKFSYFPQMEVTQPTSNPVTPKPP

```
SEQUENCE LISTINGS

Hybrid hu-ActRIIB-ECD
                                                          (SEQ ID NO: 108)
ETRECIYYNANWELERTNQSGLERCEGEQDKRRHCYASWRNSSGTIEIVKKGCWLDDFNCYD

RQECVAKEENPQVYFCCCEGNFCNEKFSYFPQMEVTQPTSNPVTPKPP

Hybrid hu-ActRIIB-ECD
                                                          (SEQ ID NO: 109)
ETRECIYYNANWELERTNQSGLERCEGEQDKRRHCYASWRNSSGSIEIVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 110)
ETRECIYYNANWELERTNQSGLERCEGDQDKRLHCYASWRNSSGTIEIVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 111)
ETRECIYYNANWELERTNQSGLERCEGDQDKRLHCYASWRNSSGSIELVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 112)
ETRECIYYNANWELERTNQSGLERCEGDQDKRLHCYASWRNSSGTIELVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 113)
ETRECIYYNANWELERTNQSGLERCEGEQDKRLHCYASWRNSSGTIEIVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 114)
ETRECIYYNANWELERTNQSGLERCEGEQDKRLHCYASWRNSSGTIELVKKGCWLDDFNCYD

RQECVATKENPQVYFCCCEGNFCNEKFSYFPQMEVTQPTSNPVTPKPP

Hybrid hu-ActRIIB-ECD
                                                          (SEQ ID NO: 115)
ETRECIYYNANWELERTNQSGLERCEGDQDKRLHCYASWRNSSGTIEIVKKGCWLDDFNCYD

RQECVAKKENPQVYFCCCEGNFCNEKFSYFPQMEVTQPTSNPVTPKPP

Hybrid hu-ActRIIB-ECD
                                                          (SEQ ID NO: 116)
ETQECLFFNANWEKDRTNQTGVEPCYGDKDKRRHCFATWKNISGSIEIVKQGCWLDDINCYD

RTDCVEKKDSPEVYFCCCEGNMCNERFTHLPEAGGPEVTYEPPPTAPT

Hybrid hu-ActRIIB-ECD
                                                          (SEQ ID NO: 117)
ETRECIYYNANWELERTNQSGLERCYGDKDKRRHCYASWRNSSGTIELVKKGCWLDDINCYD

RQECVATKENPQVYFCCCEGNFCNERFTHLPEAGGPEVTYEPPPTAPT

Peptide Linker sequence
                                                          (SEQ ID NO: 118)
ESKYGPPCPPCP
```

What is claimed is:

1. An isolated hybrid activin IIB receptor (ActRIIB) ligand trap protein comprising a hybrid soluble activin IIB receptor-extracellular domain (ActRIIB-ECD) polypeptide, wherein said hybrid soluble ActRIIB-ECD polypeptide comprises an amino acid sequence selected from the group consisting of: SEQ ID NOs: 3-37 and 51-104.

2. An isolated hybrid ActRIIB ligand trap protein of claim 1, wherein said hybrid ActRIIB ligand trap protein further comprises an Fc domain of a human immunoglobulin, said Fc domain having an amino acid sequence selected from the group consisting of: SEQ ID NO: 39, SEQ ID NO: 41, and SEQ ID NO: 43.

3. An isolated hybrid ActRIIB ligand trap protein of claim 2, wherein a peptide linker comprising the amino acid sequence set forth in SEQ ID NO: 44 is used with a hinge linker comprising the amino acid sequence set forth in SEQ ID NO: 118 to link the Fc domain to the hybrid soluble ActRIIB-ECD polypeptide.

4. An isolated hybrid ActRIIB ligand trap protein of claim 3, wherein said hybrid soluble ActRIIB-ECD polypeptide comprises the amino acid sequence of SEQ ID NO: 16, wherein said hybrid soluble ActRIIB-ECD polypeptide is fused to a peptide linker comprising the amino acid sequence set forth in SEQ ID NO: 44, wherein said peptide linker is fused to a hinge linker comprising the amino acid sequence set forth in SEQ ID NO: 118, and wherein said hinge linker is fused to a human Fc domain comprising the amino acid sequence of SEQ ID NO: 43.

5. An isolated hybrid ActRIIB ligand trap protein of claim 3, wherein said hybrid soluble ActRIIB-ECD polypeptide comprises the amino acid sequence of SEQ ID NO: 29, wherein said hybrid soluble ActRIIB-ECD polypeptide is fused to a peptide linker comprising the amino acid sequence set forth in SEQ ID NO: 44, wherein said peptide linker is fused to a hinge linker comprising the amino acid sequence set forth in SEQ ID NO: 118, and wherein said hinge linker is fused to a human Fc domain comprising the amino acid sequence of SEQ ID NO: 43.

6. A pharmaceutical composition comprising a therapeutically effective amount of the hybrid ActRIIB ligand trap protein of claim 1 in admixture with a pharmaceutically acceptable carrier.

7. A method of treating muscle wasting in a subject, comprising administering to said subject a therapeutically effective amount of the pharmaceutical composition comprising a hybrid soluble activin IIB receptor-extracellular domain (ActRIIB-ECD) polypeptide wherein said hybrid soluble ActRIIB-ECD polypeptide comprises the amino acid sequence selected from the group consisting of SEQ ID NO: 16 and of SEQ ID NO: 29 fused to an Fc domain of a human immunoglobulin by a peptide linker sequence and wherein the muscle wasting is associated with a cardiovascular disease selected from the group consisting of: heart failure, cardiac atrophy, pulmonary arterial hypertension (PAH), myocarditis, coronary artery disease, myocardial infarction, cardiac arrhythmias, heart valve disease, cardiomyopathy, pericardial disease, aorta disease, Marfan syndrome and cardiac transplant.

8. A method of treating bone disease in a subject, comprising administering to said subject a therapeutically effective amount of the pharmaceutical composition comprising a hybrid soluble activin IIB receptor-extracellular domain (ActRIIB-ECD) polypeptide wherein said hybrid soluble ActRIIB-ECD polypeptide comprises the amino acid sequence selected from the group consisting of SEQ ID NO: 16 and of SEQ ID NO: 29 fused to an Fc domain of a human immunoglobulin by a peptide linker sequence and wherein the bone disease is selected from the group consisting of: osteoporosis, renal osteodystrophy, osteomalacia, osteogenesis imperfecta, fibrodysplasia ossificans progressiva, corticosteroid-induced bone loss, androgen-deprivation therapy-induced bone loss, bone fracture, cancer-induced bone loss, bone metastasis, Paget's disease of the bone, Rickets, Perthes' disease and fibrous dysplasia.

* * * * *

SEQUENCE LISTING

<160> NUMBER OF SEQ ID NOS: 118

<210> SEQ ID NO 1
<211> LENGTH: 110
<212> TYPE: PRT
<213> ORGANISM: Homo sapiens

<400> SEQUENCE: 1

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 2
<211> LENGTH: 110
<212> TYPE: PRT
<213> ORGANISM: Homo sapiens

<400> SEQUENCE: 2

Glu Thr Gln Glu Cys Leu Phe Phe Asn Ala Asn Trp Glu Lys Asp Arg
1               5                   10                  15

Thr Asn Gln Thr Gly Val Glu Pro Cys Tyr Gly Asp Lys Asp Lys Arg
            20                  25                  30

Arg His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Met Cys Asn Glu Lys Phe Ser Tyr Phe Pro Glu Met Glu
                85                  90                  95

Val Thr Gln Pro Thr Ser Asn Pro Val Thr Pro Lys Pro Pro
            100                 105                 110

<210> SEQ ID NO 3
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 3

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly

Gly Pro Glu Val Thr Tyr Glu Pro Pro Thr Ala Pro Thr
                100                 105                 110

<210> SEQ ID NO 4
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 4

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Thr
50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 5
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 5

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Thr
50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 6
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 6

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Ile Asn Cys Tyr Asp Arg Thr
 50                  55                  60

Asp Cys Val Glu Lys Lys Asp Ser Pro Gln Val Tyr Phe Cys Cys Cys
 65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 7
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 7

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Thr
 50                  55                  60

Asp Cys Val Glu Lys Lys Asp Ser Pro Gln Val Tyr Phe Cys Cys Cys
 65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 8
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 8

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr 100             105             110

<210> SEQ ID NO 9
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 9

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 10
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 10

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Glu Lys Lys Asp Ser Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 11
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 11

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

```
Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
 50                  55                  60

Glu Cys Val Glu Lys Lys Asp Ser Pro Glu Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110

<210> SEQ ID NO 12
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 12

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
                 20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Met Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110

<210> SEQ ID NO 13
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 13

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Asp Gln Asp Lys Arg
                 20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
 50                  55                  60

Glu Cys Val Glu Lys Lys Asp Ser Pro Glu Val Tyr Phe Cys Cys Cys
 65                  70                  75                  80

Glu Gly Asn Met Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110
```

```
<210> SEQ ID NO 14
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 14

Glu Thr Gln Glu Cys Ile Tyr Tyr Asn Ala Asn Trp Glu Lys Asp Arg
1               5                   10                  15

Thr Asn Gln Thr Gly Val Glu Pro Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 15
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 15

Glu Thr Gln Glu Cys Ile Tyr Tyr Asn Ala Asn Trp Glu Lys Asp Arg
1               5                   10                  15

Thr Asn Gln Thr Gly Val Glu Pro Cys Glu Gly Asp Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 16
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 16

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45
```

Val Lys Lys Gly Cys Trp Leu Asp Asp Phe Asn Cys Tyr Asp Arg Gln
 50                  55                  60

Glu Cys Val Ala Thr Glu Asn Pro Gln Val Tyr Phe Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110

<210> SEQ ID NO 17
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 17

Glu Thr Arg Glu Cys Ile Tyr Tyr Asn Ala Asn Trp Glu Lys Asp Arg
 1               5                  10                  15

Thr Asn Gln Thr Gly Val Glu Pro Cys Glu Gly Asp Gln Asp Lys Arg
                20                  25                  30

Leu His Cys Tyr Ala Ser Trp Arg Asn Ser Ser Gly Thr Ile Glu Leu
             35                  40                  45

Val Lys Lys Gly Cys Trp Leu Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110

<210> SEQ ID NO 18
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 18

Glu Thr Gln Glu Cys Ile Tyr Tyr Asn Ala Asn Trp Glu Lys Asp Arg
 1               5                  10                  15

Thr Asn Gln Thr Gly Val Glu Pro Cys Glu Gly Asp Gln Asp Lys Arg
                20                  25                  30

Leu His Cys Tyr Ala Ser Trp Arg Asn Ser Ser Gly Thr Ile Glu Leu
             35                  40                  45

Val Lys Lys Gly Cys Trp Leu Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
                100                 105                 110

<210> SEQ ID NO 19
<211> LENGTH: 110
<212> TYPE: PRT

<213> ORGANISM: Artificial
<220> FEATURE:
<223> OTHER INFORMATION: Hybrid Human ActRIIB ECD

<400> SEQUENCE: 19

```
Glu Thr Gln Glu Cys Ile Tyr Tyr Asn Ala Asn Trp Glu Lys Asp Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
            85                  90                  95

Gly Pro Glu Val Thr Tyr Glu Pro Pro Thr Ala Pro Thr
            100                 105                 110
```

<210> SEQ ID NO 20
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 20

```
Glu Thr Gln Glu Cys Ile Tyr Tyr Asn Ala Asn Trp Glu Lys Asp Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
            85                  90                  95

Gly Pro Glu Val Thr Tyr Glu Pro Pro Thr Ala Pro Thr
            100                 105                 110
```

<210> SEQ ID NO 21
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 21

```
Glu Thr Arg Glu Cys Ile Tyr Tyr Asn Ala Asn Trp Glu Lys Asp Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60
```

-continued

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 22
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 22

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 23
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 23

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Phe Ala Thr Trp Arg Asn Ser Ser Gly Thr Ile Glu Leu
            35                  40                  45

Val Lys Gln Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 24
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 24

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
            85                  90                  95

Gly Pro Glu Val Thr Tyr Glu Pro Pro Pro Thr Ala Pro Thr
            100                 105                 110
```

<210> SEQ ID NO 25
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 25

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
            85                  90                  95

Gly Pro Glu Val Thr Tyr Glu Pro Pro Pro Thr Ala Pro Thr
            100                 105                 110
```

<210> SEQ ID NO 26
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 26

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
50                  55                  60

Glu Cys Val Ala Thr Glu Glu Asn Pro Gln Val Tyr Phe Cys Cys Cys
65                  70                  75                  80
```

-continued

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 27
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 27

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 28
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 28

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Lys Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 29
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 29

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
                35                  40                  45

Val Lys Lys Gly Cys Trp Leu Asp Asp Ile Asn Cys Tyr Asp Arg Gln
50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110
```

<210> SEQ ID NO 30
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 30

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
                35                  40                  45

Val Lys Lys Gly Cys Trp Leu Asp Asp Phe Asn Cys Tyr Asp Arg Gln
50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110
```

<210> SEQ ID NO 31
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 31

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
                35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95
```

Gly Pro Glu Val Thr Tyr Glu Pro Pro Thr Ala Pro Thr
            100                 105                 110

<210> SEQ ID NO 32
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 32

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
    50                  55                  60

Glu Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 33
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 33

Glu Thr Arg Glu Cys Ile Phe Phe Asn Ala Asn Trp Glu Lys Asp Arg
1               5                   10                  15

Thr Asn Gln Thr Gly Val Glu Pro Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 34
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 34

Glu Thr Arg Glu Cys Ile Tyr Tyr Asn Ala Asn Trp Glu Leu Glu Arg
1               5                   10                  15

```
Thr Asn Gln Ser Gly Leu Glu Arg Cys Glu Gly Glu Gln Asp Lys Arg
            20                  25                  30

Leu His Cys Phe Ala Thr Trp Lys Asn Ile Ser Gly Ser Ile Glu Leu
            35                  40                  45

Val Lys Gln Gly Cys Trp Leu Asp Asp Phe Asn Cys Tyr Asp Arg Gln
        50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 35
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 35

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Thr
        50                  55                  60

Asp Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 36
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 36

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
        50                  55                  60

Glu Cys Val Ala Thr Glu Glu Asn Pro Gln Val Tyr Phe Cys Cys Cys
65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110
```

```
<210> SEQ ID NO 37
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 37

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 38
<211> LENGTH: 330
<212> TYPE: PRT
<213> ORGANISM: Homo sapiens

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 39
<211> LENGTH: 208
<212> TYPE: PRT
<213> ORGANISM: Homo sapiens

<400> SEQUENCE: 39

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

<210> SEQ ID NO 40
<211> LENGTH: 326
<212> TYPE: PRT
<213> ORGANISM: Homo sapiens

<400> SEQUENCE: 40
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 41
<211> LENGTH: 207
<212> TYPE: PRT
<213> ORGANISM: Homo sapiens

<400> SEQUENCE: 41

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Gln Phe Asn Trp Tyr Val Asp Gly Val Glu Val His Asn Ala
        35                  40                  45
```

```
Lys Thr Lys Pro Arg Glu Glu Gln Phe Asn Ser Thr Phe Arg Val Val
 50                  55                  60

Ser Val Leu Thr Val Val His Gln Asp Trp Leu Asn Gly Lys Glu Tyr
 65                  70                  75                  80

Lys Cys Lys Val Ser Asn Lys Gly Leu Pro Ala Pro Ile Glu Lys Thr
                 85                  90                  95

Ile Ser Lys Thr Lys Gly Gln Pro Arg Glu Pro Gln Val Tyr Thr Leu
            100                 105                 110

Pro Pro Ser Arg Glu Glu Met Thr Lys Asn Gln Val Ser Leu Thr Cys
            115                 120                 125

Leu Val Lys Gly Phe Tyr Pro Ser Asp Ile Ala Val Glu Trp Glu Ser
130                 135                 140

Asn Gly Gln Pro Glu Asn Asn Tyr Lys Thr Thr Pro Pro Met Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Cys Ser Val Met His Glu Ala Leu
            180                 185                 190

His Asn His Tyr Thr Gln Lys Ser Leu Ser Leu Ser Pro Gly Lys
            195                 200                 205

<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
```

```
              210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 43
<211> LENGTH: 217
<212> TYPE: PRT
<213> ORGANISM: Homo sapiens

<400> SEQUENCE: 43

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 44
<211> LENGTH: 5
<212> TYPE: PRT
<213> ORGANISM: Artificial
<220> FEATURE:
```

-continued

<223> OTHER INFORMATION: Peptide linker

<400> SEQUENCE: 44

Gly Gly Gly Gly Ser
1               5

<210> SEQ ID NO 45
<211> LENGTH: 512
<212> TYPE: PRT
<213> ORGANISM: Homo sapiens

<400> SEQUENCE: 45

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro

```
                    340                 345                 350
Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 46
<211> LENGTH: 116
<212> TYPE: PRT
<213> ORGANISM: Homo sapiens

<400> SEQUENCE: 46

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 47
<211> LENGTH: 513
<212> TYPE: PRT
<213> ORGANISM: Homo sapiens

<400> SEQUENCE: 47

Met Gly Ala Ala Thr Lys Leu Ala Phe Ala Val Phe Leu Ile Ser Cys
1               5                   10                  15

Ser Ser Gly Ala Ile Leu Gly Arg Ser Glu Thr Gln Glu Cys Ile Tyr
            20                  25                  30

Tyr Asn Ala Asn Trp Glu Lys Asp Lys Thr Asn Arg Ser Gly Ile Glu
```

```
            35                  40                  45
Pro Cys Tyr Gly Asp Lys Asp Lys Arg Arg His Cys Phe Ala Thr Trp
50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Asn Asp Cys Ile Glu Lys Lys Asp
                85                  90                  95

Ser Pro Glu Val Phe Phe Cys Cys Glu Gly Asn Met Cys Asn Glu
            100                 105                 110

Arg Phe Phe Tyr Phe Pro Glu Met Glu Val Thr Gln Pro Thr Ser Asn
            115                 120                 125

Pro Val Thr Pro Lys Pro Pro Leu Phe Asn Thr Leu Leu Tyr Ser Leu
130                 135                 140

Val Pro Ile Met Gly Ile Ala Val Ile Val Leu Phe Ser Phe Trp Met
145                 150                 155                 160

Tyr Arg His His Lys Leu Ala Tyr Pro Pro Val Leu Val Pro Thr Gln
                165                 170                 175

Asp Pro Gly Pro Pro Pro Ser Pro Leu Met Gly Leu Lys Pro Leu
                180                 185                 190

Gln Leu Leu Glu Ile Lys Ala Arg Gly Arg Phe Gly Cys Val Trp Lys
            195                 200                 205

Ala Gln Leu Leu Asn Glu Tyr Val Ala Val Lys Ile Phe Pro Ile Gln
210                 215                 220

Asp Lys Gln Ser Trp Gln Asn Glu Tyr Glu Ile Tyr Ser Leu Pro Gly
225                 230                 235                 240

Met Lys His Asp Asn Ile Leu Gln Phe Ile Gly Ala Glu Lys Arg Gly
                245                 250                 255

Thr Ser Ile Asp Val Asp Leu Trp Leu Ile Thr Ala Phe His Glu Lys
                260                 265                 270

Gly Ser Leu Thr Asp Phe Leu Lys Ala Asn Val Val Ser Trp Asn Glu
            275                 280                 285

Leu Cys His Ile Ala Gln Thr Met Ala Arg Gly Leu Ala Tyr Leu His
            290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
            370                 375                 380

Ile Asp Met Tyr Ala Met Gly Leu Val Leu Trp Glu Leu Ala Ser Arg
385                 390                 395                 400

Cys Thr Ala Ser Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Glu Cys Trp Gln Lys His
            435                 440                 445

Ser Gly Met Ala Met Leu Cys Glu Thr Ile Glu Glu Cys Trp Asp His
450                 455                 460
```

```
Asp Ala Glu Ala Arg Leu Ser Ala Gly Cys Val Glu Arg Ile Ile
465                 470                 475                 480

Gln Met Gln Lys Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 48
<211> LENGTH: 116
<212> TYPE: PRT
<213> ORGANISM: Homo sapiens

<400> SEQUENCE: 48

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
                20                  25                  30

Gly Asp Lys Asp Lys Arg Arg His Cys Phe Ala Thr Trp Lys Asn Ile
            35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
                100                 105                 110

Pro Lys Pro Pro
            115

<210> SEQ ID NO 49
<211> LENGTH: 18
<212> TYPE: PRT
<213> ORGANISM: Artificial
<220> FEATURE:
<223> OTHER INFORMATION: ActRIIB signal peptide

<400> SEQUENCE: 49

Met Thr Ala Pro Trp Val Ala Leu Ala Leu Leu Trp Gly Ser Leu Cys
1               5                   10                  15

Ala Gly

<210> SEQ ID NO 50
<211> LENGTH: 22
<212> TYPE: PRT
<213> ORGANISM: Artificial
<220> FEATURE:
<223> OTHER INFORMATION: Immunoglobulin light chain signal peptide

<400> SEQUENCE: 50

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 51
<211> LENGTH: 110
<212> TYPE: PRT
```

<213> ORGANISM: Artificial
<220> FEATURE:
<223> OTHER INFORMATION: Hybrid Human ActRIIB ECD

<400> SEQUENCE: 51

Glu Thr Gln Glu Cys Leu Phe Phe Asn Ala Asn Trp Glu Lys Asp Arg
1               5                   10                  15

Thr Asn Gln Ser Gly Val Glu Pro Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 52
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 52

Glu Thr Gln Glu Cys Leu Phe Phe Asn Ala Asn Trp Glu Lys Asp Arg
1               5                   10                  15

Thr Asn Gln Ser Gly Val Glu Pro Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 53
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 53

Glu Thr Arg Glu Cys Leu Phe Phe Asn Ala Asn Trp Glu Lys Asp Arg
1               5                   10                  15

Thr Asn Gln Ser Gly Val Glu Pro Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 54
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 54

Glu Thr Gln Glu Cys Leu Phe Phe Asn Ala Asn Trp Glu Lys Asp Arg
1               5                   10                  15

Thr Asn Gln Ser Gly Val Glu Pro Cys Tyr Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 55
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 55

Glu Thr Arg Glu Cys Leu Phe Phe Asn Ala Asn Trp Glu Lys Asp Arg
1               5                   10                  15

Thr Asn Gln Ser Gly Val Glu Pro Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 56
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 56

| Glu | Thr | Arg | Glu | Cys | Leu | Phe | Phe | Asn | Ala | Asn | Trp | Glu | Lys | Asp | Arg |
| 1 | | | | 5 | | | | | 10 | | | | | 15 | |

| Thr | Asn | Gln | Thr | Gly | Val | Glu | Pro | Cys | Tyr | Gly | Asp | Lys | Asp | Lys | Arg |
| | | | 20 | | | | | 25 | | | | | 30 | | |

| Arg | His | Cys | Phe | Ala | Thr | Trp | Lys | Asn | Ile | Ser | Gly | Ser | Ile | Glu | Ile |
| | | 35 | | | | | 40 | | | | | 45 | | | |

| Val | Lys | Gln | Gly | Cys | Trp | Leu | Asp | Asp | Phe | Asn | Cys | Tyr | Asp | Arg | Gln |
| | 50 | | | | | 55 | | | | | 60 | | | | |

| Glu | Cys | Val | Ala | Thr | Glu | Glu | Asn | Pro | Gln | Val | Tyr | Phe | Cys | Cys | Cys |
| 65 | | | | | 70 | | | | | 75 | | | | | 80 |

| Glu | Gly | Asn | Phe | Cys | Asn | Glu | Arg | Phe | Thr | His | Leu | Pro | Glu | Ala | Gly |
| | | | | 85 | | | | | 90 | | | | | 95 | |

| Gly | Pro | Glu | Val | Thr | Tyr | Glu | Pro | Pro | Pro | Thr | Ala | Pro | Thr |
| | | | 100 | | | | | 105 | | | | | 110 |

<210> SEQ ID NO 57
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 57

| Glu | Thr | Arg | Glu | Cys | Leu | Phe | Phe | Asn | Ala | Asn | Trp | Glu | Lys | Asp | Arg |
| 1 | | | | 5 | | | | | 10 | | | | | 15 | |

| Thr | Asn | Gln | Thr | Gly | Val | Glu | Pro | Cys | Tyr | Gly | Asp | Lys | Asp | Lys | Arg |
| | | | 20 | | | | | 25 | | | | | 30 | | |

| Arg | His | Cys | Phe | Ala | Thr | Trp | Lys | Asn | Ile | Ser | Gly | Ser | Ile | Glu | Ile |
| | | 35 | | | | | 40 | | | | | 45 | | | |

| Val | Lys | Gln | Gly | Cys | Trp | Leu | Asp | Asp | Ile | Asn | Cys | Tyr | Asp | Arg | Gln |
| | 50 | | | | | 55 | | | | | 60 | | | | |

| Glu | Cys | Val | Ala | Thr | Glu | Glu | Asn | Pro | Gln | Val | Tyr | Phe | Cys | Cys | Cys |
| 65 | | | | | 70 | | | | | 75 | | | | | 80 |

| Glu | Gly | Asn | Phe | Cys | Asn | Glu | Arg | Phe | Thr | His | Leu | Pro | Glu | Ala | Gly |
| | | | | 85 | | | | | 90 | | | | | 95 | |

| Gly | Pro | Glu | Val | Thr | Tyr | Glu | Pro | Pro | Pro | Thr | Ala | Pro | Thr |
| | | | 100 | | | | | 105 | | | | | 110 |

<210> SEQ ID NO 58
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 58

| Glu | Thr | Arg | Glu | Cys | Leu | Phe | Phe | Asn | Ala | Asn | Trp | Glu | Lys | Asp | Arg |
| 1 | | | | 5 | | | | | 10 | | | | | 15 | |

| Thr | Asn | Gln | Thr | Gly | Val | Glu | Pro | Cys | Tyr | Gly | Asp | Lys | Asp | Lys | Arg |
| | | | 20 | | | | | 25 | | | | | 30 | | |

| Arg | His | Cys | Phe | Ala | Thr | Trp | Lys | Asn | Ile | Ser | Gly | Ser | Ile | Glu | Ile |
| | | 35 | | | | | 40 | | | | | 45 | | | |

| Val | Lys | Gln | Gly | Cys | Trp | Leu | Asp | Asp | Ile | Asn | Cys | Tyr | Asp | Arg | Thr |
| | 50 | | | | | 55 | | | | | 60 | | | | |

| Asp | Cys | Val | Glu | Lys | Lys | Asp | Ser | Pro | Glu | Val | Tyr | Phe | Cys | Cys | Cys |
| 65 | | | | | 70 | | | | | 75 | | | | | 80 |

```
Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 59
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 59

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
                20                  25                  30

Arg His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Gln
50                  55                  60

Glu Cys Val Ala Thr Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 60
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 60

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
                20                  25                  30

Arg His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Thr
50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 61
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 61
```

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Thr
50              55                  60

Asp Cys Val Glu Lys Lys Asp Ser Pro Glu Val Tyr Phe Cys Cys Cys
65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 62
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 62

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Thr
50              55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 63
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 63

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Thr
50              55                  60

Asp Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

-continued

Gly Pro Glu Val Thr Tyr Glu Pro Pro Thr Ala Pro Thr
            100                 105                 110

<210> SEQ ID NO 64
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 64

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Phe Ala Thr Trp Lys Asn Ile Ser Gly Ser Ile Glu Ile
        35                  40                  45

Val Lys Gln Gly Cys Trp Leu Asp Asp Phe Asn Cys Tyr Asp Arg Thr
    50                  55                  60

Asp Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 65
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 65

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Phe Ala Thr Trp Lys Asn Ile Ser Gly Ser Ile Glu Ile
        35                  40                  45

Val Lys Gln Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 66
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 66

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
                20                  25                  30

Arg His Cys Tyr Ala Ser Trp Arg Asn Ser Ser Gly Thr Ile Glu Leu
            35                  40                  45

Val Lys Lys Gly Cys Trp Leu Asp Asp Ile Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 67
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 67

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
                20                  25                  30

Arg His Cys Tyr Ala Ser Trp Arg Asn Ser Ser Gly Thr Ile Glu Leu
            35                  40                  45

Val Lys Lys Gly Cys Trp Leu Asp Asp Ile Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 68
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 68

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
                20                  25                  30

Arg His Cys Phe Ala Thr Trp Lys Asn Ile Ser Gly Ser Ile Glu Ile
            35                  40                  45

Val Lys Gln Gly Cys Trp Leu Asp Asp Ile Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

-continued

<210> SEQ ID NO 69
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 69

Glu Thr Gln Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 70
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 70

Glu Thr Arg Glu Cys Leu Phe Phe Asn Ala Asn Trp Glu Lys Asp Arg
1               5                   10                  15

Thr Asn Gln Thr Gly Val Glu Pro Cys Glu Gly Glu Gln Asp Lys Arg
            20                  25                  30

Leu His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 71
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 71

Glu Thr Arg Glu Cys Leu Phe Phe Asn Ala Asn Trp Glu Lys Asp Arg
1               5                   10                  15

Thr Asn Gln Ser Gly Val Glu Pro Cys Glu Gly Glu Gln Asp Lys Arg
            20                  25                  30

```
Leu His Cys Tyr Ala Ser Trp Arg Asn Ser Ser Gly Thr Ile Glu Leu
         35                  40                  45

Val Lys Lys Gly Cys Trp Leu Asp Asp Ile Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 72
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 72

Glu Thr Arg Glu Cys Leu Phe Phe Asn Ala Asn Trp Glu Lys Asp Arg
 1               5                  10                  15

Thr Asn Gln Ser Gly Val Glu Pro Cys Tyr Gly Asp Lys Asp Lys Arg
             20                  25                  30

Arg His Cys Tyr Ala Ser Trp Arg Asn Ser Ser Gly Thr Ile Glu Leu
         35                  40                  45

Val Lys Lys Gly Cys Trp Leu Asp Asp Ile Asn Cys Tyr Asp Arg Thr
 50                  55                  60

Asp Cys Val Glu Lys Lys Asp Ser Pro Glu Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 73
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 73

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Tyr Gly Asp Lys Asp Lys Arg
             20                  25                  30

Arg His Cys Tyr Ala Ser Trp Arg Asn Ser Ser Gly Thr Ile Glu Leu
         35                  40                  45

Val Lys Lys Gly Cys Trp Leu Asp Asp Phe Asn Cys Tyr Asp Arg Thr
 50                  55                  60

Asp Cys Val Ala Thr Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 74
```

```
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 74

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Gln Gly Cys Trp Leu Asp Asp Phe Asn Cys Tyr Asp Arg Thr
50                  55                  60

Asp Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 75
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 75

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Thr
50                  55                  60

Asp Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 76
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 76

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Ser Ile Glu Leu
        35                  40                  45
```

Val Lys Lys Gly Cys Trp Leu Asp Asp Phe Asn Cys Tyr Asp Arg Thr
 50                  55                  60

Asp Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 77
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 77

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Tyr Gly Asp Lys Asp Lys Arg
                 20                  25                  30

Arg His Cys Tyr Ala Ser Trp Arg Asn Ser Ser Gly Ser Ile Glu Ile
             35                  40                  45

Val Lys Lys Gly Cys Trp Leu Asp Asp Phe Asn Cys Tyr Asp Arg Thr
 50                  55                  60

Asp Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 78
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 78

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Tyr Gly Asp Lys Asp Lys Arg
                 20                  25                  30

Arg His Cys Tyr Ala Ser Trp Arg Asn Ser Ser Gly Ser Ile Glu Ile
             35                  40                  45

Val Lys Gln Gly Cys Trp Leu Asp Asp Phe Asn Cys Tyr Asp Arg Thr
 50                  55                  60

Asp Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr
            100                 105                 110

<210> SEQ ID NO 79
<211> LENGTH: 110
<212> TYPE: PRT
<213> ORGANISM: Artificial

```
<220> FEATURE:
<223> OTHER INFORMATION: Hybrid Human ActRIIB ECD

<400> SEQUENCE: 79

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Thr
    50                  55                  60

Asp Cys Val Ala Thr Glu Glu Asn Pro Gln Val Tyr Phe Cys Cys Cys
65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Pro Thr Ala Pro Thr
                100                 105                 110

<210> SEQ ID NO 80
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 80

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Glu Met Glu
                85                  90                  95

Val Thr Gln Pro Thr Ser Asn Pro Val Thr Pro Lys Pro Pro
                100                 105                 110

<210> SEQ ID NO 81
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 81

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
    50                  55                  60
```

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 82
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 82

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 83
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 83

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 84
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 84

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110
```

<210> SEQ ID NO 85
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 85

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Gln Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110
```

<210> SEQ ID NO 86
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 86

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80
```

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 87
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 87

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Ser Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 88
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 88

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Ser Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 89
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 89

Glu Thr Arg Glu Cys Ile Tyr Tyr Asn Ala Asn Trp Glu Leu Glu Arg

-continued

```
                1               5                  10                 15
          Thr Asn Gln Ser Gly Leu Glu Arg Cys Glu Gly Glu Gln Asp Lys Arg
                        20                 25                 30

Leu His Cys Tyr Ala Ser Trp Arg Asn Ser Ser Gly Thr Ile Glu Ile
                        35                 40                 45

Val Lys Lys Gly Cys Trp Leu Asp Asp Phe Asn Cys Tyr Asp Arg Gln
                        50                 55                 60

Glu Cys Val Ala Thr Glu Glu Asn Pro Gln Val Tyr Phe Cys Cys Cys
          65                     70                 75                 80

Glu Gly Asn Phe Cys Asn Glu Lys Phe Ser Tyr Phe Pro Gln Met Glu
                            85                 90                 95

Val Thr Gln Pro Thr Ser Asn Pro Val Thr Pro Lys Pro Pro
                       100                105                110

<210> SEQ ID NO 90
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 90

Glu Thr Arg Glu Cys Ile Tyr Tyr Asn Ala Asn Trp Glu Leu Glu Arg
          1               5                  10                 15

Thr Asn Gln Ser Gly Leu Glu Arg Cys Glu Gly Glu Gln Asp Lys Arg
                        20                 25                 30

Leu His Cys Tyr Ala Ser Trp Arg Asn Ser Ser Gly Thr Ile Glu Leu
                        35                 40                 45

Val Lys Gln Gly Cys Trp Leu Asp Asp Phe Asn Cys Tyr Asp Arg Gln
                        50                 55                 60

Glu Cys Val Ala Thr Glu Glu Asn Pro Gln Val Tyr Phe Cys Cys Cys
          65                     70                 75                 80

Glu Gly Asn Phe Cys Asn Glu Lys Phe Ser Tyr Phe Pro Gln Met Glu
                            85                 90                 95

Val Thr Gln Pro Thr Ser Asn Pro Val Thr Pro Lys Pro Pro
                       100                105                110

<210> SEQ ID NO 91
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 91

Glu Thr Arg Glu Cys Ile Tyr Tyr Asn Ala Asn Trp Glu Leu Glu Arg
          1               5                  10                 15

Thr Asn Gln Ser Gly Leu Glu Arg Cys Glu Gly Glu Gln Asp Lys Arg
                        20                 25                 30

Leu His Cys Tyr Ala Ser Trp Arg Asn Ser Ser Gly Thr Ile Glu Leu
                        35                 40                 45

Val Lys Lys Gly Cys Trp Leu Asp Asp Phe Asn Cys Tyr Asp Arg Gln
                        50                 55                 60

Glu Cys Val Glu Thr Glu Glu Asn Pro Gln Val Tyr Phe Cys Cys Cys
          65                     70                 75                 80

Glu Gly Asn Phe Cys Asn Glu Lys Phe Ser Tyr Phe Pro Gln Met Glu
                            85                 90                 95
```

Val Thr Gln Pro Thr Ser Asn Pro Val Thr Pro Lys Pro Pro
            100                 105                 110

<210> SEQ ID NO 92
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 92

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 93
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 93

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 94
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 94

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg

```
                    20                  25                  30
Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
        50                  55                  60

Glu Cys Val Ala Thr Glu Asp Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
                100                 105                 110

<210> SEQ ID NO 95
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 95

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
        50                  55                  60

Glu Cys Val Ala Thr Glu Glu Ser Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
                100                 105                 110

<210> SEQ ID NO 96
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 96

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
        50                  55                  60

Glu Cys Val Ala Thr Glu Glu Asn Pro Glu Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
                100                 105                 110
```

<210> SEQ ID NO 97
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 97

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Lys Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Glu Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 98
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 98

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Lys Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 99
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 99

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu

```
                  35                  40                  45

Val Lys Lys Gly Cys Trp Leu Asp Asp Phe Asn Cys Tyr Asp Arg Gln
 50                  55                  60

Glu Cys Val Ala Thr Lys Glu Asn Pro Gln Val Tyr Phe Cys Cys Cys
 65                  70                  75                  80

Glu Gly Asn Phe Cys Asn Glu Lys Phe Ser Tyr Phe Pro Gln Met Glu
                 85                  90                  95

Val Thr Gln Pro Thr Ser Asn Pro Val Thr Pro Lys Pro Pro
                100                 105                 110

<210> SEQ ID NO 100
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 100

Glu Thr Arg Glu Cys Ile Tyr Tyr Asn Ala Asn Trp Glu Leu Glu Arg
  1               5                  10                  15

Thr Asn Gln Ser Gly Leu Glu Arg Cys Glu Gly Asp Lys Asp Lys Arg
                 20                  25                  30

Leu His Cys Tyr Ala Ser Trp Arg Asn Ser Ser Gly Thr Ile Glu Leu
                 35                  40                  45

Val Lys Gln Gly Cys Trp Leu Asp Asp Phe Asn Cys Tyr Asp Arg Gln
 50                  55                  60

Glu Cys Val Ala Lys Lys Glu Asn Pro Gln Val Tyr Phe Cys Cys Cys
 65                  70                  75                  80

Glu Gly Asn Phe Cys Asn Glu Lys Phe Ser Tyr Phe Pro Gln Met Glu
                 85                  90                  95

Val Thr Gln Pro Thr Ser Asn Pro Val Thr Pro Lys Pro Pro
                100                 105                 110

<210> SEQ ID NO 101
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 101

Glu Thr Arg Glu Cys Ile Tyr Tyr Asn Ala Asn Trp Glu Leu Glu Arg
  1               5                  10                  15

Thr Asn Gln Ser Gly Leu Glu Arg Cys Glu Gly Asp Lys Asp Lys Arg
                 20                  25                  30

Leu His Cys Tyr Ala Ser Trp Arg Asn Ser Ser Gly Thr Ile Glu Ile
                 35                  40                  45

Val Lys Gln Gly Cys Trp Leu Asp Asp Phe Asn Cys Tyr Asp Arg Gln
 50                  55                  60

Glu Cys Val Ala Glu Lys Glu Asn Pro Gln Val Tyr Phe Cys Cys Cys
 65                  70                  75                  80

Glu Gly Asn Phe Cys Asn Glu Lys Phe Ser Tyr Phe Pro Gln Met Glu
                 85                  90                  95

Val Thr Gln Pro Thr Ser Asn Pro Val Thr Pro Lys Pro Pro
                100                 105                 110

<210> SEQ ID NO 102
<211> LENGTH: 110
```

```
<212> TYPE: PRT
<213> ORGANISM: Artificial
<220> FEATURE:
<223> OTHER INFORMATION: Hybrid Human ActRIIB ECD

<400> SEQUENCE: 102

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Gln Asp Lys Arg
            20                  25                  30

Leu His Cys Tyr Ala Ser Trp Arg Asn Ser Ser Gly Ser Ile Glu Ile
        35                  40                  45

Val Lys Gln Gly Cys Trp Leu Asp Asp Phe Asn Cys Tyr Asp Arg Gln
    50                  55                  60

Glu Cys Val Ala Lys Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 103
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 103

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Lys Asp Lys Arg
            20                  25                  30

Arg His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 104
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 104

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Gln Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
```

```
Glu Cys Val Ala Thr Glu Glu Asn Pro Glu Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 105
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 105

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Arg His Cys Tyr Ala Ser Trp Arg Asn Ser Ser Gly Thr Ile Glu Leu
            35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 106
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 106

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Glu Gln Asp Lys Arg
                20                  25                  30

Leu His Cys Tyr Ala Ser Trp Arg Asn Ser Ser Gly Ser Ile Glu Ile
            35                  40                  45

Val Lys Lys Gly Cys Trp Leu Asp Asp Phe Asn Cys Tyr Asp Arg Thr
50                  55                  60

Asp Cys Val Ala Thr Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110

<210> SEQ ID NO 107
<211> LENGTH: 110
<212> TYPE: PRT
<213> ORGANISM: Artificial
<220> FEATURE:
```

<223> OTHER INFORMATION: Hybrid Human ActRIIB ECD

<400> SEQUENCE: 107

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Arg His Cys Tyr Ala Ser Trp Arg Asn Ser Ser Gly Ser Ile Glu Leu
        35                  40                  45

Val Lys Lys Gly Cys Trp Leu Asp Asp Phe Asn Cys Tyr Asp Arg Gln
    50                  55                  60

Glu Cys Val Ala Lys Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110
```

<210> SEQ ID NO 108
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 108

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Arg His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Lys Glu Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
            100                 105                 110
```

<210> SEQ ID NO 109
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 109

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Arg His Cys Tyr Ala Ser Trp Arg Asn Ser Ser Gly Ser Ile Glu Ile
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
```

```
                65                  70                  75                  80
Glu Gly Asn Phe Cys Asn Glu Lys Phe Ser Tyr Phe Pro Gln Met Glu
                    85                  90                  95

Val Thr Gln Pro Thr Ser Asn Pro Val Thr Pro Lys Pro Pro
                100                 105                 110

<210> SEQ ID NO 110
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 110

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                    85                  90                  95

Val Thr Gln Pro Thr Ser Asn Pro Val Thr Pro Lys Pro Pro
                100                 105                 110

<210> SEQ ID NO 111
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 111

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Ser Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                    85                  90                  95

Val Thr Gln Pro Thr Ser Asn Pro Val Thr Pro Lys Pro Pro
                100                 105                 110

<210> SEQ ID NO 112
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 112
```

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
            85                  90                  95

Val Thr Gln Pro Thr Ser Asn Pro Val Thr Pro Lys Pro Pro
                100                 105                 110

<210> SEQ ID NO 113
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 113

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
            85                  90                  95

Val Thr Gln Pro Thr Ser Asn Pro Val Thr Pro Lys Pro Pro
                100                 105                 110

<210> SEQ ID NO 114
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 114

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu

-continued

```
                    85                  90                  95

Val Thr Gln Pro Thr Ser Asn Pro Val Thr Pro Lys Pro Pro
                100                 105                 110

<210> SEQ ID NO 115
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 115

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Ile
        35                  40                  45

Val Lys Lys Gly Cys Trp Leu Asp Asp Phe Asn Cys Tyr Asp Arg Gln
    50                  55                  60

Glu Cys Val Ala Lys Lys Glu Asn Pro Gln Val Tyr Phe Cys Cys Cys
65                  70                  75                  80

Glu Gly Asn Phe Cys Asn Glu Lys Phe Ser Tyr Phe Pro Gln Met Glu
                85                  90                  95

Val Thr Gln Pro Thr Ser Asn Pro Val Thr Pro Lys Pro Pro
                100                 105                 110

<210> SEQ ID NO 116
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 116

Glu Thr Gln Glu Cys Leu Phe Phe Asn Ala Asn Trp Glu Lys Asp Arg
1               5                   10                  15

Thr Asn Gln Thr Gly Val Glu Pro Cys Tyr Gly Asp Lys Asp Lys Arg
            20                  25                  30

Arg His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Met Cys Asn Glu Arg Phe Thr His Leu Pro Glu Ala Gly
                85                  90                  95

Gly Pro Glu Val Thr Tyr Glu Pro Pro Thr Ala Pro Thr
                100                 105                 110

<210> SEQ ID NO 117
<211> LENGTH: 110
<212> TYPE: PRT
<213> ORGANISM: Artificial
<220> FEATURE:
<223> OTHER INFORMATION: Hybrid Human ActRIIB ECD

<400> SEQUENCE: 117

Glu Thr Arg Glu Cys Ile Tyr Tyr Asn Ala Asn Trp Glu Leu Glu Arg
1               5                   10                  15
```

```
Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
                100                 105                 110

<210> SEQ ID NO 118
<211> LENGTH: 12
<212> TYPE: PRT
<213> ORGANISM: Artificial
<220> FEATURE:
<223> OTHER INFORMATION: Peptide linker

<400> SEQUENCE: 118

Glu Ser Lys Tyr Gly Pro Pro Cys Pro Pro Cys Pro
1               5                   10
```